(12) United States Patent
Chen et al.

(10) Patent No.: US 7,803,778 B2
(45) Date of Patent: Sep. 28, 2010

(54) GLUCOSE TRANSPORT INHIBITORS AND METHODS OF USE

(75) Inventors: Yuanwei Chen, North Haven, CT (US); Yan Feng, Shanghai (CN); Baihua Xu, Shanghai (CN); Binhua Lv, Shanghai (CN); Jiajia Dong, Shanghai (CN); Brian Seed, Derry, NH (US); Michael J. Hadd, San Diego, CA (US)

(73) Assignee: Theracos, Inc., Sunnyvale, CA (US)

( * ) Notice: Subject to any disclaimer, the term of this patent is extended or adjusted under 35 U.S.C. 154(b) by 521 days.

(21) Appl. No.: 11/752,226

(22) Filed: May 22, 2007

(65) Prior Publication Data

US 2007/0275907 A1 Nov. 29, 2007

Related U.S. Application Data

(60) Provisional application No. 60/808,166, filed on May 23, 2006, provisional application No. 60/897,650, filed on Jan. 26, 2007.

(51) Int. Cl.
*A01N 43/04* (2006.01)
*C07H 1/00* (2006.01)
*C07H 3/00* (2006.01)
*C08B 37/00* (2006.01)

(52) U.S. Cl. ........................ 514/23; 536/1.11
(58) Field of Classification Search ........................ None
See application file for complete search history.

(56) References Cited

U.S. PATENT DOCUMENTS

| | | | |
|---|---|---|---|
| 5,663,377 | A | 9/1997 | Curley, Jr. et al. |
| 6,089,238 | A | 7/2000 | Schneider et al. |
| 6,414,126 | B1 | 7/2002 | Ellsworth et al. |
| 2002/0111315 | A1 | 8/2002 | Washburn et al. |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2004/0259819 | A1 | 12/2004 | Frick et al. |
| 2005/0014704 | A1 | 1/2005 | Frick et al. |
| 2005/0032712 | A1 | 2/2005 | Urbanski |
| 2005/0037980 | A1 | 2/2005 | Rybczynski et al. |
| 2005/0187168 | A1 | 8/2005 | Eickelmann et al. |
| 2005/0209166 | A1 | 9/2005 | Eckhardt et al. |
| 2005/0209309 | A1 | 9/2005 | Sato et al. |
| 2005/0233988 | A1 | 10/2005 | Nomura et al. |
| 2006/0009400 | A1 | 1/2006 | Eckhardt et al. |
| 2006/0019948 | A1 | 1/2006 | Eckhardt et al. |
| 2006/0063722 | A1 | 3/2006 | Washburn et al. |
| 2006/0074031 | A1 | 4/2006 | Eckhardt et al. |
| 2006/0122126 | A1 | 6/2006 | Imamura et al. |
| 2006/0189548 | A1 | 8/2006 | Himmelsbach et al. |
| 2006/0234953 | A1 | 10/2006 | Himmelsbach et al. |
| 2006/0258749 | A1 | 11/2006 | Eckhardt et al. |
| 2007/0004648 | A1 | 1/2007 | Himmelsbach et al. |
| 2007/0027092 | A1 | 2/2007 | Himmelsbach et al. |
| 2007/0049537 | A1 | 3/2007 | Eckhardt et al. |
| 2007/0185197 | A1 | 8/2007 | Fujikura et al. |
| 2007/0197450 | A1 | 8/2007 | Fushimi et al. |
| 2008/0027014 | A1 | 1/2008 | Nomura et al. |
| 2008/0132563 | A1 | 6/2008 | Kakinuma et al. |
| 2008/0139484 | A1 | 6/2008 | Teranishi et al. |

FOREIGN PATENT DOCUMENTS

| | | |
|---|---|---|
| EP | 1 783 110 A1 | 5/2007 |
| EP | 1 803 721 A1 | 7/2007 |
| EP | 1 852 439 A1 | 11/2007 |
| WO | WO 98/31697 A1 | 7/1998 |

OTHER PUBLICATIONS

Stella, "Prodrugs as Therapeutics", Expert Opinion Ther. Patents (2004) 14(3), pp. 277-280.*
International Search Report mailed out on Feb. 7, 2008, for PCT Application No. PCT/US07/69487 filed on May 22, 2007, 2 pages.
Isaji, M., "Sodium-Glucose Cotransporter Inhibitors for Diabetes," *Current Opinion in Investigational Drugs*, 2007, vol. 8, No. 4, pp. 285-292.
Kuribayashi, T. et al., "*C*-Glycosylated Diphenylmethanes and benzophenones: The Stille Coupling Reaction of *C*-Glycosylated Aryl Tins With Benzyl Bromides and Acid Chlorides," *J. Carbohydrate Chemistry*, 1999, vol. 18, No. 4, pp. 393-401.

* cited by examiner

*Primary Examiner*—Traviss C McIntosh, III
(74) *Attorney, Agent, or Firm*—Townsend and Townsend and Crew LLP

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

29 Claims, 16 Drawing Sheets

Scheme I, Part A

Scheme I, Part B

Scheme I, Part C

Scheme II

Scheme III

Halo/halogeon = Br, Cl, I

Scheme IV

Scheme V

Scheme VI

Scheme VII

Scheme VIII

R' = H, OH, C$_1$-C$_6$ alkyl, C$_2$-C$_6$ alkenyl
Halo = Cl, Br, I
X = O, S, NH, SO, SO$_2$, methylene, difluoromethylene
Y = CO, CH$_2$, CD$_2$, CF$_2$, CHOH, CHOMe, CHF, CH(C$_1$-C$_6$ alkyl) and CH(C$_2$-C$_6$ alkenyl)
Z = methylene, difluoromethylene, 1,1-cyclopropylene

Scheme IX

X = O, S, NH, SO, SO₂, methylene, difluoromethylene
n = 0-3

Scheme X

Scheme XI

Scheme XII

Scheme XIII

GLUCOSE TRANSPORT INHIBITORS AND METHODS OF USE

CROSS REFERENCES TO RELATED APPLICATIONS

This application claims the benefit of U.S. Provisional Application Ser. Nos. 60/808,166 filed May 23, 2006 and 60/897,650, filed Jan. 26, 2007, the disclosures of which are incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

According to the World Health Organization, approximately 150 million people worldwide have diabetes mellitus. The two principle forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa K, et al., Br J Pharmacol 132:578-86, 2001; Oku A, et al., Diabetes 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., J Am Soc Nephrol 14:2873-82, 2003). Therefore, compounds which inhibit SGLT, particularly SGLT2, are promising candidates for use as antidiabetic drugs. Compounds previously described as useful for inhibiting SGLT include spiroketal-glycoside derivatives (described in WO2006080421), C-glycoside derivatives (such as those described in U.S. Pat. No. 6,414,126, US20050209166, US20050233988, WO2005085237, U.S. Pat. No. 7,094,763, US20060122126 and WO2006108842), O-glycoside derivatives (such as those described in U.S. Pat. No. 6,683,056, US20050187168, US20060166899, US20060234954 and US20060247179), cyclohexane derivatives (such as those described in WO2006011469), and thio-glucopyranoside derivatives (such as those described in US20050209309 and WO2006073197).

BRIEF SUMMARY OF THE INVENTION

The present invention provides compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

DETAILED DESCRIPTION OF THE INVENTION

Definitions

Figure 1A:
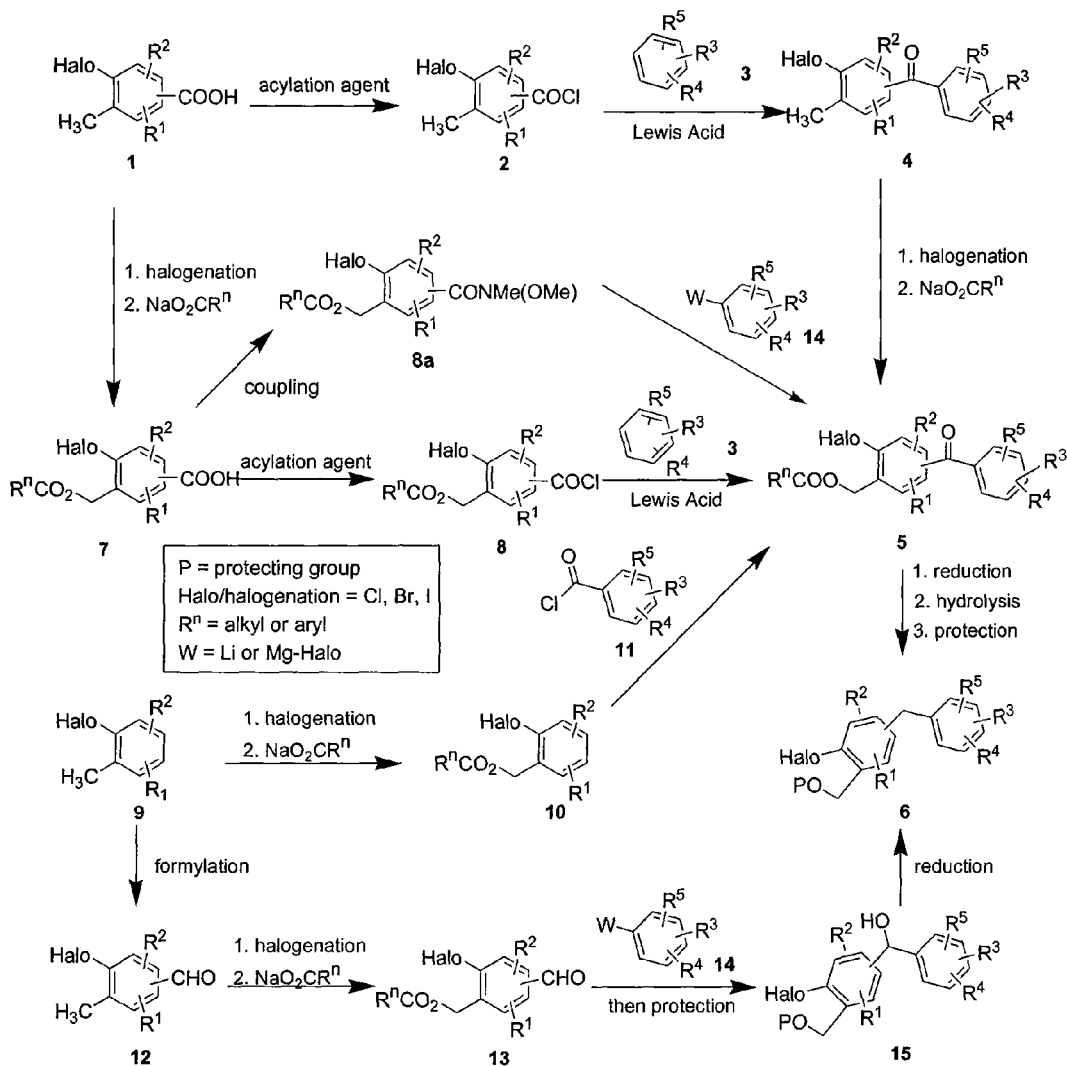
FIG. 1A is the general synthesis method of Scheme I, Part A, for the preparation of compounds of the invention.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the terms "alkylene" and "alkenylene" refer to a divalent hydrocarbon radical that is formed by removal of a hydrogen atom from an alkyl or alkenyl radical, respectively, as such terms are defined above.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons forming a carbocyclic ring and at least one carbon-carbon double bond and, where specified, optionally substituted with one to three suitable substituents as defined above. Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the term "aryl" alone or in combination refers to a monovalent aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound).

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21st Ed., Gennaro, Ed., Lippencott Williams & Wilkins (2003). As discussed therein, immediate and nonimmediate release can be defined kinetically by reference to the following equation:

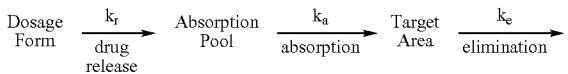

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

General

The present invention provides compounds having an inhibitory effect on sodium-dependent glucose cotransporter SGLT, preferably SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the compounds of the present invention are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

DETAILED EMBODIMENTS

Compounds and Preparative Methods

In one aspect, the present invention provides for compounds of Formula I:

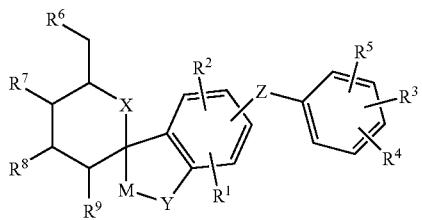

I wherein

M and X each independently represent oxygen; sulfur; SO; $SO_2$; methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy; $C_3$-$C_5$, 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; or NH optionally substituted with a substituent independently selected from $C_1$-$C_6$ alkyl, $C_3$-$C_6$ cycloalkyl or ($C_1$-$C_4$ alkyl)carbonyl; or M independently represents a single bond;

Y represents $(CH_2)_n$; $(CH_2)_m$CH=CH; CH=CH$(CH_2)_m$; $CH_2$CH=CHCH$_2$; $(CH_2)_m$C(O); C(O)$(CH_2)_m$; C(O)NH $(CH_2)_m$; $(CH_2)_m$NHC(O); C(O)O$(CH_2)_m$; $(CH_2)_m$SO$_2$; SO$_2$ $(CH_2)_m$; or (O)C$(CH_2)_m$C(O); wherein n is an integer from 1 to 3, m is an integer from 0 to 2, and each hydrogen independently may be optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy;

Z represents oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$)alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenemethyl, ($C_3$-$C_{10}$ cycloalkyloxy)$C_1$-$C_3$ alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, aryl, heteroaryl, ($C_1$-$C_4$ alkyl)carbonyl, arylcarbonyl, heteroarylcarbonyl, hydroxycarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups or portions may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group may be replaced by CO or $SO_2$;

$R^2$ represents hydrogen, halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano or nitro, wherein alkyl groups or portions may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_3$-$C_5$ alkylene, $C_3$-$C_5$ alkenylene or butadienylene bridge, which may be partly or completely fluorinated and may be mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups may be replaced by an N atom;

$R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$)alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_3$-$C_{10}$ cycloalkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_3$-$C_{10}$ cycloalkyl)$C_2$-$C_4$ alkenyl, $C_3$-$C_6$ cycloalkylidenemethyl, aryl, heteroaryl, ($C_1$-$C_4$ alkyl) carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, hydroxycarbonyl, ($C_1$-$C_4$ alkyloxy)carbonyl, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, heteroaryl-carbonylamino, $C_1$-$C_4$ alkylsulfonylamino, arylsulfonylamino, $C_1$-$C_6$ alkyloxy, $C_3$-$C_{10}$ cycloalkyloxy, $C_5$-$C_7$ cycloalkenyloxy, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, amino, hydroxy, cyano or nitro, wherein alkyl, alkenyl, alkynyl, cycloalkyl and cycloalkenyl groups or portions may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group may be replaced by CO or $SO_2$;

$R^4$ independently represents hydrogen, halo, hydroxy, cyano, nitro, $C_1$-$C_3$ alkyl, $C_3$-$C_{10}$ cycloalkyl, $C_3$-$C_{10}$ cycloalkyloxy and $C_1$-$C_3$ alkyloxy, wherein alkyl groups or portions may be mono- or polysubstituted by fluorine, or if $R^3$ and $R^4$ are bound to two adjacent C atoms of the phenyl ring, $R^3$ and $R^4$ may be joined together such that $R^3$ and $R^4$ together form a $C_3$-$C_5$ alkylene, $C_3$-$C_5$ alkenylene or butadienylene bridge, which may be partly or completely fluorinated and may be mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups may be replaced by an N atom;

$R^5$ independently represents hydrogen, halo, hydroxy, cyano, nitro, $C_1$-$C_3$ alkyl, $C_3$-$C_{10}$ cycloalkyl and $C_1$-$C_3$ alkyloxy, wherein alkyl groups or portions may be mono- or polysubstituted by fluorine; and $R^6$, $R^7$, $R^8$ and $R^9$ each independently represent hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$) cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$)cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy, or cyano; and wherein alkyl, alkenyl, alkynyl, cycloalkyl and cycloalkenyl groups or portions may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^a$, O, S, CO, SO or $SO_2$;

$R^a$ denotes H, $C_1$-$C_4$ alkyl or ($C_1$-$C_4$ alkyl)carbonyl.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, either in admixture or in pure or substantially pure form. The compounds of the present invention can have asymmetric centers at the carbon atoms, and therefore the compounds of Formula I can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formula I. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N-($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formula I and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds of Formula I and prodrugs thereof, as well as isotopically-labeled, pharmaceutically acceptable salts of compounds of Formula I and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

In preferred embodiments, X represents oxygen or sulfur. In particularly preferred embodiments, X represents oxygen.

In certain preferred embodiments, M represents oxygen or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In other preferred embodiments, M represents a single bond. In particularly preferred embodiments, M represents oxygen, methylene or a single bond.

In preferred embodiments, Y represents $(CH_2)_n$, $(CH_2)_m$CH=CH, CH=CH$(CH_2)_m$, $CH_2$CH=CHCH$_2$, wherein n is an integer from 1 to 3, m is an integer from 0 to 2, and each hydrogen independently may be optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Y represents $(CH_2)_n$, wherein n is an integer from 1 to 3.

In preferred embodiments, Z represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Z represents methylene.

In certain preferred embodiments, $R^1$ represents hydrogen, halo, $C_1$-$C_6$ alkyl, $C_3$-$C_{10}$ cycloalkyl, $(C_3$-$C_{10}$ cycloalkyl)$C_1$-$C_3$ alkyl, $(C_3$-$C_{10}$ cycloalkyloxy)$C_1$-$C_3$ alkyl, $(C_1$-$C_4$ alkyloxy)$C_1$-$C_3$ alkyl, $(C_1$-$C_4$ alkylamino)$C_1$-$C_3$ alkyl, di-$(C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions may be partly or completely fluorinated. In particularly preferred embodiments, $R^1$ represents hydrogen, halo or $C_1$-$C_6$ alkyl.

In certain preferred embodiments, $R^2$ represents hydrogen, halo, $C_1$-$C_4$ alkyl, or $C_1$-$C_4$ alkyloxy. In particularly preferred embodiments, $R^2$ represents hydrogen or halo.

In preferred embodiments, $R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, $(C_3$-$C_{10}$ cycloalkyl)$C_1$-$C_3$ alkyl, $(C_3$-$C_{10}$ cycloalkyloxy)$C_1$-$C_3$ alkyl, $(C_1$-$C_4$ alkyloxy)$C_1$-$C_3$ alkyl, $(C_1$-$C_4$ alkylamino)$C_1$-$C_3$ alkyl, di-$(C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions may be partly or completely fluorinated, and in cycloalkyl groups one or two methylene groups are optionally replaced independently of one another by O, S, CO, SO or $SO_2$. In particularly preferred embodiments, $R^3$ represents hydrogen, halo, $C_1$-$C_6$ alkyl, $C_1$-$C_6$ alkyloxy, $C_2$-$C_6$ alkynyl, or $C_3$-$C_{10}$ cycloalkyloxy, wherein alkyl and cycloalkyl groups or portions may be partly or completely fluorinated, and in cycloalkyl groups a methylene group is optionally replaced by O, S, CO, SO or $SO_2$.

In preferred embodiments, $R^4$ and $R^5$ independently represent hydrogen, hydroxy, cyano, nitro, halo, $C_1$-$C_3$ alkyl, $C_3$-$C_{10}$ cycloalkyl or $C_1$-$C_3$ alkoxy. In particularly preferred embodiments, $R^4$ and $R^5$ independently represent hydrogen, hydroxy or halo.

In preferred embodiments, $R^6$, $R^7$, $R^8$ and $R^9$ each independently represent hydroxy, halo, $C_1$-$C_6$ alkyl, $C_1$-$C_6$ alkyloxy, $(C_3$-$C_7)$cycloalkyloxy, aryloxy or $(C_3$-$C_7)$cycloalkyl-$(C_1$-$C_3)$alkyloxy, wherein alkyl and cycloalkyl groups or portions may be partly or completely fluorinated. In particularly preferred embodiments, $R^6$, $R^7$, $R^8$ and $R^9$ each represent hydroxy.

As noted above, Formula IA and IB represent still other preferred embodiments. In one group, the compounds are represented by Formula IA:

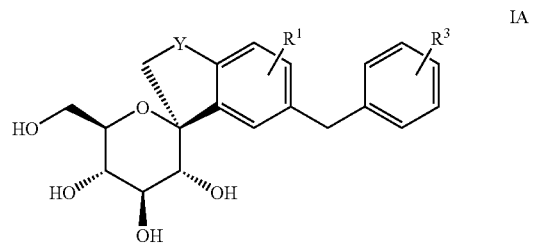

IA wherein Y represents $(CH_2)_n$, $(CH_2)_m$CH=CH, CH=CH$(CH_2)_m$, $CH_2$CH=CHCH$_2$, wherein n is an integer from 1 to 3, m is an integer from 0 to 2, and each hydrogen independently may be optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy; $R^1$ represents hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro; and $R^3$ represents hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein in cycloalkyl groups one or two methylene groups are optionally replaced independently of one another by O, S, CO, SO or $SO_2$.

In Formula I, where M and X both are oxygen, compounds in which $R^2$ is hydrogen and $R^1$ is halo in the para position relative to the spiro carbon are, surprisingly, significantly more potent inhibitors of SGLT2 than the corresponding compounds in which $R^1$ and $R^2$ both are hydrogen (see Example 52, Table 2 below). Accordingly, particularly preferred are compounds of Formula IB:

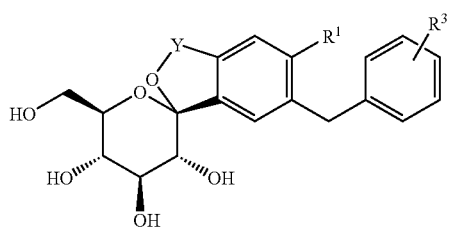

IB wherein Y represents $(CH_2)_n$, $(CH_2)_m CH=CH$, $CH=CH(CH_2)_m$, $CH_2CH=CHCH_2$, wherein n is an integer from 1 to 3, m is an integer from 0 to 2, and each hydrogen independently may be optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy; $R^1$ represents halo; and $R^3$ represents hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein in cycloalkyl groups one or two methylene groups are optionally replaced independently of one another by O, S, CO, SO or $SO_2$.

In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In other aspects, the present invention provides intermediates and processes useful for preparing the intermediates below as well as the compounds of Formula I, and pharmaceutically acceptable salts and prodrugs thereof.

Accordingly, the present invention provides compounds having formula IIa or IIb:

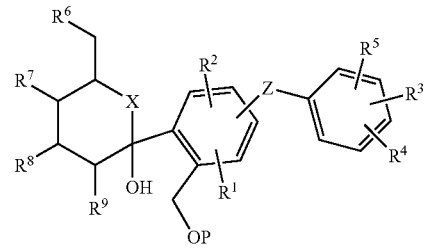

IIa

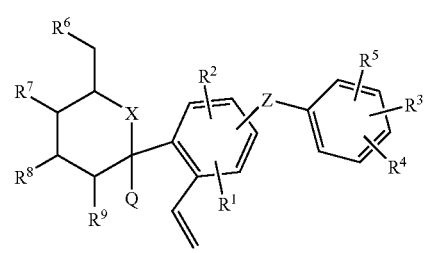

IIb wherein Q is selected from hydroxy, a protected hydroxy group, and $C_2$-$C_5$ alkenyl; P is a hydrogen or hydroxy-protecting group. The remaining groups X, Z, $R^1$, $R^2$, $R^3$, $R^4$, $R^5$, $R^6$, $R^7$, $R^8$ and $R^9$ have the meanings provided above for formula I. Similarly, preferred groups with respect to formula I are preferred for formula II as well.

Methods of preparing the intermediate compounds of formula IIa comprise:

(a) contacting a halo aryl intermediate of formula IIIa:

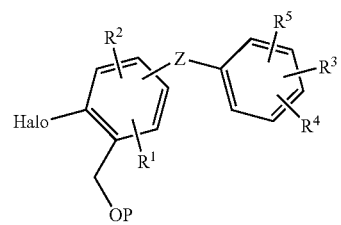

IIIa wherein P is a hydrogen or hydroxy-protecting group; and the remaining groups have the meanings provided above for formula I, with a compound having the formula:

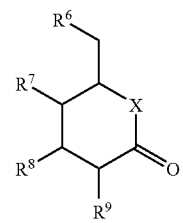

wherein X, $R^6$, $R^7$, $R^8$ and $R^9$ have the meanings provided for formula I, under conditions sufficient to form a compound of formula IIa:

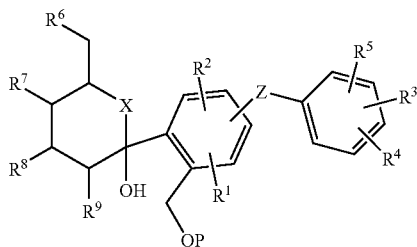

wherein the groups have the meanings provided above. Additional steps to convert compounds of formula IIa to compounds of formula I are described below in the Schemes and in the Examples.

Figure 9:
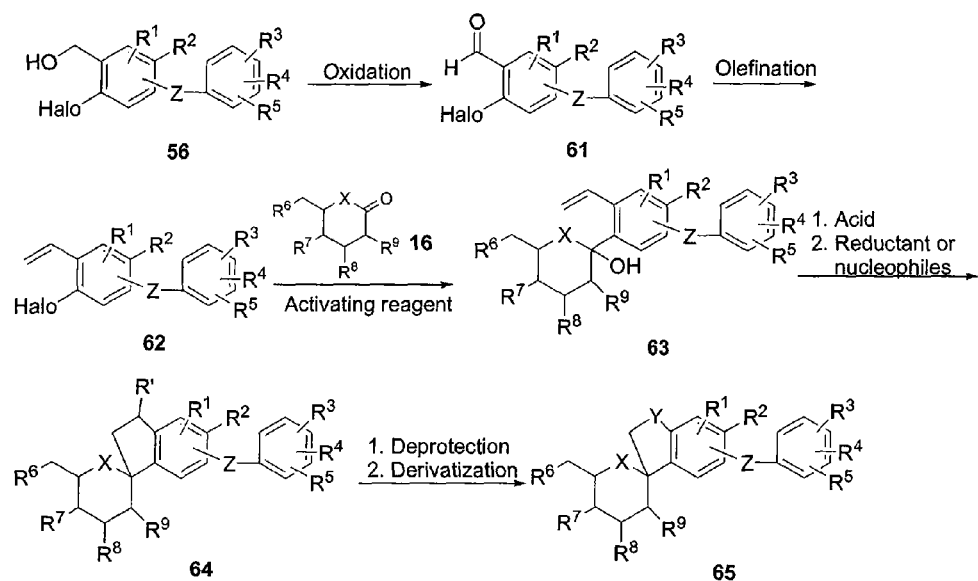
FIG. 9 is the general synthesis method of Scheme IX for the preparation of compounds of the invention.
Figure 10:
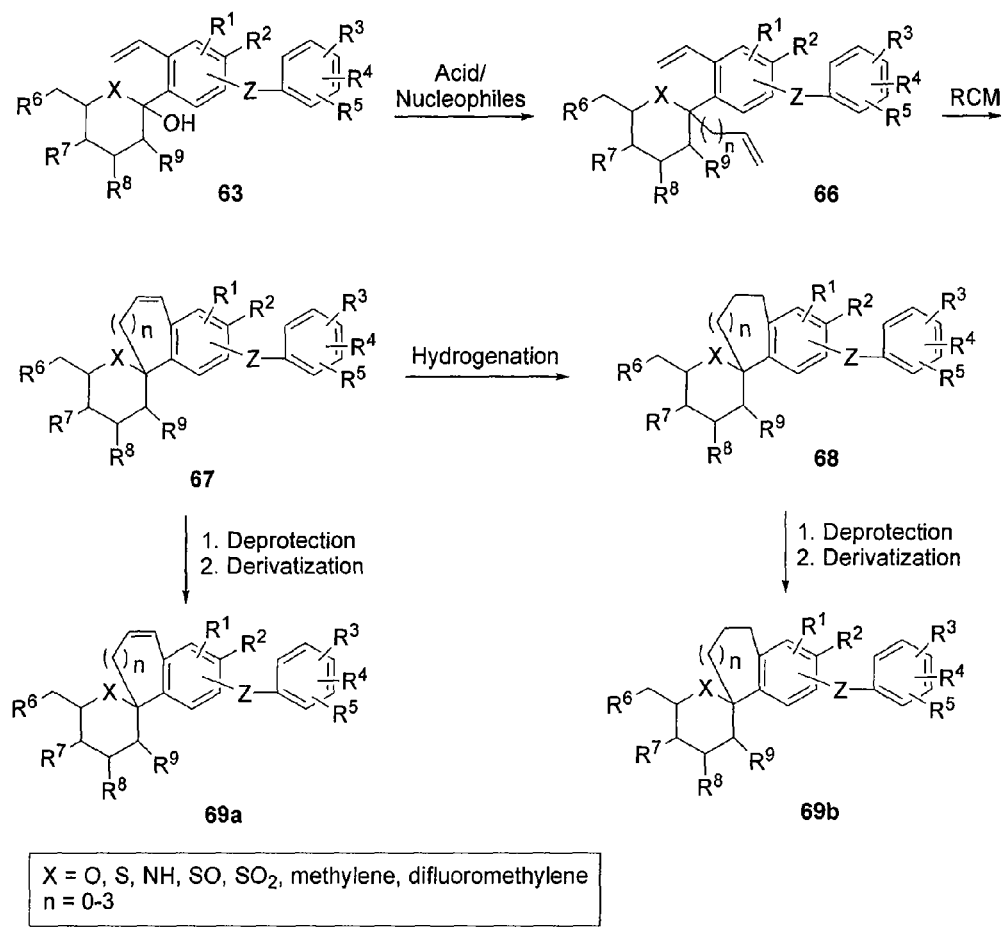
FIG. 10 is the general synthesis method of Scheme X for the preparation of compounds of the invention.

In a similar manner, the present invention provides methods of preparing compounds of formula IIb, that are based on the synthetic protocol outlined in FIG. 9, Scheme IX (conversion of 62 to 63) and in FIG. 10, Scheme X (conversion of 63 to 66). Additional steps to convert compounds of formula IIb to compounds of formula I are also described in the attached Schemes and constitute another aspect of the present invention.

Such processes are outlined in the following general preparative methods depicted in Schemes I-XIII, with more detailed particular examples being presented below in the experimental section describing the working examples. By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: 18-Crown-6,1,4,7,10,13,16-hexaoxacyclooctadecane; AgOTf, silver trifluoromethanesulfonate (silver triflate); n-BuLi, n-butyllithium; s-BuLi, s-butyllithium; t-BuLi, t-butyllithium; t-BuOK, potassium tert-butoxide; $CD_3OD$, methanol-$d_4$; $CDCl_3$, chloroform-d; $CH_2Cl_2$, methylene chloride; $CH_3CN$, acetonitrile; DAST, (diethylamino)sulfur trifluoride; DIPEA, N,N-diisopropylethylamine; DMAP, 4-dimethylaminopyridine; DMF, N,N-dimethylformamide; DMSO, dimethylsulfoxide; EDCI, 1-(3-dimethylaminopropyl)-3-ethylcarbodiimide hydrochloride; Et, ethyl; $Et_3N$, triethylamine; EtOAc (or AcOEt), ethyl acetate; EtOH, ethanol; h, hour; $H_2$, hydrogen gas; HATU, 2-(7-aza-1H-benzotriazole-1-yl)-1,1,3,3-tetramethyluronium hexafluorophosphate; HCl, hydrochloric acid; $^1H$ NMR, proton nuclear magnetic resonance; $H_2SO_4$, sulfuric acid; HPLC, high performance liquid chromatography; $K_2CO_3$, potassium carbonate; KOH, potassium hydroxide; LC-MS, liquid chromatography-mass spectroscopy; Me, methyl; MeOH, methanol; min, minute; MOMCl, methoxymethylchloride; MOMO, methoxymethoxy; MS ESI, mass spectroscopy with electrospray ionization; MsOH, methanesulfonic acid; NaH, sodium hydride; $NaHCO_3$, sodium bicarbonate; NaOH, sodium hydroxide; $Na_2SO_4$, sodium sulfate; NBS, N-bromosuccinimide; NCS, N-chlorosuccinimide; $NH_3$, ammonia; NIS, N-iodosuccinimide; Pd/C, palladium on carbon; PDC, pyridinium dichromate; $Pd(PPh_3)_4$, tetrakis(triphenylphosphine)palladium(0); $R_f$, retention factor; $SnCl_2$, tin (II) chloride; TBAF, tetrabutylammonium fluoride; TBAI, tetrabutylammonium iodide; TBDMS, t-butyldimethylsilyl; $Tf_2O$, trifluoromethanesulfonic anhydride; TFA, trifluoroacetic acid; THF, tetrahydrofuran; TLC, thin layer chromatography; TMS, trimethylsilyl; TMSCN, trimethylsilyl cyamide; TsOH, toluenesulfonic acid.

General Synthesis Method of Scheme I

Figure 1B:
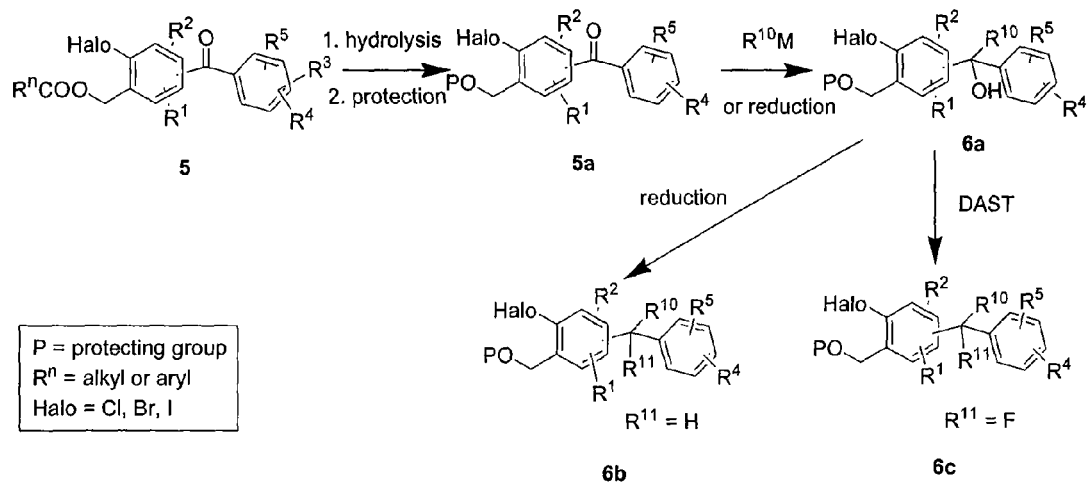
FIG. 1B is the general synthesis method of Scheme I, Part B, for the preparation of compounds of the invention.
Figure 1C:
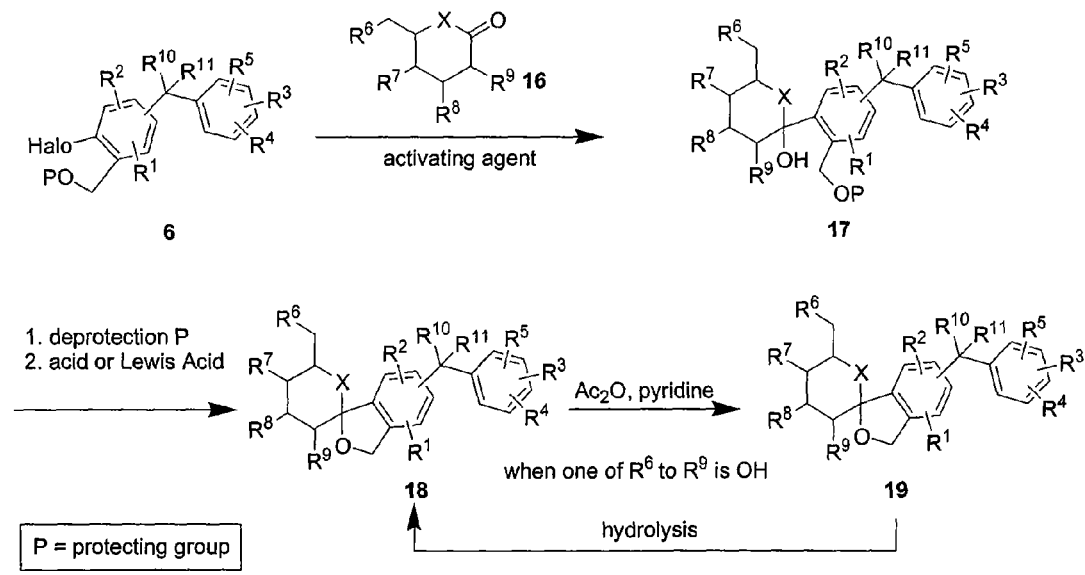
FIG. 1C is the general synthesis method of Scheme I, Part C, for the preparation of compounds of the invention.

Inventive compounds of formula 18 can be conveniently prepared according to the reaction sequences as shown in Scheme I, Parts A-C (FIGS. 1A-C).

As shown in Scheme I, Part A (FIG. 1A), acid 1, either commercially available or prepared according to conventional methods known to those of skill in the art, is converted to acid chloride 2 by an acylation agent such as oxalyl chloride, $SOCl_2$, $POCl_3$ or the like. Intermediate 2 is reacted with substituted benzene 3 under conditions aided by Lewis acid, such as $AlCl_3$ or $AlBr_3$, to provide ketone 4. Halogenation of ketone 4 with halogenation reagent, such as NCS, NBS or NIS, is followed by replacement of benzylic halogen with carboxylic acid salt, such as NaOAc, KOAc, sodium or potassium salt of benzoic acid, etc., to provide intermediate 5.

Alternatively, acid 1 can be halogenated with NCS, NBS or NIS, and then reacted with a carboxylic acid salt, such as NaOAc, KOAc, sodium or potassium salt of benzoic acid, or the like, to furnish intermediate 7. Intermediate 5 can be obtained by treatment of substituted benzene 3 under Friedel-Craft acylation conditions with intermediate 8, which is obtained by treatment of intermediate 7 with an acylation agent such as oxalyl chloride, $SOCl_2$, $POCl_3$ or the like.

Alternatively, acid 7 can be transferred to intermediate 8a such as a Weinreb amide. Intermediate 5 can be obtained by treatment of 8a with an organometallic reagent 14.

Alternatively, intermediate 5 can also be obtained by treatment of acyl chloride 11 with intermediate 10, which is prepared from substituted toluene 9 by halogenation with NCS, NBS or NIS, and then treatment of the product with a carboxylic acid salt such as NaOAc, KOAc, sodium or potassium salt of benzoic acid, or the like.

The ketone group of intermediate 5 is selectively reduced to methylene with a reducing agent such as $Et_3SiH$ in the present of a Lewis acid such as $BF_3.Et_2O$ or TFA. Hydrolysis of the product under basic conditions, such as LiOH, NaOH, KOH or NaOMe, and protection with a protecting group such as TMS or TBDMS provides compound 6.

Intermediate 6 can also be obtained by reduction of alcohol 15, which is the adduct of organometallic compound 14 and aldehyde 13. Aldehyde 13 can be easily prepared starting from substituted toluene 9 by formylation, halogenation of the benzylic methyl with NCS, NBS, NIS, or the like and treatment of the resulting product with a carboxylic acid salt such as NaOAc, KOAc, sodium or potassium salt of benzoic acid etc.

As shown in Scheme I, Part B (FIG. 1B), intermediate 5 can also be transferred to 5a by hydrolysis and protection. By treatment with an organometallic reagent such as Grignard reagent or lithium reagent, intermediate 6a ($R^{10}=C_1-C_3$ alkyl) can be obtained. Intermediate 6a can be transferred to 6c ($R^{11}=F$) via DAST reagent or to 6b ($R^{11}=H$) by reduction.

As shown in Scheme I, Part C (FIG. 1C), treatment of 6 with an activating agent such as n-BuLi, s-BuLi and t-BuLi, or Mg at appropriate temperature in a solvent such as THF, followed by addition to intermediate 16 provides intermediate 17. Finally, deprotection of protecting group P and cyclization under acidic conditions, such as TsOH, MsOH or a Lewis acid such as $BF_3.Et_2O$, provides inventive compounds 18. Compound 18 can be further purified by acetylation, recrystallization and hydrolysis.

General Synthesis Method of Scheme II

Figure 2:
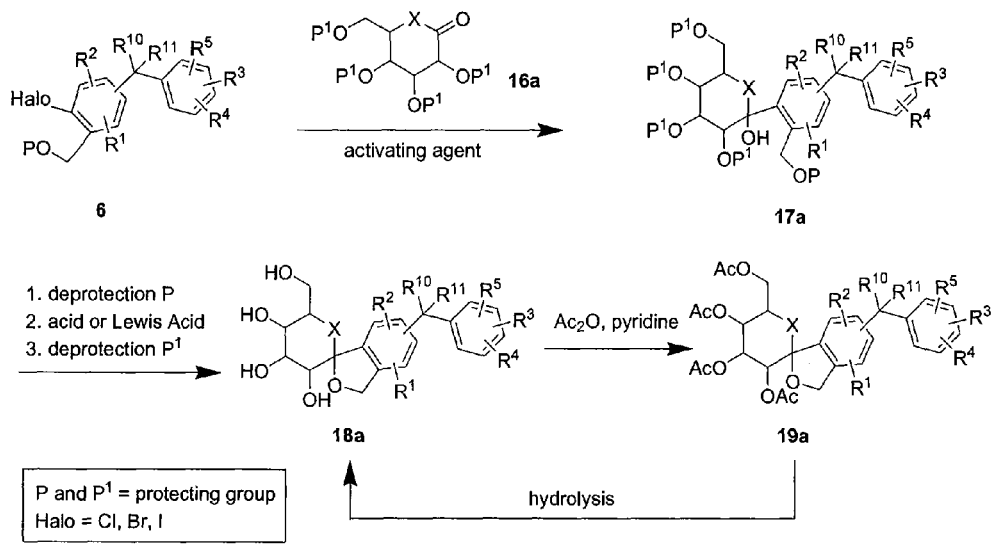
FIG. 2 is the general synthesis method of Scheme II for the preparation of compounds of the invention.

Inventive compounds of formula 18a can be conveniently prepared according to a reaction sequence as shown in Scheme II (FIG. 2).

As shown in Scheme II, treatment of 6 with an activating agent, such as n-BuLi, s-BuLi and t-BuLi, or Mg, at appropriate temperature in a solvent such as THF, followed by addition to intermediate 16a provides intermediate 17a. Finally, deprotection of protecting group P and cyclization under acidic conditions such as TsOH, MsOH or a Lewis acid such as $BF_3.Et_2O$, followed by deprotection of protecting group $P^1$, provide inventive compounds 18a, which can be further purified by recrystallization of its acetate 19a, and then hydrolysis of 19a back to 18a.

General Synthesis Method of Scheme III

Figure 3:
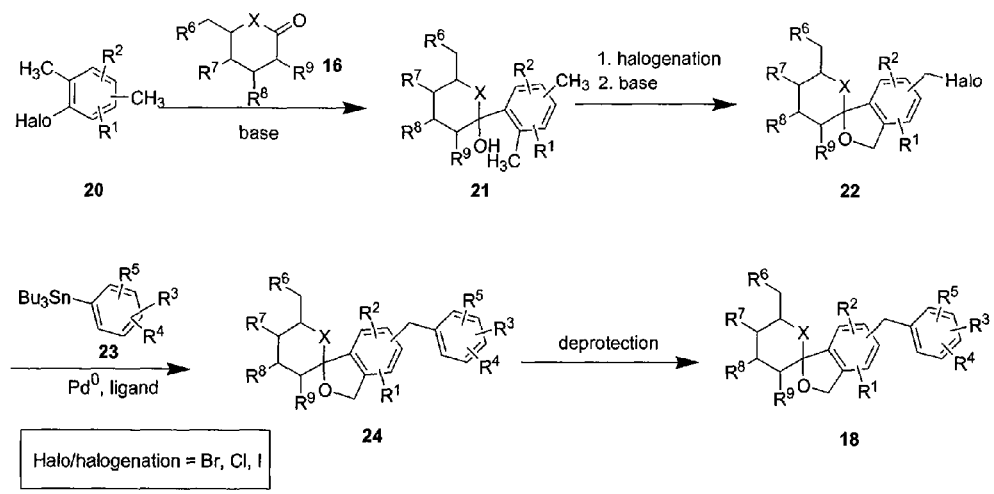
FIG. 3 is the general synthesis method of Scheme III for the preparation of compounds of the invention.

Inventive compounds of formula 18 can also be prepared according to a reaction sequence as shown in Scheme III (FIG. 3).

As shown in Scheme III, treatment of intermediate 20 with an activating agent such as n-BuLi, s-BuLi and t-BuLi, or Mg at appropriate temperature in a solvent such as THF, followed by addition to intermediate 16 provides intermediate 21. Halogenation of 21 with NCS, NBS or NIS and treatment of the corresponding product with a base provide intermediate 22. Intermediate 24 can be obtained by Stille coupling of 22 with tin reagent 23. Finally, deprotection of 24 (wherein one of $R^6$ to $R^9$ has a protecting group) provides inventive compounds 18.

General Synthesis Method of Scheme IV

Figure 4:
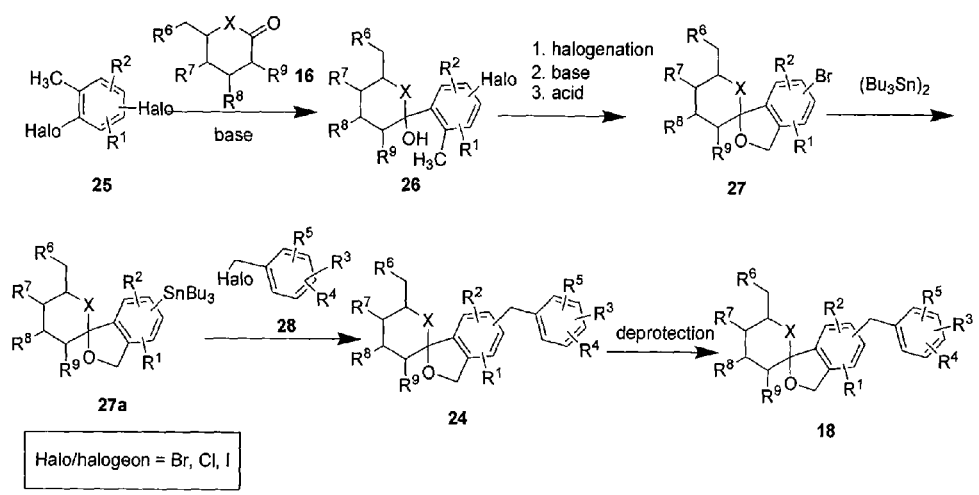
FIG. 4 is the general synthesis method of Scheme IV for the preparation of compounds of the invention.

Inventive compounds of formula 18 can also be prepared according to a reaction sequence as shown in Scheme IV (FIG. 4).

As shown in Scheme IV, treatment of compound 25 with an activating agent, such as n-BuLi, s-BuLi and t-BuLi, or Mg, at appropriate temperature in a solvent such as THF, followed by addition to intermediate 16 provides intermediate 26. Halogenation of 26 with NCS, NBS or NIS followed by treatment with a base and then with an acid or Lewis acid provides intermediate 27. Intermediate 27a can be obtained by treatment of 27 with $(Bu_3Sn)_2$ and a catalyst such as $Pd(Ph_3P)_4$ in a solvent such as toluene. Intermediate 24 can be obtained by Stille coupling of 27a with 28. Finally, deprotection of 24 (wherein one of $R^6$ to $R^9$ has a protecting group) provides inventive compounds 18.

General Synthesis Method of Scheme V

Figure 5:
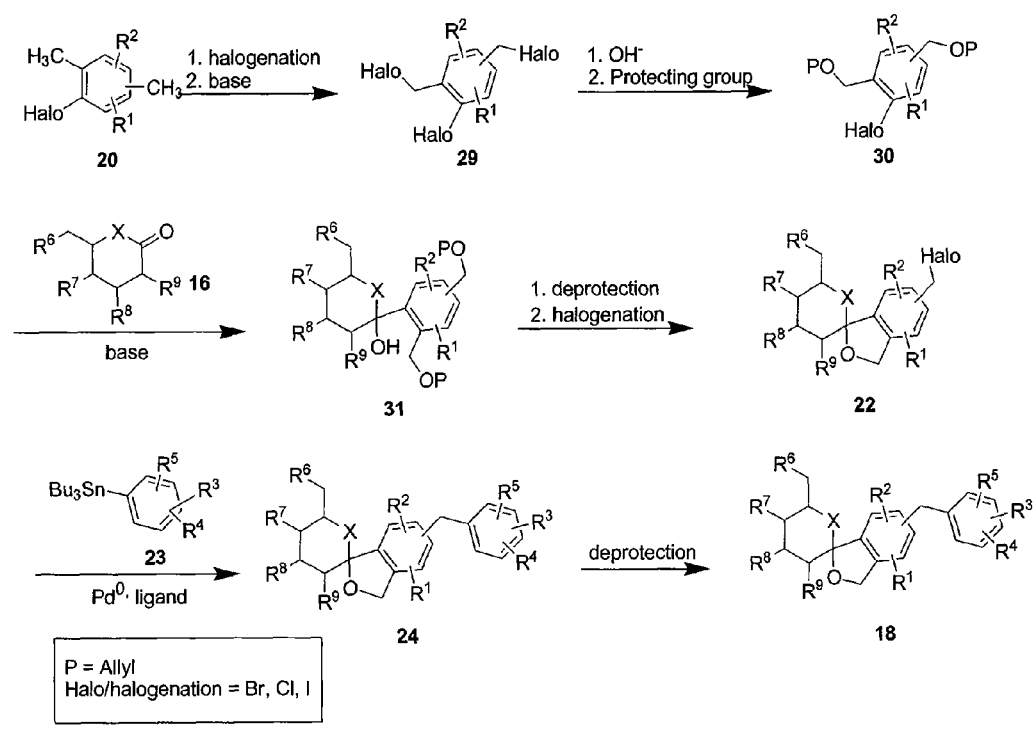
FIG. 5 is the general synthesis method of Scheme V for the preparation of compounds of the invention.

Inventive compounds of formula 18 can also be prepared according to a reaction sequence as shown in Scheme V (FIG. 5).

As shown in Scheme V, halogenation of compound 20 with NCS, NBS or NIS provides intermediate 29. Hydroxylation of 29 followed by protection provides intermediate 30. Treatment of 30 with an activating agent, such as n-BuLi, s-BuLi and t-BuLi, or Mg, at appropriate temperature in a solvent such as THF, followed by addition to intermediate 16 provides intermediate 31. Selective deprotection of protection group P, followed by replacement of hydroxyl with halogen under conditions employing reagents such as $Ph_3P/CBr_4$ or $CCl_4$ provides intermediate 22. Intermediate 24 can be obtained by Stille coupling of 22 with 23. Finally, deprotection of 24 (wherein one of $R^6$ to $R^9$ has a protecting group) provides inventive compounds 18.

General Synthesis Method of Scheme VI

Figure 6:
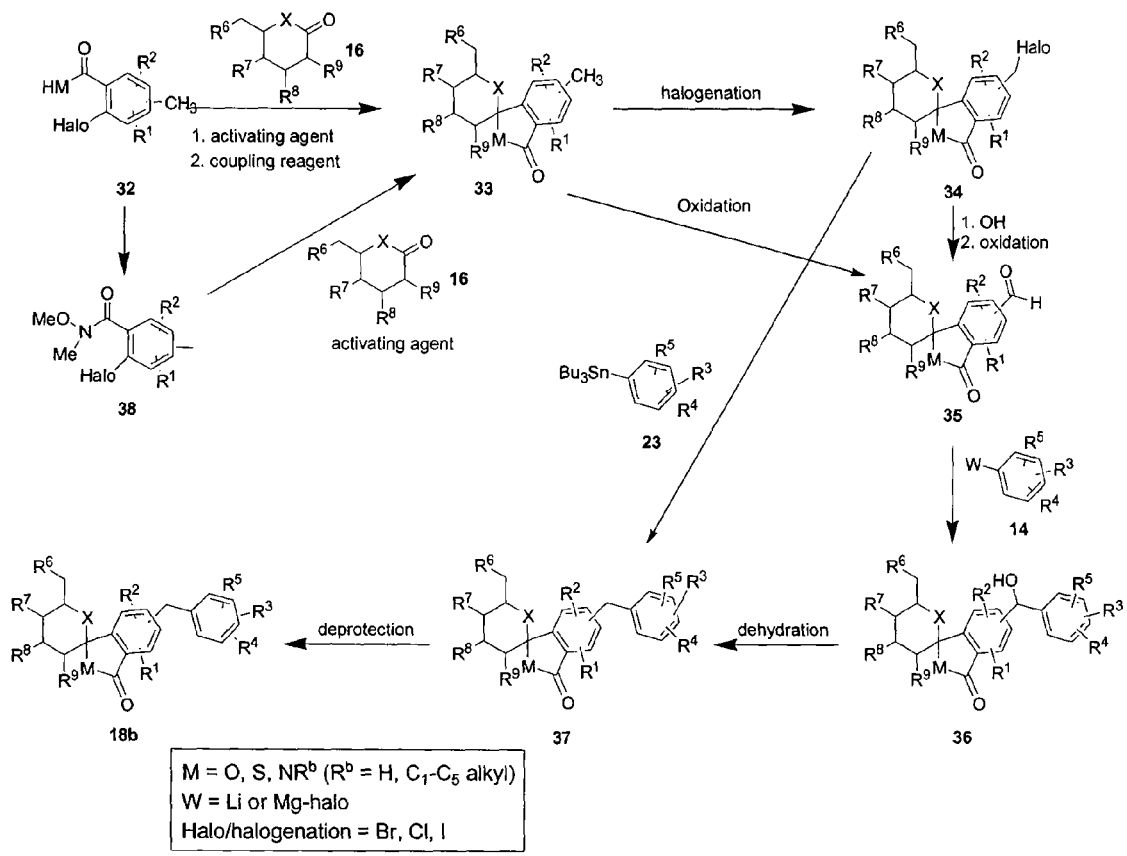
FIG. 6 is the general synthesis method of Scheme VI for the preparation of compounds of the invention.

Inventive compounds of formula 18b in which M is O, S or $NR^b$ (wherein $R^b$ represents hydrogen or $C_1-C_5$ alkyl) can also be prepared according to a reaction sequence as shown in Scheme VI (FIG. 6).

As shown in Scheme VI, treatment of compound 32 with an activating agent, such as n-BuLi, s-BuLi and t-BuLi, or Mg, at appropriate temperature in a solvent such as THF, followed by addition to intermediate 16, and then by treatment with a coupling reagent to provide intermediate 33. Alternatively, 33 can also be prepared by the addition of amide 38 to 16. Halogenation of 33 with NCS, NBS or NIS provides intermediate 34. Inventive compounds 18b can be obtained by Stille coupling of 34 with reagent 23 followed by deprotection. Alternatively, 34 can be converted to 35 by direct oxidation or hydroxylation and then oxidation. By treatment of 35 with an organometallic reagent 14, intermediate 36 can be obtained. Finally, inventive compounds 18b can be obtained by dehydration of 36 followed by deprotection.

General Synthesis Method of Scheme VII

Figure 7:
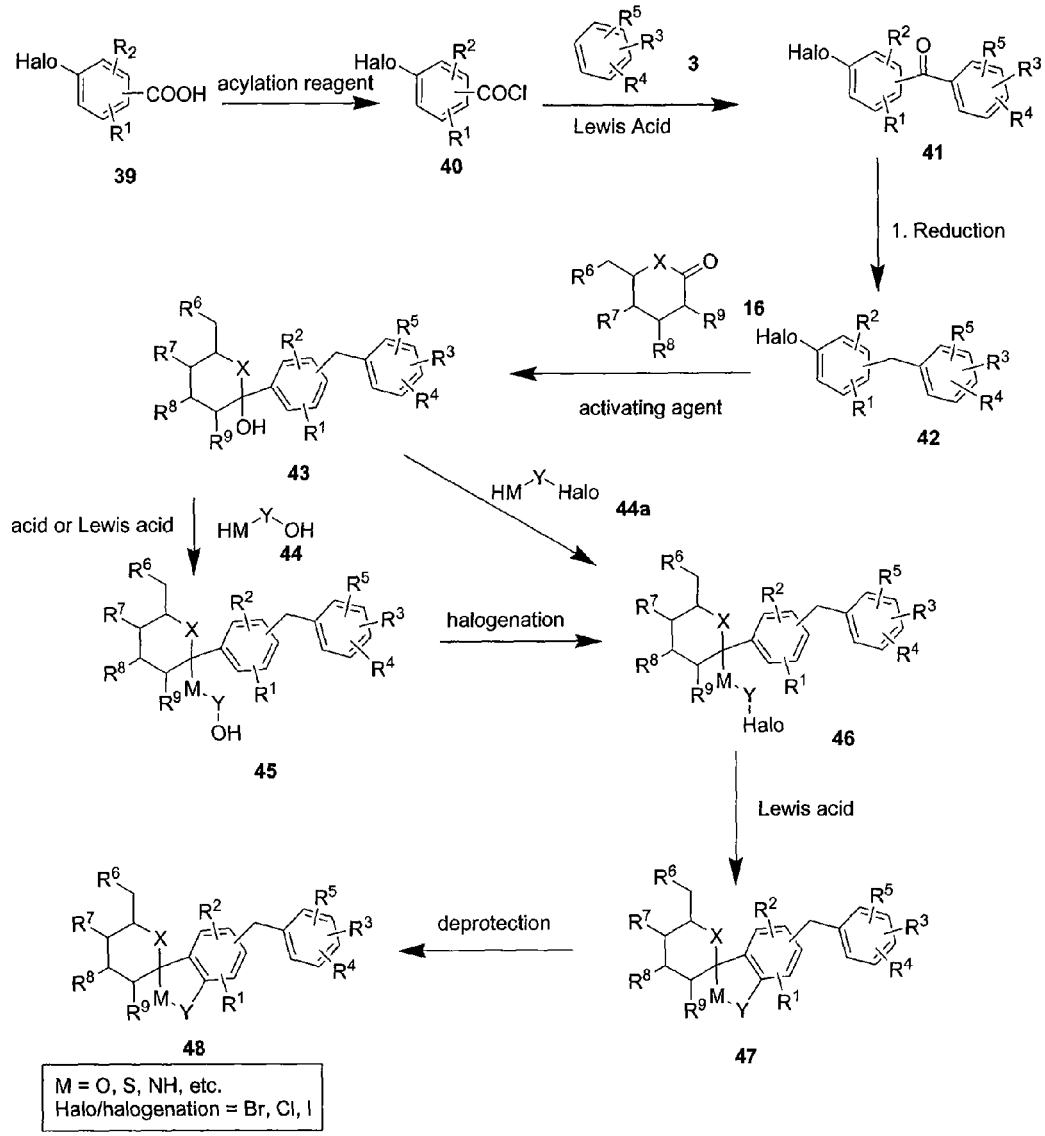
FIG. 7 is the general synthesis method of Scheme VII for the preparation of compounds of the invention.

Inventive compounds of formula 48 in which M is O, S, NH and others as defined in Formula I can be conveniently prepared according to a reaction sequence as shown in Scheme VII (FIG. 7).

As shown in Scheme VII, acid 39, either commercially available or prepared according to standard literature methods, is converted to acid chloride 40 by acylation agent such as oxalyl chloride, $SOCl_2$ or $POCl_3$, etc. Acid chloride 40 is reacted with substituted benzene 3 under Lewis acid condition such as $AlCl_3$ or $AlBr_3$ to provide ketone 41. The ketone group of intermediate 41 is selectively reduced to methylene with a reducing agent such as $Et_3SiH$ in the presence of a Lewis acid such as $BF_3.Et_2O$ or TFA. Treatment of 42 with an activating agent such as n-BuLi, s-BuLi and t-BuLi, or Mg at appropriate temperature in a solvent such as THF, followed by addition to intermediate 16 provides intermediate 43. Intermediate 46 can be obtained by treatment of 43 with 44a under acid or Lewis acid conditions. Alternatively, 46 can also be prepared via intermediate 45. Under Friedel-Craft reaction conditions, 46 is cyclized to form intermediate 47, which can be deprotected to provide invention compound 48.

General Synthesis Method of Scheme VIII

Figure 8:
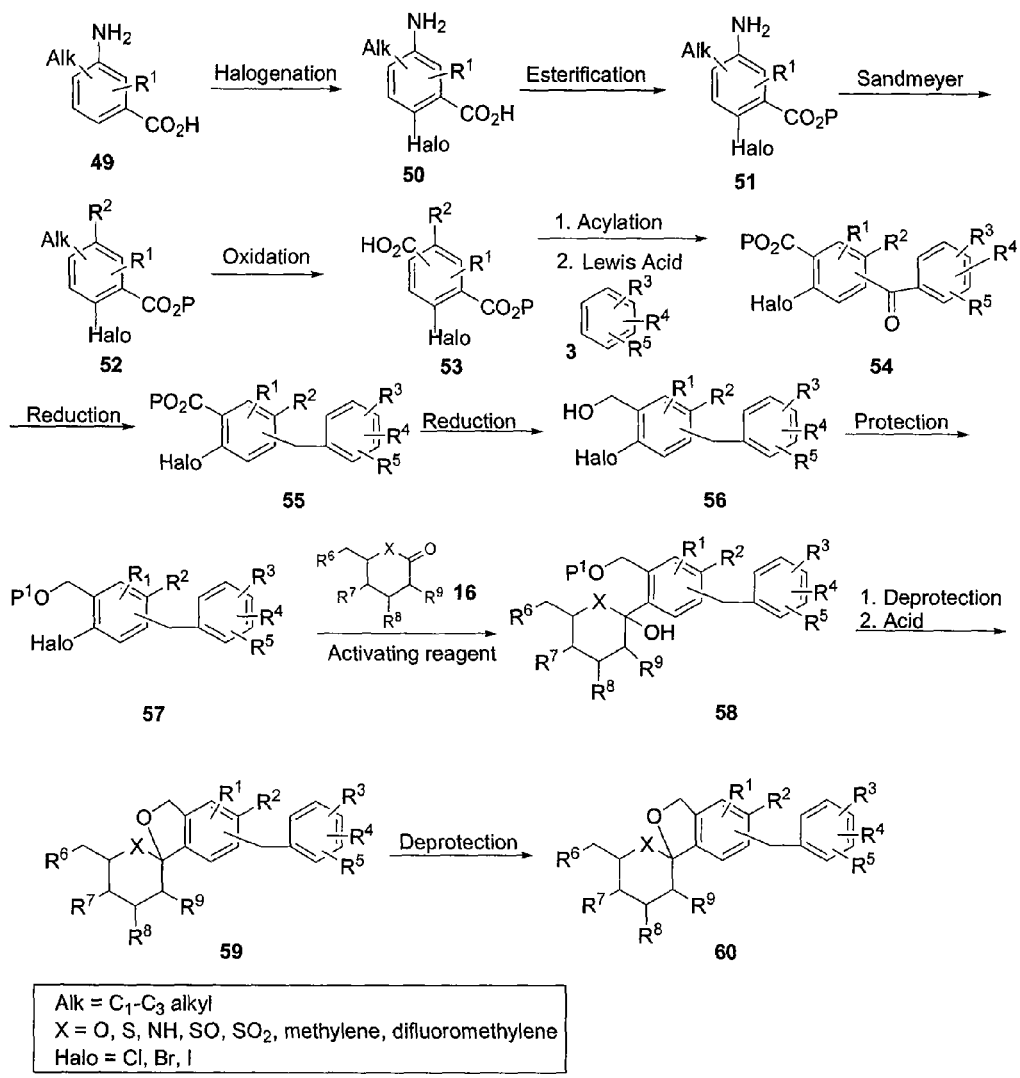
FIG. 8 is the general synthesis method of Scheme VIII for the preparation of compounds of the invention.

Inventive compounds of formula 60 can also be conveniently prepared according to a reaction sequence as shown in Scheme VIII (FIG. 8).

As shown in Scheme VIII, the meso-amino benzoic acid 49 is halogenated by NBS or other reagent to afford intermediate 50, which is then converted to its corresponding ester 51 using standard esterification procedures, such as refluxing with $H_2SO_4$/MeOH or $SOCl_2$/MeOH. Using Sandmeyer reaction conditions, ester 51 is converted to compound 52. Oxidation of ester 52 with $CrO_3$, $K_2CrO_4$ or $KMnO_4$ produces benzoic acid 53. After treatment with an acylation reagent, such as $(COCl)_2$ or $SOCl_2$, acid 53 reacts with substituted aromatic ring 3 in the presence of a Lewis acid, such as $FeCl_3$ or $AlCl_3$, to give diphenylketone 54. Ketone 54 is reduced with reductant, such as $Et_3SiH$, catalyzed by Lewis acid, such as TFA or $BF_3.Et_2O$, to give ester 55. Further reduction of ester 55 affords alcohol 56. The free alcohol is then protected with alkylsilyl or ether and treated with activating reagent, such as n-BuLi or t-BuOK, followed by condensation with protected lactone 16 to give adduct 58. Deprotecting the benzyl alcohol and treatment of the resulting compound with acid, such as TFA, $MeSO_3H$ or $BF_3.Et_2O$, gives intermediate 59, which is deprotected and further derivatized to generate the invention compounds of formula 60.

General Synthesis Method of Scheme IX

Inventive compounds of formula 65 can also be conveniently prepared according to a reaction sequence as shown in Scheme IX (FIG. 9).

As shown in Scheme IX, the benzylic alcohol 56 is oxidized to aldehyde 61 under Swern or Dess-Martin conditions, or with another oxidant such as PDC. Aldehyde 61 is then converted to the corresponding olefin 62 using Wittig or HWE reaction or other olefination reagents such as Tebbe's reagent. Olefin 62 is treated with activating reagent such as n-BuLi or t-BuOK, and condensed with protected lactone 16 to give adduct 63, which is allowed to react with reducing reagent such as $Et_3SiH$ or organometallic nucleophiles such as allyl-TMS in the presence of acid such as TFA or $BF_3.Et_2O$. The resulting spiro compound 64 is deprotected and further derivatized to form compound 65.

General Synthesis Method of Scheme X

Inventive compounds of formulas 69a and 69b can also be conveniently prepared according to a reaction sequence as shown in Scheme X (FIG. 10).

As shown in Scheme X, intermediate 63 is allowed to react with organometallic nucleophiles, such as allyl-TMS or vinyl-MgBr, to give olefin 66, which is treated with a ring closure metathesis (RCM) catalyst, such as Grubbs reagent, to yield spiro olefin 67. Olefin 67 is then deprotected and derivatized to yield product 69a. Alternatively, reduction of olefin 67 by hydrogenation gives product 68, and deprotection and further derivatization yields compound 69b.

General Synthesis Method of Scheme XI

Figure 11:
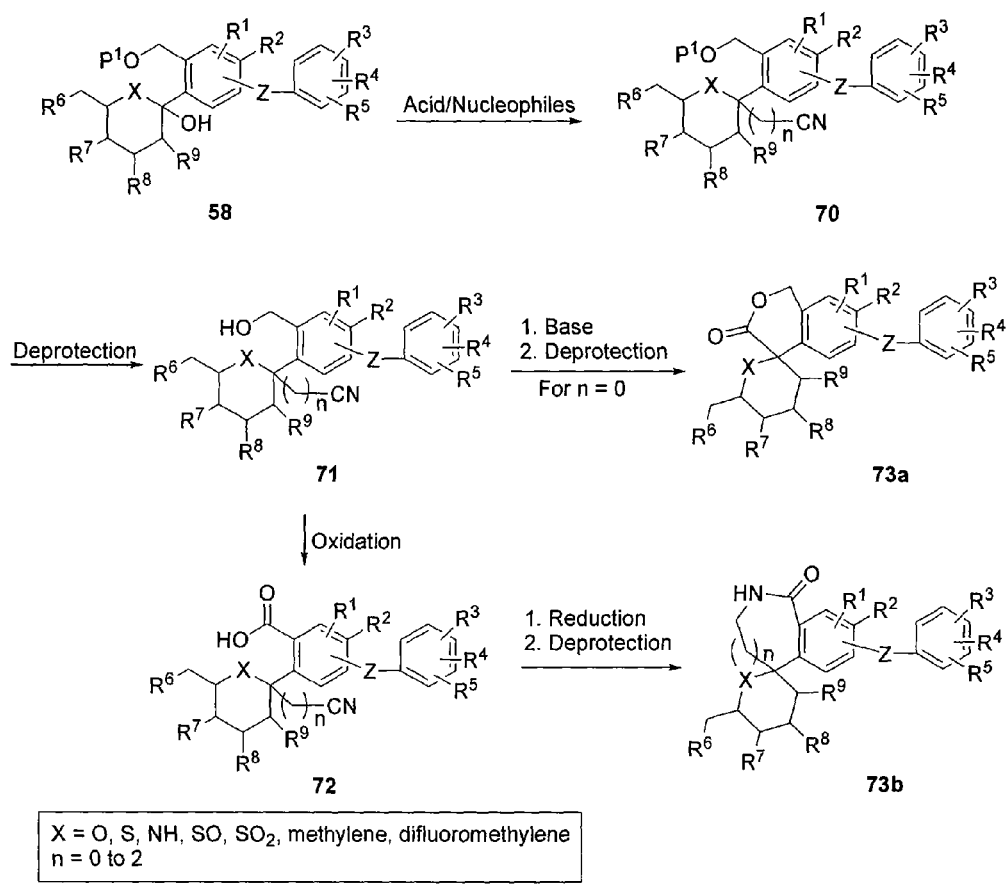
FIG. 11 is the general synthesis method of Scheme XI for the preparation of compounds of the invention.

Inventive compounds of formulas 73a and 73b can also be conveniently prepared according to a reaction sequence as shown in Scheme XI (FIG. 11).

As shown in Scheme XI, adduct 58 is allowed to react with organometallic nucleophiles, such as allyl-TMS, vinyl-MgBr or TMSCN, to generate intermediate 70, which is deprotected to form the free alcohol 71. The resulting benzyl alcohol 71 is then treated with base such as NaOMe or t-BuOK followed by deprotection to yield spiro compound 73a. Alternatively, alcohol 71 is oxidized to give acid 72. The cyano on compound 72 is then reduced to generate the corresponding amine, which reacts with the adjacent acid to form the cyclized amide. The amide is then deprotected and further derivatized to afford inventive compound 73b.

General Synthesis Method of Scheme XII

Figure 12:
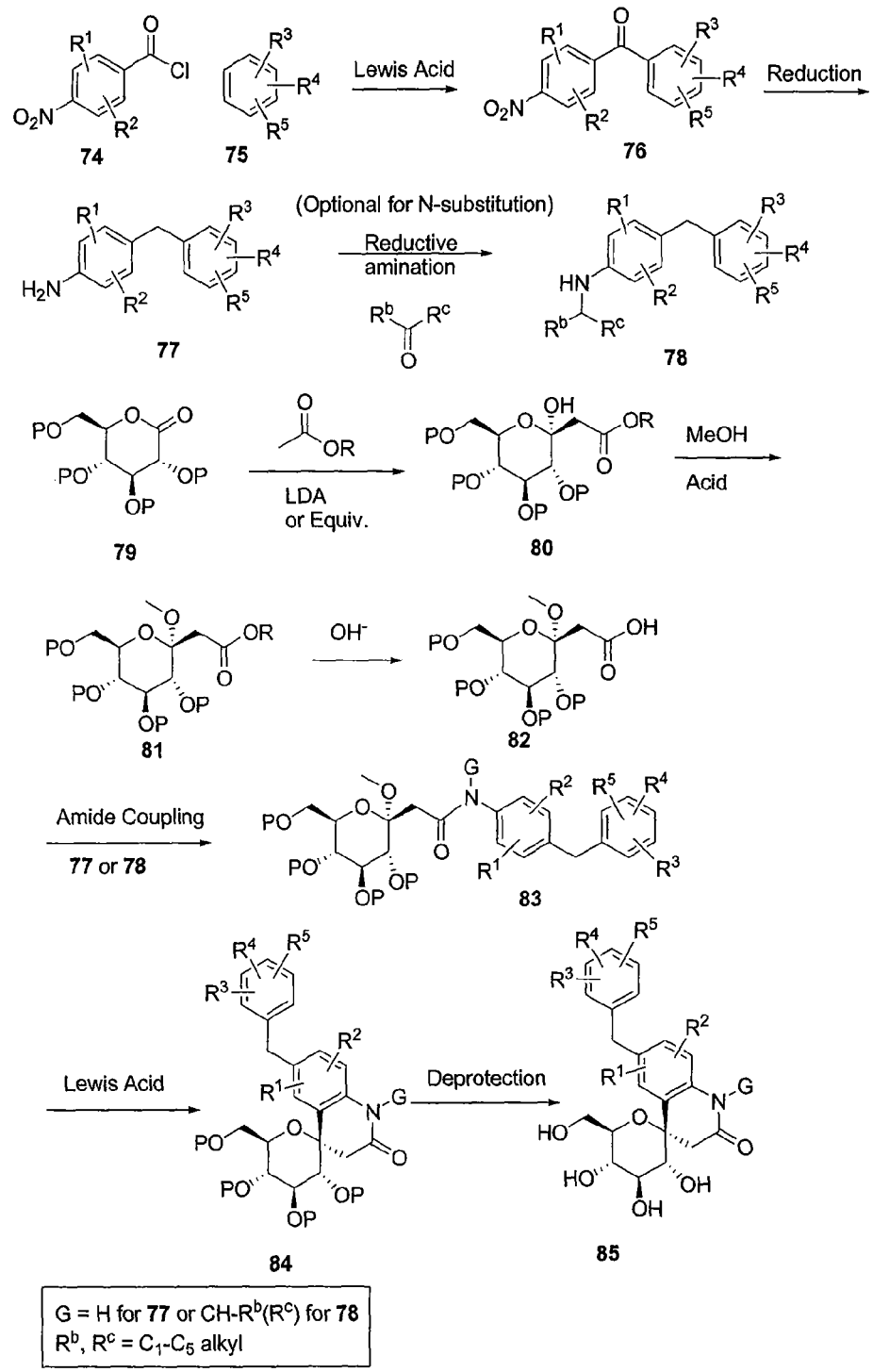
FIG. 12 is the general synthesis method of Scheme XII for the preparation of compounds of the invention.

Inventive compounds of formula 85 can also be conveniently prepared according to a reaction sequence as shown in Scheme XII (FIG. 12).

As shown in Scheme XII, nitrobenzoyl chloride 74 is coupled with aryl 75 using a Lewis acid, typically $AlCl_3$ or the like, to give benzophenone product 76. Reduction of the ketone of 76 can be accomplished by triethylsilane and an appropriate protic or Lewis acid, typically trifluoroacitic acid or borontrifluoroetherate, followed by nitro reduction, typically done using tin chloride, to give aniline 77. At this point reductive amination may be done to alkylate the aniline using standard conditions, preferably sodium triacetoxyborohydride with catalytic acetic acid or titanium tetraisopropoxide, to give aniline 78. Suitably protected gluconolactone 79 (typically alkyl or silyl ether protection, preferably benzyl) is treated with the lithium anion of an alkyl acetate, typically methyl acetate, generated from an appropriate lithium base, typically lithium diisopropylamide, to generate lactol 80. Acid catalyzed methyl glycoside formation, typically with a sulfonic acid or sulfonic acid resin and trimethylorthoformate in methanol, gives 81. Hydrolysis of the ester using a metal hydroxide, typically lithium hydroxide, gives carboxylic acid 82. Amide coupling of acid 82 with either 77 or 78, using standard coupling reagents, preferably HATU, gives amide 83. At this juncture protecting group P may be changed to an ester protecting group, if desired, by standard de-protection conditions, typically a palladium catalyst and hydrogen for benzyl ether protection, followed by esterification under standard conditions, preferably acetic anhydride and pyridine for acetate protection. Cyclization initiated by a Lewis acid, typically borontrifluoroetherate, gives 84. Deprotection of the remaining hydroxyls under standard conditions, preferably sodium methoxide in methanol for acetate protection or palladium catalyst and hydrogen for benzyl protection, gives 85.

General Synthesis Method of Scheme XIII

Figure 13:
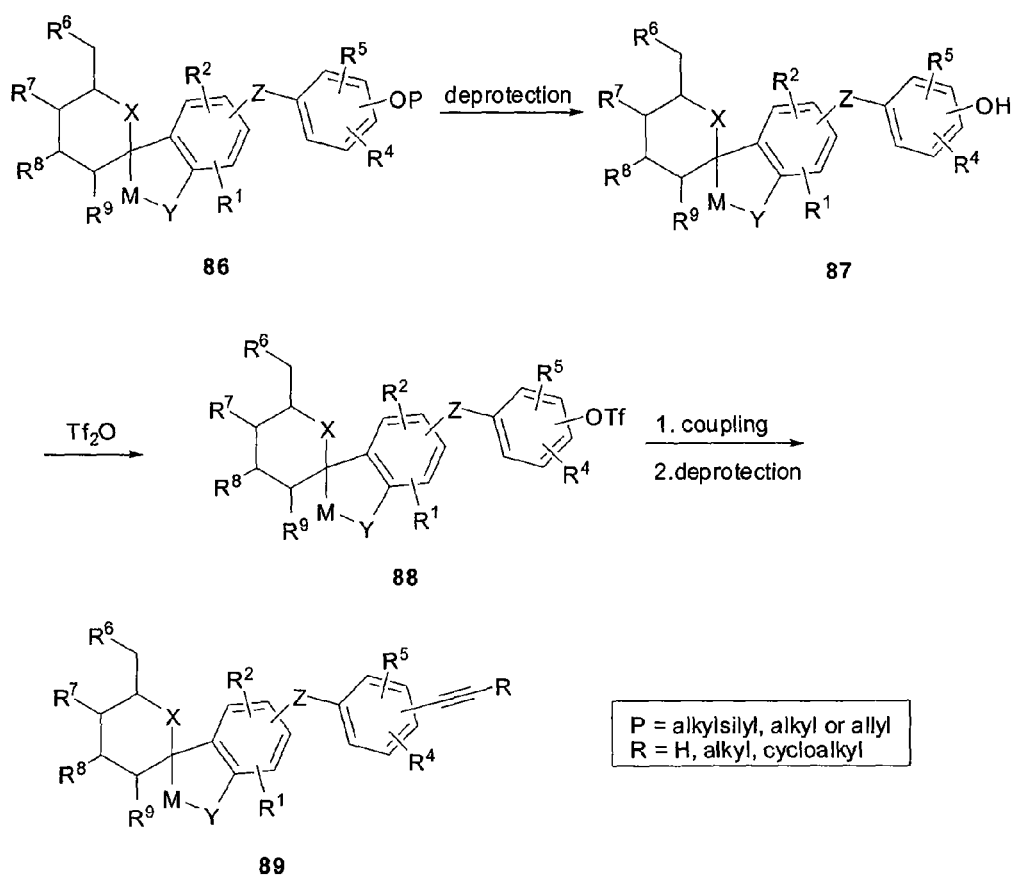
FIG. 13 is the general synthesis method of Scheme XIII for the preparation of compounds of the invention.

Inventive compounds of formula 89 can be conveniently prepared according to a reaction sequence as shown in Scheme XIII (FIG. 13).

As shown in Scheme XIII, starting from the intermediate 86, which is synthesized using the methods that are described in Schemes I to XII, spiro phenol 87 is obtained by removal of the protecting groups P after reaction with TBAF (when P is alkylsilyl), $BBr_3$ (when P is alkyl), or $Pd(OAc)_2$ in the presence of NaOAc and HOAc (when P is allyl). The phenol 87 is then esterified with $Tf_2O$ (triflic anhydride) to give the coupling precursor 88, which is coupled with terminal alkyne with the catalysis of Pd catalysts, such as $Pd(PPh_3)_4$. Deprotection of the alkyne and/or other protecting group on the resulting compound leads to the desired spiro derivative 89.

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., Current Science, Vol. 88, No. 2, 25 Jan. 2005, pp. 241-249, and the like), glycogen phosphorylase inhibitors (such as N,N-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., Current Science, Vol. 88, No. 2, 25 Jan. 2005, pp. 241-249, and the like), incretin mimetics (such as exenatide and the like), glucagon receptor antagonists (such as BAY-27-9955, N,N-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation endproducts (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as, 1-(m-chlorophenyl)piperazine (m-CPP), mirtazapine, APD-356 (lorcaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, *J. Med. Chem.* 2006, 49:4023-4034)), beta-3 adrenergic receptor agonists (such as L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, A-71378, FPL-15849, GI-248573, GW-7178, GI-181771, GW-7854, GW-5823, and the like), antidepressant/acetylcholinesterase inhibitor combinations (such as venlafaxine/rivastigmine, sertraline/galanthamine and the like), lipase inhibitors (such as orlistat, ATL-962 and the like), gamma-aminobutyric acid receptor antagonists (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant and the like), and melanin-concentrating hormone receptor antagonists (such as GlaxoSmithKline 856464, SNAP-7941, T-226296 and the like).

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetamide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretamide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and antiplatelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the Cambridge-Soft Struct=Name algorithm as implemented in ChemDraw Ultra version 10.0 The structures of compounds synthesized in the examples below were confirmed using the following procedures:

(1) Gas chromatography-mass spectra with electrospray ionization (MS ESI) were obtained with an Agilent 5973N mass spectrometer equipped with an Agilent 6890 gas chromatograph with an HP-5 MS column (0.25 µm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 µm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% B to 90% in 8 min at a flow rate of 1.0 mL/min is used with a final hold at 90% B of 7 min. Total run time is 15 min.

(3) Routine one-dimensional NMR spectroscopy is performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$-d3, 3.30 ppm for $CD_3OD$-d4, 5.32 ppm for $CD_2Cl_2$-d4 and 7.26 ppm for $CDCl_3$-d for $^1H$ spectra.

Example 1

Summary Procedure for the Synthesis of Compound G

Figure 14:
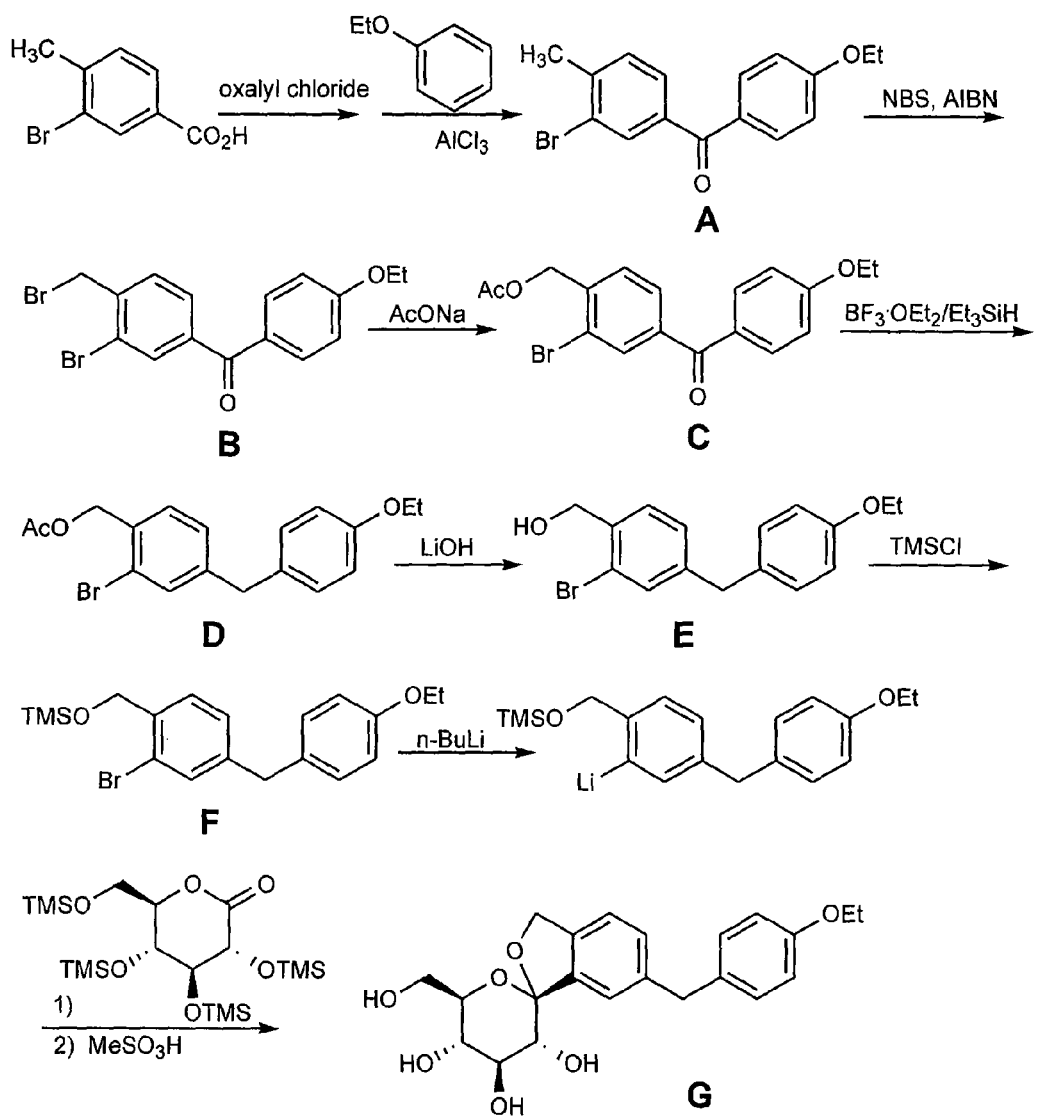
FIG. 14 is the summary procedure for the synthesis of compound G of the invention.

The synthesis of compound G within the invention is outlined in FIG. 14, with the details of the individual steps given below.

Preparation of (3-bromo-4-methylphenyl)(4-ethoxyphenyl)methanone (Intermediate A)

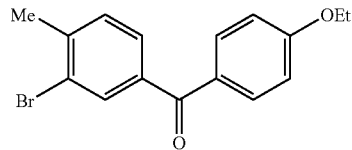

To a stirred solution of 3-bromo-4-methylbenzoic acid (1.2 g, 4.74 mmol) and oxalyl chloride (0.7 mL, 8.16 mmol) in 8 mL of $CH_2Cl_2$ was added 50 µL of DMF. The reaction mixture was stirred overnight prior to removal of the volatiles under reduced pressure using a rotary evaporator. The crude 3-bromo-4-methylbenzoyl chloride was dissolved in 10 mL of $CH_2Cl_2$ and then cooled to −5° C. prior to adding phenetole (0.63 mL, 5.0 mmol). $AlCl_3$ (0.945 g, 7.1 mmol) was added via a solid addition funnel over 30 min. After the mixture was stirred at 5° C. for 2 h, the reaction was quenched by pouring over ice. Subsequently, the suspension was diluted with water and extracted 3× with $CH_2Cl_2$. The combined organic layers were washed 2× with 1 M HCl, once with $H_2O$, 2× with 1 M NaOH, and 2× with brine prior to drying over $Na_2SO_4$. Recrystallization 2× from absolute EtOH provided 1.13 g of (3-bromo-4-methylphenyl)(4-ethoxyphenyl)methanone. $^1H$ NMR ($CDCl_3$, 300 MHz): δ 7.93 (d, J=1.6 Hz, 1H), 7.79 (d, J=8.8 Hz, 2H), 7.60 (dd, J=1.6, 8.0 Hz, 1H), 7.33 (d, J=8.0 Hz, 1H), 6.95 (d, J=8.8 Hz, 2H), 4.12 (q, J=7.0 Hz, 2H), 2.48 (s, 3H), 1.46 (t, J=7.0 Hz, 3H); MS ESI (m/z) 319 (M+1)$^+$, calc. 318.

Preparation of (3-bromo-4-(bromomethyl)phenyl)(4-ethoxyphenyl)methanone (Intermediate B)

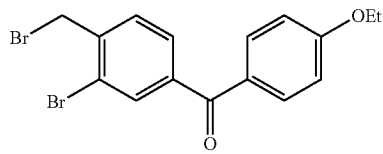

To a stirred solution of (3-bromo-4-methylphenyl)(4-ethoxyphenyl)methanone (0.864 g, 2.71 mmol) in $CCl_4$ (3.5 mL) were added N-bromosuccimide (0.506 g, 2.84 mmol) and 2,2'-azobis(isobutyronitrile) (20 mg, 0.14 mmol). After being vigorously stirred under reflux at an external temperature of 100° C. for 110 min, additional N-bromosuccimide (0.1 g, 0.56 mmol) and 2,2'-azobis(isobutyronitrile) (20 mg, 0.14 mmol) were added. The mixture was stirred for another 30 min, then cooled with ice-water. The resulting precipitates were collected by filtration and washed with ethyl acetate. The filtrate was washed 3× with 5% citric acid, and dried over $Na_2SO_4$. Concentration under reduced pressure gave the crude product which was recrystallized from ethyl acetate to yield 0.54 g of the title compound. $^1$H NMR (CDCl$_3$, 300 MHz): δ 7.96 (s, 1H), 7.80 (d, J=8.8 Hz, 2H), 7.66 (d, J=8.0 Hz, 1H), 7.56 (d, J=8.0 Hz, 1H), 6.96 (d, J=8.4 Hz, 2H), 4.64 (s, 2H), 4.13 (q, J=6.8 Hz, 2H), 1.46 (t, J=6.8 Hz, 3H); MS ESI (m/z) 397 (M+1)$^+$, calc. 396.

Preparation of 2-bromo-4-(4-ethoxybenzoyl)benzyl acetate (Intermediate C)

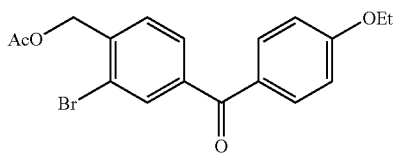

To a solution of (3-bromo-4-(bromomethyl)phenyl)(4-ethoxyphenyl)methanone (0.456 g, 1.15 mmol) in 15 mL of DMF was added sodium acetate (0.188 g, 2.29 mmol). After being stirred for 2.5 h at 68° C., the mixture was diluted with 15 mL of $H_2O$ and extracted 3× with ethyl acetate. The combined organic layers were washed once with saturated $NH_4Cl$, once with saturated brine and dried over $Na_2SO_4$. Concentration under reduced pressure gave 0.412 g of the crude product, which was used in the next step without further purification. $^1$H NMR (CDCl$_3$, 300 MHz): δ 7.95 (d, J=1.2 Hz, 1H), 7.79 (d, J=8.8 Hz, 2H), 7.68 (dd, J=1.2, 8.0 Hz, 1H), 7.50 (d, J=8.0 Hz, 1H), 6.95 (d, J=8.8 Hz, 2H), 5.25 (s, 2H), 4.12 (q, J=7.0 Hz, 2H), 1.46 (t, J=7.0 Hz, 3H); MS ESI (m/z) 377 (M+1)$^+$, calc. 376.

Preparation of 2-bromo-4-(4-ethoxybenzyl)benzyl acetate (Intermediate D)

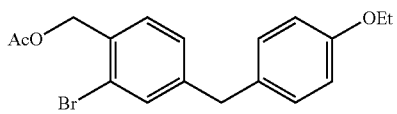

To a stirred solution of 2-bromo-4-(4-ethoxybenzoyl)benzyl acetate (0.41 g, 1.09 mmol) and Et$_3$SiH (0.44 µL, 2.76 mmoL) in 1,2-dichloroethane/MeCN (2.5 mL, 1:2), was added dropwise BF$_3$.Et$_2$O (0.21 mL, 1.66 mmol). The reaction was complete after stirring for about 17 h at 25° C. Upon cooling, the reaction was quenched with 0.5 mL of 28.5% NaOH aqueous solution. The aqueous layer was extracted 2× with $CH_2Cl_2$, the combined organic layers were washed once with 2M KOH, 2× with $H_2O$ containing 10% brine and 2× with brine prior to drying over $Na_2SO_4$. After removal of the volatiles, the residue was purified by silica gel column (10:1 petroleum ether/ethyl acetate) to yield 0.24 g of title compound. $^1$H NMR (CDCl$_3$, 300 MHz): δ 7.39 (s, 1H), 7.20 (d, J=8.0 Hz, 1H), 7.12 (d, J=8.0 Hz, 1H), 7.07 (d, J=8.4 Hz, 2H), 6.83 (d, J=8.4 Hz, 2H), 5.15 (s, 2H), 4.01 (q, J=7.0 Hz, 2H), 3.88 (s, 2H), 2.12 (s, 3H), 1.40 (t, J=7.0 Hz, 3H); MS ESI (m/z) 380 (M+NH$_4$)$^+$, calc. 362.

Preparation of (2-bromo-4-(4-ethoxybenzyl)phenyl)methanol (Intermediate E)

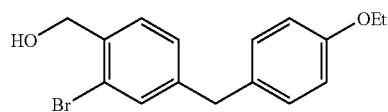

To a solution of 2-bromo-4-(4-ethoxybenzyl)benzyl acetate (0.215 g, 0.59 mmol) in 10 mL of THF/MeOH/H$_2$O (2:3:1) was added LiOH.H$_2$O (0.051 g, 1.21 mmol). After the reaction mixture was stirred at 25° C. for 3 hours, the volatiles were removed using a rotary evaporator. The residue was dissolved in EtOAc, washed once with brine and dried over $Na_2SO_4$. The volatiles were removed using a rotary evaporator to yield 0.175 g of the title compound, which was used in the next step without further purification. $^1$H NMR (CDCl$_3$, 300 MHz): δ 7.38-7.36 (m, 2H), 7.13 (d, J=7.6 Hz, 1H), 7.07 (d, J=8.8 Hz, 2H), 6.83 (d, J=8.4 Hz, 2H), 4.71 (s, 2H), 4.01 (q, J=7.2 Hz, 2H), 3.88 (s, 2H), 1.92 (bs, 1H), 1.40 (t, J=7.2 Hz, 3H); MS ESI (m/z) 320 [M$^+$], calc. 320.

Preparation of (2-bromo-4-(4-ethoxybenzyl)benzyloxy)trimethylsilane (Intermediate F)

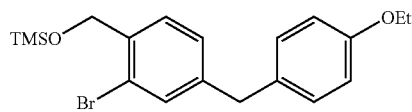

To a cooled solution (−10° C.) of (2-bromo-4-(4-ethoxybenzyl)phenyl)methanol (0.137 g, 0.43 mmol) and N-methylmorpholine (0.1 mL, 0.9 mmol) in 2 mL of THF under N$_2$, was added dropwise trimethylsilyl chloride. One hour later, the reaction was allowed to stir at 35° C. for 5 h and then stirred at 20° C. overnight. After dilution with AcOEt, the mixture was cooled to 0° C. prior to cautiously adding H$_2$O at a rate such that the temperature did not exceed 10° C. The organic layer was separated and washed with aqueous KH$_2$PO$_4$, H$_2$O, and brine. The volatiles were removed using a rotary evaporator to yield the title compound, which was used in the next step without further purification.

Preparation of (1S,3'R,4'S,5'S,6'R)-6-(4-ethoxybenzyl)-6'-(hydroxymethyl)-3',4',5',6'-tetrahydro-3H-spiro[isobenzofuran-1,2'-pyran]-3',4',5'-triol (Compound G)

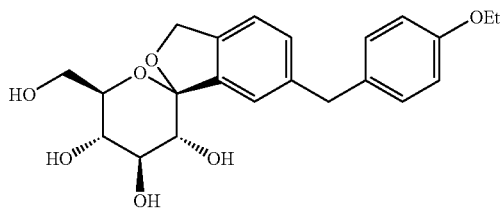

To a stirred solution of (2-bromo-4-(4-ethoxybenzyl)benzyloxy)trimethyl-silane (40 mg, 0.1 mmol) in 1 mL of anhydrous THF/toluene (1:2) at −78° C. was added dropwise n-BuLi (0.1 mL of 1.6 M in hexane) while the temperature remained below −70° C. The mixture was then stirred for another 30 min at the same temperature. To the reaction mixture was added dropwise a solution of 2,3,4,6-tetra-O-trimethylsilyl-β-D-glucolactone (56 mg, 0.12 mmol) in 0.5 mL of toluene at −78° C. The solution was stirred for 5 h at the same temperature prior to quenching by addition of a solution of methanesulfonic acid (34 mg, 0.35 mmol) in 0.5 mL of THF. The reaction was stirred for 21 h as the temperature rose to 25° C. and then quenched with saturated $NaHCO_3$. The organic phase was separated, washed with brine and dried over $Na_2SO_4$. The volatiles were removed under vacuum using a rotary evaporator. The residue was purified by preparative TLC to yield 15 mg of the title compound. $^1$H NMR ($CDCl_3$, 300 MHz): δ 7.14 (s, 1H), 7.00 (d, J=8.0 Hz, 1H), 6.94 (d, J=7.6 Hz, 1H), 6.90 (d, J=8.4 Hz, 2H), 6.64 (d, J=8.3 Hz, 2H), 4.92 (d, J=12.4 Hz, 1H), 4.83 (d, J=12.4 Hz, 1H), 3.94-3.57 (m, 10H), 1.25 (t, J=7.0 Hz, 3H); MS ESI (m/z) 425 (M+Na)$^+$, calc. 402.

Example 2

Preparation of (1S,3'R,4'S,5'S,6'R)-5-chloro-6-(4-ethoxybenzyl)-6'-(hydroxymethyl)-3',4',5',6'-tetrahydro-3H-spiro[isobenzofuran-1,2'-pyran]-3',4',5'-triol (Compound H)

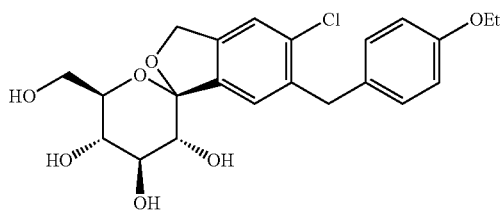

Compound H was prepared by a method analogous to that described in Example 1 by using (2-bromo-5-chloro-4-(4-ethoxybenzyl)benzyloxy)trimethylsilane (which was prepared as described for intermediate F). $^1$H NMR ($CD_3OD$): δ 7.35 (s, 1H), 7.23 (s, 1H), 7.11~7.09 (d, J=8.8 Hz, 2H), 6.82~6.80 (d, J=8.8 Hz, 2H), 5.14~5.05 (dd, J=24.6, 12.8 Hz, 2H), 4.09~4.01 (dd, J=13.6 Hz, 2H), 4.02~3.96 (m, 2H), 3.82~3.59 (m, 5H), 3.45~3.40 (m, 1H), 1.37~1.34 (t, 3H).

Example 3

Preparation of (1S,3'R,4'S,5'S,6'R)-6-(4-ethylbenzyl)-6'-(hydroxymethyl)-3',4',5',6'-tetrahydro-3H-spiro[isobenzofuran-1,2'-pyran]-3',4',5'-triol (Compound J)

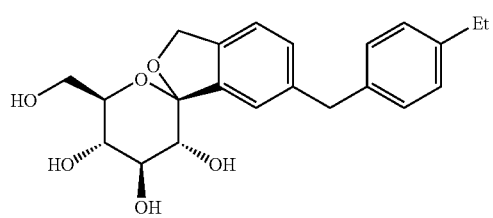

Compound J is prepared by a method analogous to that described in Example 1 by using (2-bromo-4-(4-ethylbenzyl)benzyloxy)trimethylsilane (which is prepared as described for intermediate F).

Example 4

Summary Procedure for the Synthesis of Compound K

Figure 15:
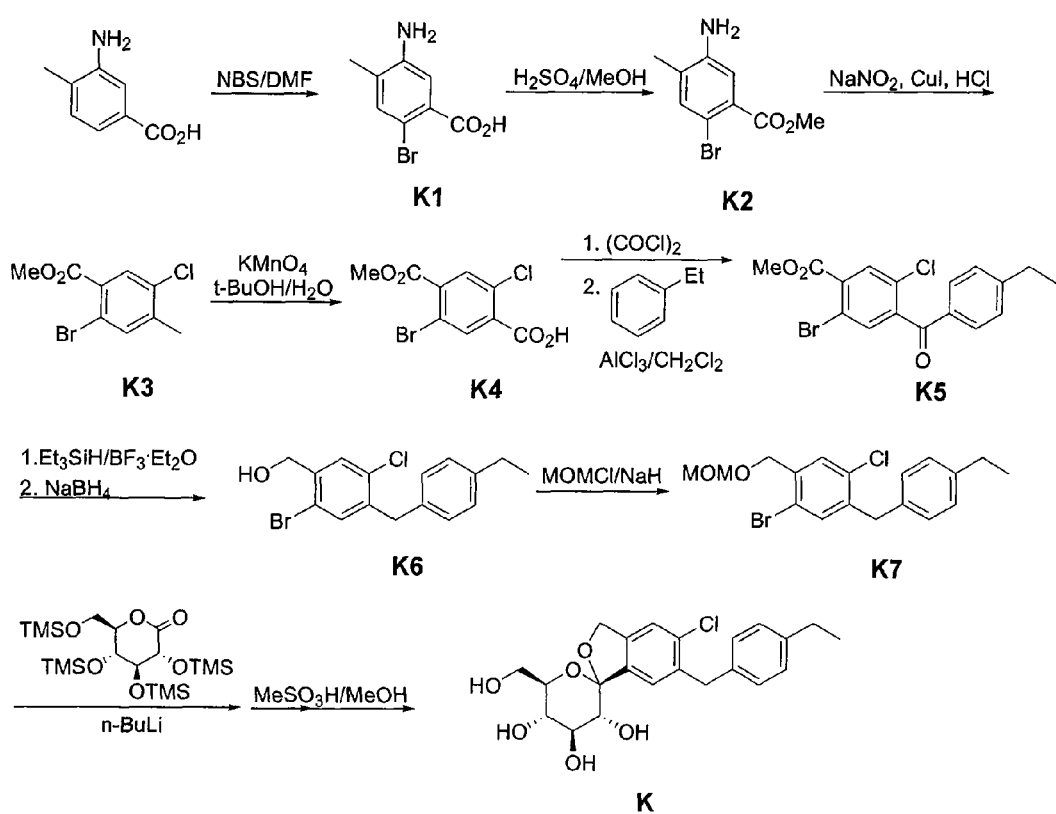
FIG. 15 is the summary procedure for the synthesis of compound K of the invention.

The synthesis of compound K within the invention is outlined in FIG. 15, with the details of the individual steps given below.

Preparation of 5-amino-2-bromo-4-methylbenzoic acid (Intermediate K1)

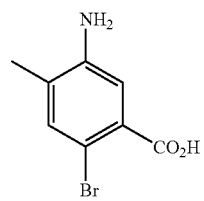

To a cooled solution (5° C.) of 3-amino-4-methylbenzoic acid (412.2 g, 2.72 mole) in DMF (2.2 L) was added N-bromosuccinimide (495.1 g, 2.78 mole) in small portions at such a rate that the reaction mixture temperature was kept below 15° C. After being stirred for one hour, the reaction mixture was poured onto ice water (1.2 L) with stirring. The solid that formed was filtered, and the filter cake was washed with ice water (3×2 L) and then dried at 60° C. to give a pink solid. Yield: 546 g (87%). $^1$H NMR (DMSO-d6, 300 MHz): δ 7.20 (s, 1H), 7.04 (s, 1H), 2.05 (s, 3H).

Preparation of methyl 5-amino-2-bromo-4-methylbenzoate (Intermediate K2)

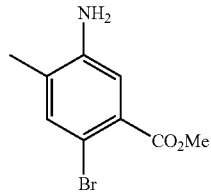

To a cooled solution (5° C.) of 5-amino-2-bromo-4-methylbenzoic acid (100.0 g, 0.434 mmol) in anhydrous methanol (1.6 L) was added dropwise thionyl chloride (112.4 g). The reaction mixture was refluxed and monitored by TLC. After refluxing for 6 h, the reaction was complete. The reaction solution was concentrated under reduced pressure. The residue was diluted with ice water (1.2 L) and neutralized with 5% of $NaHCO_3$ to pH 7.5. The aqueous layer was extracted with ethyl acetate (3×600 mL), and the combined organic layers were washed with brine (2×500 mL), and dried over anhydrous $Na_2SO_4$. Concentration under reduced pressure provided the title compound as a pale solid. Yield: 99%. $^1$H NMR (DMSO-$d_6$, 300 MHz): δ 7.25 (s, 1H), 7.14 (s, 1H), 3.30 (s, 3H), 2.15 (s, 3H); MS ESI (m/z) 244 [M+1]$^+$, calc. 243.

Preparation of methyl 2-bromo-5-chloro-4-methylbenzoate (Intermediate K3)

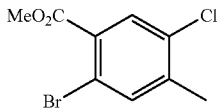

To a cooled solution (15° C.) of methyl 5-amino-2-bromo-4-methylbenzoate (122 g, 0.5 mol) in 1,4-dioxane (633 mL), was added conc. hydrochloric acid (550 mL). After the mixture was cooled to 5° C., a solution of sodium nitrite (35.53 g, 0.515 mol) in 83 mL of $H_2O$ was added dropwise at such a rate that the reaction temperature was kept below 0° C. After being stirred at 0° C. for 2 hours, the reaction mixture was added slowly to a flask containing copper (I) chloride (59.4 g, 0.6 mol) and conc. hydrochloric acid (275 mL). It was stirred for 40 min, at which time TLC demonstrated that the reaction was complete. The reaction mixture was poured over ice water (2 L) and then filtered. The filter cake was dissolved in ethyl acetate (1.5 L). The organic layer was washed with brine (3×500 mL), dried over anhydrous $Na_2SO_4$. Concentration under reduced pressure provided the title compound as light yellow crystals. Yield: 120 g (92.6%). $^1$H NMR (CDCl$_3$, 300 MHz): δ 7.82 (s, 1H), 7.54 (s, 1H), 3.92 (s, 3H), 2.38 (s, 3H); MS ESI (m/z) 262 (M)$^+$, calc. 262.

Preparation of 5-bromo-2-chloro-4-(methoxycarbonyl)benzoic acid (Intermediate K4)

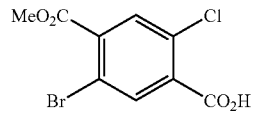

A mixture of methyl 2-bromo-5-chloro-4-methylbenzoate (39.53 g, 0.15 mol), 18-Crown-6 (3.95 g), tert-butyl alcohol (350 mL), and water (750 mL) was combined together with mechanical stirring. The reaction mixture was heated to reflux and monitored by TLC. After refluxing overnight, the reaction was cooled to 55° C. and filtered. The filter cake was washed with hot water (2×100 mL, 50° C.). The filtrate was neutralized with 18% hydrochloric acid to pH 1 and stored in refrigerator (0~5° C.) for 3 h. It was filtered, washed with ice water (2×50 mL) and petroleum ether (2×50 mL). The filter cake was dried under vacuum to give the title compound as a white crystalline. Yield: 32.1 g (73%). $^1$H NMR (DMSO-$d_6$, 300 MHz): δ 8.10 (s, 1H), 7.89 (s, 1H), 3.86 (s, 3H).

Preparation of methyl 2-bromo-5-chloro-4-(4-ethylbenzoyl)benzoate (Intermediate K5)

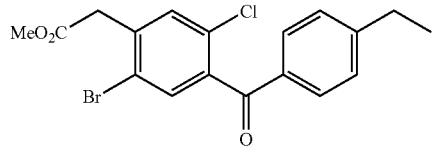

To a solution of 5-bromo-2-chloro-4-(methoxycarbonyl)benzoic acid (1.21 g, 4.15 mmol) in dry dichloromethane (22.5 mL) was added dropwise oxalyl chloride (0.43 mL, 4.96 mmol) followed by N,N-dimethylformamide (1 mL). After being stirred for 2 h at room temperature, the reaction mixture was evaporated and the residue was dissolved in dry dichloromethane (20 mL) at room temperature under argon. After cooling to −5° C., ethylbenzene (0.46 g, 4.35 mmol) was added. Then AlCl$_3$ (1.72 g, 12.8 mmol) was added portionwise and the reaction temperature was kept between −5° C. and 0° C. After being stirred at the same temperature for two hours, the reaction mixture was poured onto ice water and extracted with dichloromethane (100 mL). The combined organic layers were washed with 1 M HCl (60 mL), water (30 mL) and brine (60 mL), dried over anhydrous $Na_2SO_4$. Concentration under reduced pressure provided the title compound as a yellow solid. Yield: 1.37 g (87%). $^1$H NMR (CDCl$_3$, 300 MHz): δ 7.89 (s, 1H), 7.72 (d, J=2.0 Hz, 1H), 7.70 (d, J=2.0 Hz, 1H), 7.64 (s, 1H), 7.33 (s, 1H), 7.30 (s, 1H), 3.98 (s, 3H), 2.70 (q, J=7.8 Hz, 2H), 1.27 (t, J=7.8 Hz, 3H).

Preparation of (2-bromo-5-chloro-4-(4-ethylbenzyl)phenyl)methanol (Intermediate K6)

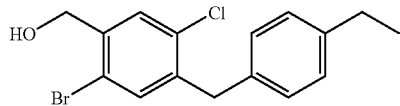

To a solution of methyl 2-bromo-5-chloro-4-(4-ethylbenzoyl)benzoate (7.64 g, 20 mmol) in 2,2,2-trifluoroacetic acid (38 mL) was added to triethylsilane (5.88 mL, 40 mmol) under argon. After it was stirred for 10 min at room temperature, trifluoromethanesulfonic acid (0.1 mL) was added. The reaction temperature was raised from 26° C. to reflux. After stirring for 2 hours, TLC (petroleum ether:ethyl acetate=6:1, $R_f$=0.7) showed the reaction was complete. The reaction mixture was evaporated and the residue was dissolved in ethyl acetate (150 mL). The organic layer was washed 2× with H$_2$O, 2× with NaHCO$_3$, and 2× with brine, dried over anhydrous Na$_2$SO$_4$. Concentration under reduced pressure provided the title compound as a white solid. Yield: 7.2 g (100%). $^1$H NMR (CDCl$_3$, 300 MHz) δ 7.85 (s, 1H), 7.44 (s, 1H), 7.17 (s, 1H), 7.14 (s, 1H), 7.10 (s, H), 7.07 (s, 1H), 4.05 (s, 2H), 3.92 (s, 3H), 2.63 (q, J=7.8 Hz, 2H), 1.24 (t, J=7.8 Hz, 3H).

Preparation of 1-bromo-4-chloro-5-(4-ethylbenzyl)-2-((methoxymethoxy)methyl)benzene (Intermediate K7)

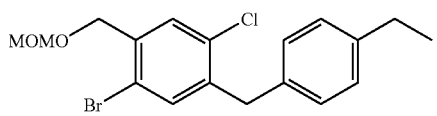

To a cooled (0° C.) solution of (2-bromo-5-chloro-4-(4-ethylbenzyl)phenyl)methanol (4.0 g, 11.8 mmol) in CH$_2$Cl$_2$ (60 mL), was added N,N-Diisopropylethylamine (DIPEA) (10.5 mL, 59.0 mmol) and MOMCl (4.5 µL, 59.0 mmol) successively. The reaction mixture was kept at 0° C. for 1 h, and then warmed to room temperature and kept at that temperature for 4 h. The reaction was quenched with H$_2$O, the organic layer was separated and the aqueous layer was extracted 2× with CH$_2$Cl$_2$. The combined organic layers were washed 1× with brine prior to drying over Na$_2$SO$_4$. The volatiles were removed using a rotary evaporator and the resulting residue was purified by a silica gel column (50:1 petroleum ether:ethyl acetate as eluent) to give 4.05 g of pure product as colorless oil. $^1$H NMR (CDCl$_3$, 300 MHz) δ 7.52 (s, 1H), 7.33 (s, 1H), 7.12 (q, 4H), 4.77 (s, 2H), 4.60 (s, 2H), 4.03 (s, 2H), 3.44 (s, 3H), 2.64 (q, J=7.5 Hz, 2H), 1.24 (t, J=7.5 Hz, 3H).

Preparation of (1S,3'R,4'S,5'S,6'R)-5-chloro-6-(4-ethylbenzyl)-6'-(hydroxymethyl)-3',4',5',6'-tetrahydro-3H-spiro[isobenzofuran-1,2'-pyran]-3',4',5'-triol (Compound K)

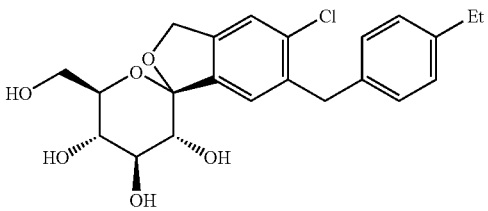

To a stirred −78° C. solution of 1-bromo-4-chloro-5-(4-ethylbenzyl)-2-((methoxymethoxy)methyl)benzene (2.9 g, 7.56 mmol) in 48 mL of 1:2 anhydrous THF/toluene under Ar, was added 3.57 mL of 2.5 M n-BuLi in hexane dropwise to insure the temperature remained below −65° C., and the mixture was stirred for 40 min at the same temperature. To the reaction mixture was added dropwise a solution of 2,3,4,6-tetra-O-trimethylsilyl-β-D-glucolactone (4.24 g, 9.08 mmol) in 40 mL of toluene at −78° C. The solution was stirred for 1.5 h at the same temperature prior to quenching by addition of H$_2$O (20 mL). Then the reaction temperature was slowly raised to room temperature over 1.5 h. The reaction solution was extracted 3× with AcOEt, and washed 2× with brine prior to drying over Na$_2$SO$_4$. The volatiles were removed under vacuum using a rotary evaporator. The crude product (6.52 g) was dissolved in MeOH (170 mL) and cooled to −78° C. MeSO$_3$H (1.64 g, 17.08 mmol) was added via syringe, and then the reaction solution was slowly warmed to room temperature and held overnight. The reaction solution was cooled to 0° C. prior to quenching by addition of aqueous NaHCO$_3$ solution. The volatiles were removed under vacuum using a rotary evaporator. The residue was extracted 3× with AcOEt. The combined organic layers were washed 2× with brine prior to drying over sodium sulfate. The volatiles were removed with a rotary evaporator to give a white solid. Recrystallization from ethyl acetate/petroleum ether yielded 2.02 g of title compound. $^1$H NMR (CD$_3$OD, 400 MHz) δ 7.35 (s, 1H), 7.25 (s, 1H), 7.10 (s, 4H), 5.13 (d, J=12.8 Hz, 1H), 5.07 (d, J=12.8 Hz, 1H), 4.11 (d, J=15.2 Hz, 1H), 4.06 (d, J=15.2 Hz, 1H), 3.80-3.64 (m, 5H), 3.43 (dd, J=10.2, 8.6 Hz, 1H), 2.59 (q, J=7.6 Hz, 2H), 1.20 (t, J=7.6 Hz, 3H); MS ESI (m/z) 421 (M+1)$^+$, calc. 420.

Example 5

Preparation of (1S,3'R,4'S,5'S,6'R)-6-(4-cyclopropylbenzyl)-6'-(hydroxymethyl)-3',4',5',6'-tetrahydro-3H-spiro[isobenzofuran-1,2'-pyran]-3',4',5'-triol (Compound L)

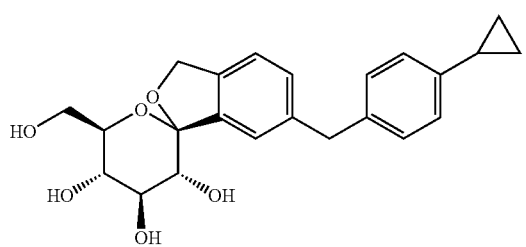

Compound L is prepared by a method analogous to that described in Example 1 by using (2-bromo-4-(4-cyclopropylbenzyl)benzyloxy)trimethylsilane (which is prepared as described for intermediate F).

Example 6

Preparation of (1S,3'R,4'S,5'S,6'R)-5-chloro-6-(4-cyclopropylbenzyl)-6'-(hydroxymethyl)-3',4',5',6'-tetrahydro-3H-spiro[isobenzofuran-1,2'-pyran]-3',4',5'-triol (Compound M)

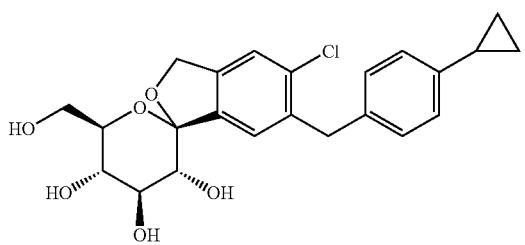

Compound M is prepared by a method analogous to that described in Example 1 by using (2-bromo-5-chloro-4-(4-cyclopropylbenzyl)benzyloxy)trimethylsilane (which is prepared as described for intermediate F).

Example 7

Preparation of (1S,3'R,4'S,5'S,6'R)-4-(4-ethylbenzyl)-6'-(hydroxymethyl)-3',4',5',6'-tetrahydro-3H-spiro[isobenzofuran-1,2'-pyran]-3',4',5'-triol (Compound N)

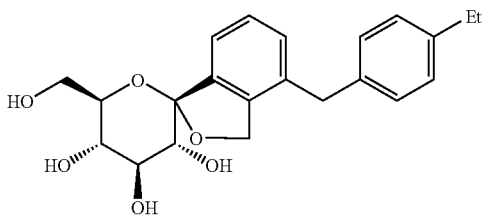

To a stirred −78° C. solution of 1-bromo-3-(4-ethylbenzyl)-2-((methoxymethoxy)methyl)benzene (52 mg, 0.15 mmol, prepared as described for intermediate K7) in 1.5 mL of 1:2 anhydrous THF/toluene under Ar, was added 0.1 mL of 1.6 M n-BuLi in hexane dropwise to insure the temperature remained below −65° C., and the mixture was stirred for 30 min at the same temperature. To the reaction mixture was added dropwise a solution of 2,3,4,6-tetra-O-trimethylsilyl-β-D-glucolactone (84 mg, 0.18 mmol) in 1 mL of toluene at −78° C. The solution was stirred for 5 h at the same temperature prior to quenching by addition of MeSO$_3$H (34 mg, 0.35 mmol) in 1 mL of THF. Then the reaction temperature was slowly raised to room temperature and kept overnight. The reaction solution was quenched by aqueous NaHCO$_3$ solution. The mixture was extracted 3× with AcOEt. The combined organic layers were washed 2× with brine prior to drying over sodium sulfate. The volatiles were removed using a rotary evaporator. The resulting residue was purified by preparative TLC to give 24 mg of title compound. $^1$H NMR (CD$_3$OD, 300 MHz) δ 7.18-6.96 (m, 7H), 4.90 (s, 2H), 3.93-3.57 (m, 8H), 2.56 (q, J=7.5 Hz, 2H), 1.17 (t, J=7.5 Hz, 3H); MS ESI (m/z) 387 (M+1)$^+$, calc. 386.

Example 8

Preparation of (1S,3'R,4'S,5'S,6'R)-5-chloro-4-(4-ethylbenzyl)-6'-(hydroxymethyl)-3',4',5',6'-tetrahydro-3H-spiro[isobenzofuran-1,2'-pyran]-3',4',5'-triol (Compound O)

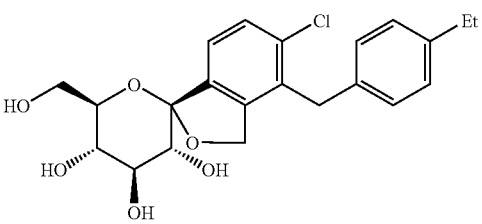

Compound O is prepared by a method analogous to that described in Example 1 by using (6-bromo-3-chloro-2-(4-ethylbenzyl)benzyloxy)trimethylsilane (which is prepared as described for intermediate F).

Example 9

Preparation of (1S,3'R,4'S,5'S,6'R)-5-chloro-4-(4-ethoxybenzyl)-6'-(hydroxymethyl)-3',4',5',6'-tetrahydro-3H-spiro[isobenzofuran-1,2'-pyran]-3',4',5'-triol (Compound P)

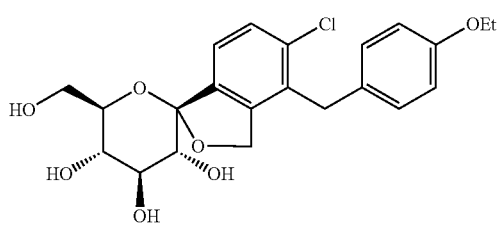

Compound P was prepared by a method analogous to that described in Example 1 by using 1-bromo-3-(4-ethoxybenzyl)-2-((methoxymethoxy)methyl)benzene (prepared as described for intermediate K7). $^1$H NMR (CD$_3$OD, 300 MHz): δ 7.35 (1H, s), 7.23 (1H, s), 7.10 (d, J=8.8 Hz, 2H), 6.81 (d, J=8.8 Hz, 2H), 5.10 (dd, J=24.6, 12.8 Hz, 2H), 4.05 (dd, J=13.6 Hz, 2H,), 3.99 (q, 2H), 3.82-3.59 (m, 5H), 3.45-3.40 (m, 1H), 1.36 (t, 3H).

Example 10

Preparation of (1S,3'R,4'S,5'S,6'R)-5-chloro-6'-(hydroxymethyl)-6-(4-isopropylbenzyl)-3',4',5',6'-tetrahydro-3H-spiro[isobenzofuran-1,2'-pyran]-3',4',5'-triol (Compound Q)

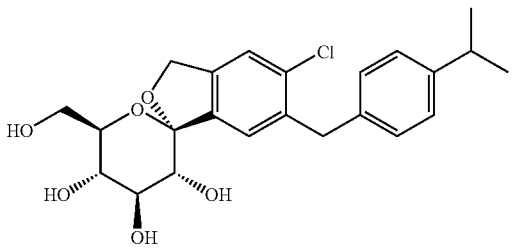

Compound Q was obtained starting from 1-bromo-4-chloro-5-(4-iso-propylbenzyl)-2-((methoxymethoxy)methyl)benzene (prepared as described for intermediate K7) by using methods analogous to those used to prepare compound K. $^1$H NMR (CD$_3$OD, 300 MHz) δ 7.36 (1H, s), 7.28 (1H, s), 7.11 (s, 4H), 5.11 (dd, J=24.2, 12.8 Hz, 2H), 4.09 (dd, J=15.6 Hz, 2H), 3.83-3.60 (m, 5H), 3.45 (t, J=8.8 Hz, 1H), 2.88~2.82 (m, 1H), 1.22 (d, 6H).

Example 11

Preparation of (1S,3'R,4'S,5'S,6'R)-5-chloro-6'-(hydroxymethyl)-6-(4-methoxybenzyl)-3',4',5',6'-tetrahydro-3H-spiro[isobenzofuran-1,2'-pyran]-3',4',5'-triol (Compound R)

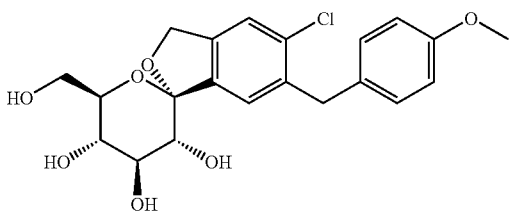

Compound R was obtained starting from 1-bromo-4-chloro-5-(4-methoxybenzyl)-2-((methoxymethoxy)methyl)benzene (prepared as described for intermediate K7) by using methods analogous to those used to prepare compound K. $^1$H NMR (CD$_3$OD, 300 MHz) δ 7.35 (s, 1H), 7.24 (s, 1H), 7.11 (d, J=8.4 Hz 2H), 6.83 (d, J=8.4 Hz, 2H), 5.10 (dd, J=24, 12.8 Hz, 2H), 4.05 (dd, J=15.6 Hz, 2H), 3.83-3.60 (m, 8H), 3.44 (t, J=9.2 Hz, 1H).

Example 12

Preparation of (1S,3'R,4'S,5'S,6'R)-6-(4-tert-butylbenzyl)-5-chloro-6'-(hydroxymethyl)-3',4',5',6'-tetrahydro-3H-spiro[isobenzofuran-1,2'-pyran]-3',4',5'-triol (Compound S)

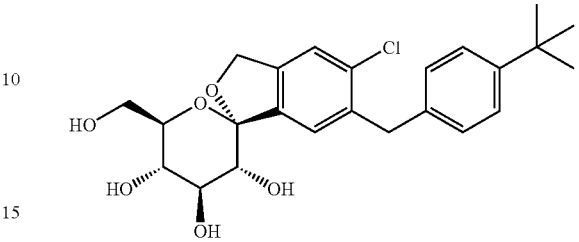

Compound S was obtained starting from 1-bromo-4-chloro-5-(4-tert-butylbenzyl)-2-((methoxymethoxy)methyl)benzene (prepared as described for intermediate K7) by using methods analogous to those used to prepare compound K. $^1$H NMR (CD$_3$OD, 300 MHz) δ 7.36 (s, 1H), 7.30 (d, J=8.8 Hz, 2H), 7.28 (s, 1H), 7.12 (d, J=8.8 Hz, 2H), 5.10 (dd, J=13.2 Hz, 2H), 4.10 (dd, J=15.2 Hz, 2H), 3.76-3.65 (m, 5H), 3.45 (t, 1H), 1.29 (s, 9H).

Example 13

Preparation of (1S,3'R,4'S,5'S,6'R)-5-chloro-6'-(hydroxymethyl)-6-(4-(trifluoromethoxy)benzyl)-3',4',5',6'-tetrahydro-3H-spiro[isobenzofuran-1,2'-pyran]-3',4',5'-triol (Compound T)

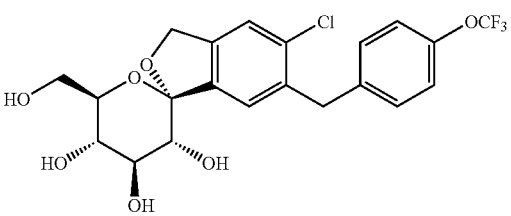

Compound T was obtained starting from 1-bromo-4-chloro-5-(4-trifluoromethoxybenzyl)-2-((methoxymethoxy)methyl)benzene (prepared as described for intermediate K7) by using methods analogous to those used to prepare compound K. $^1$H NMR (CD$_3$OD, 300 MHz) δ 7.38 (1H, s), 7.34 (1H, s), 7.30 (d, J=8.0 Hz, 2H), 7.16 (d, J=8.0 Hz, 2H), 5.10 (dd, J=24.4, 13.2 Hz, 2H), 4.18 (dd, 2H), 3.83-3.65 (m, 5H), 3.39 (t, 1H).

Example 14

Preparation of (1S,3'R,4'S,5'S,6'R)-5-chloro-6-(3-chloro-4-ethoxybenzyl)-6'-(hydroxymethyl)-3',4',5',6'-tetrahydro-3H-spiro[isobenzofuran-1,2'-pyran]-3',4',5'-triol (Compound U)

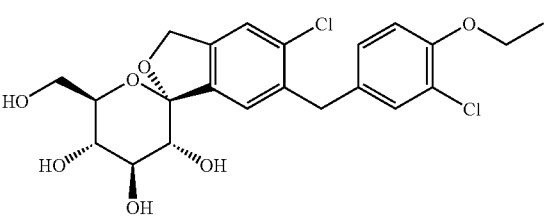

Compound U was obtained starting from 1-bromo-4-chloro-5-(3-chloro-4-ethoxybenzyl)-2-((methoxymethoxy)methyl)benzene (prepared as described for intermediate K7) by using methods analogous to those used to prepare compound K. $^1$H NMR (CD$_3$OD, 300 MHz) δ 7.37 (s, 1H), 7.28 (s, 1H), 7.18 (s, 1H), 7.08 (d, J=8.4 Hz, 1H), 6.94 (d, J=8.4 Hz, 1H), 5.11 (dd, J=25.2, 12.4 Hz, 2H), 4.11~4.01 (m, 4H), 3.82~3.64 (m, 5H), 3.45 (t, 1H), 1.40 (t, J=7.2 Hz, 3H).

Example 15

Preparation of (1S,3'R,4'S,5'S,6'R)-5-chloro-6-(4-ethoxy-2-methylbenzyl)-6'-(hydroxymethyl)-3',4',5',6'-tetrahydro-3H-spiro[isobenzofuran-1,2'-pyran]-3',4',5'-triol (Compound V)

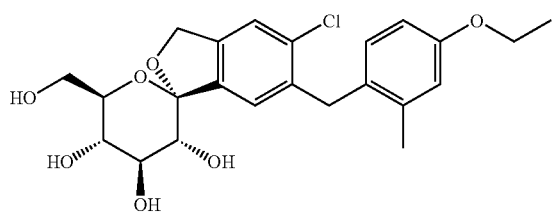

Compound V was obtained starting from 1-bromo-4-chloro-5-(4-ethoxy-2-methylbenzyl)-2-((methoxymethoxy)methyl)benzene (prepared as described for intermediate K7) by using methods analogous to those used to prepare compound K. $^1$H NMR (CD$_3$OD, 300 MHz) δ 7.33 (s, 1H), 7.18 (s, 1H), 6.90 (d, J=8.4 Hz, 1H), 6.75 (s, 1H), 6.65 (d, J=8.4 Hz, 1H), 5.10 (dd, J=24.4, 12.8 Hz, 2H), 4.07-3.99 (m, 4H), 3.82-3.59 (m, 5H), 3.40 (t, 1H), 2.30 (s, 3H), 1.37 (t, J=7 Hz, 3H).

Example 16

Preparation of (1S,3'R,4'S,5'S,6'R)-5-chloro-6-(2-ethoxy-4-methylbenzyl)-6'-(hydroxymethyl)-3',4',5',6'-tetrahydro-3H-spiro[isobenzofuran-1,2'-pyran]-3',4',5'-triol (Compound W)

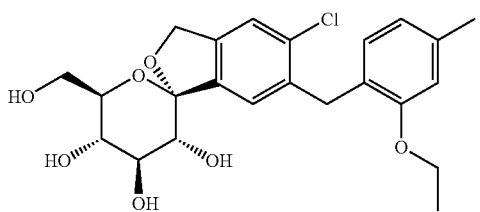

Compound W was obtained starting from 1-bromo-4-chloro-5-(2-ethoxy-4-methylbenzyl)-2-((methoxymethoxy)methyl)benzene (prepared as described for intermediate K7) by using methods analogous to those used to prepare compound K. $^1$H NMR (CD$_3$OD, 300 MHz) δ 7.33 (s, 1H), 6.90 (s, 1H), 6.83 (d, 1H), 6.70 (d, J=8.2 Hz, 1H), 6.62 (dd, J=8.2 Hz, 1H), 5.05 (dd, J=26.8, 12.8 Hz, 2H), 3.98-3.93 (m, 4H), 3.76-3.55 (m, 5H), 3.33 (t, 1H), 2.15 (s, 3H), 1.33 (t, J=7.0 Hz, 3H).

Example 17

Preparation of (1S,3'R,4'S,5'S,6'R)-5-chloro-6-(4-chloro-2-ethoxybenzyl)-6'-(hydroxymethyl)-3',4',5',6'-tetrahydro-3H-spiro[isobenzofuran-1,2'-pyran]-3',4',5'-triol (Compound X)

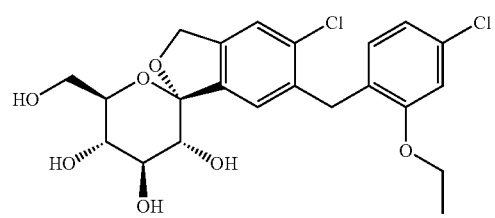

Compound X was obtained starting from 1-bromo-4-chloro-5-(4-chloro-2-ethoxybenzyl)-2-((methoxymethoxy)methyl)benzene (prepared as described for intermediate K7) by using methods analogous to those used to prepare compound K. $^1$H NMR (CD$_3$OD, 300 MHz) δ 7.39 (s, 1H), 7.10 (s, 1H), 6.98 (d, J=2.4 Hz, 1H), 6.95 (d, J=8.4 Hz, 1H), 6.77 (dd, J=8.4, 2.4 Hz, 1H), 5.12 (dd, J=25.2, 12.4 Hz, 2H), 4.19~4.09 (dd, 2H), 4.02 (q, 2H), 3.82-3.59 (m, 5H), 3.41 (t, 1H), 1.37 (t, J=7.2 Hz, 3H).

Example 18

Preparation of (1S,3'R,4'S,5'S,6'R)-5-chloro-6'-(hydroxymethyl)-6-(4-methoxy-2-methylbenzyl)-3',4',5',6'-tetrahydro-3H-spiro[isobenzofuran-1,2'-pyran]-3',4',5'-triol (Compound Y)

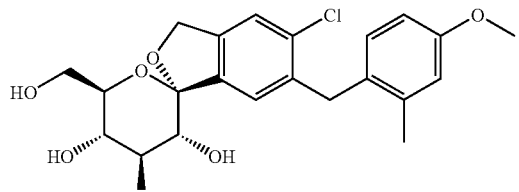

Compound Y was obtained starting from 1-bromo-4-chloro-5-(4-methoxy-2-methylbenzyl)-2-((methoxymethoxy)methyl)benzene by using methods analogous to those used to prepare compound K. $^1$H NMR (CD$_3$OD, 300 MHz) δ 7.34 (s, 1H), 7.10 (s, 1H), 6.84 (d, J=7.6 Hz, 1H), 6.78 (s, 1H), 6.66 (d, J=7.6 Hz, 1H), 5.11 (dd, J=24.8 Hz, 12.8 Hz, 2H), 4.03 (dd, 2H), 3.79-3.60 (m, 8H), 3.40 (t, 1H), 2.32 (s, 3H).

Example 19

Preparation of (1S,3'R,4'S,5'S,6'R)-5-chloro-6-(2-chloro-4-ethoxybenzyl)-6'-(hydroxymethyl)-3',4',5',6'-tetrahydro-3H-spiro[isobenzofuran-1,2'-pyran]-3',4',5'-triol (Compound Z)

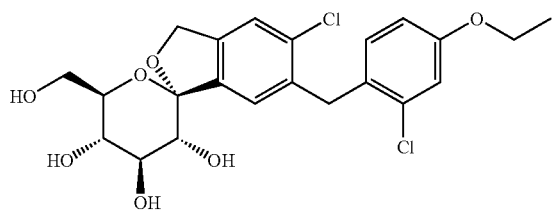

Compound Z was obtained starting from 1-bromo-4-chloro-5-(2-chloro-4-ethoxybenzyl)-2-((methoxymethoxy)methyl)benzene (prepared as described for intermediate K7) by using methods analogous to those used to prepare compound K. $^1$H NMR (CD$_3$OD, 300 MHz) δ 7.35 (s, 1H), 7.22 (s, 1H), 6.98 (d, 1H), 6.94 (d, 1H), 6.83 (dd, 1H), 5.11 (dd, J=24, 12.8 Hz, 2H), 4.09-4.01 (m, 4H), 3.82-3.61 (m, 5H), 3.40 (t, 1H), 1.40 (t, 3H).

Example 20

Preparation of (1S,3'R,4'S,5'S,6'R)-5-chloro-6-(2-fluoro-3-methylbenzyl)-6'-(hydroxymethyl)-3',4',5',6'-tetrahydro-3H-spiro[isobenzofuran-1,2'-pyran]-3',4',5'-triol (Compound AA)

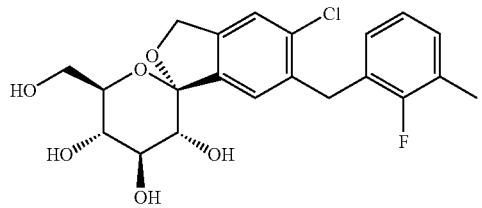

Compound AA was obtained starting from 1-bromo-4-chloro-5-(2-fluoro-3-methylbenzyl)-2-((methoxymethoxy)methyl)benzene (prepared as described for intermediate K7) by using methods analogous to those used to prepare compound K. $^1$H NMR (CD$_3$OD, 300 MHz) δ 7.36 (s, 1H), 7.27 (s, 1H), 7.06 (d, 1H), 7.02~6.98 (m, 1H), 6.90 (t, 1H), 5.11 (dd, J=24.4, 12.8 Hz, 2H), 4.07 (dd, 2H), 3.83-3.60 (m, 5H), 3.45 (t, 1H), 2.21 (s, 3H).

Example 21

Preparation of (1S,3'R,4'S,5'S,6'R)-5-chloro-6-(4-fluoro-2-methylbenzyl)-6'-(hydroxymethyl)-3',4',5',6'-tetrahydro-3H-spiro[isobenzofuran-1,2'-pyran]-3',4',5'-triol (Compound AB)

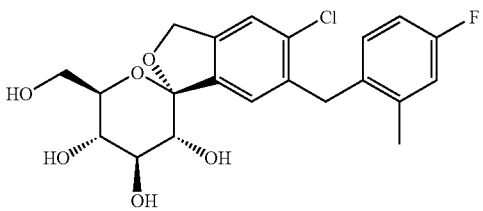

Compound AB was obtained starting from 1-bromo-4-chloro-5-(4-fluoro-2-methylbenzyl)-2-((methoxymethoxy)methyl)benzene (prepared as described for intermediate K7) by using methods analogous to those used to prepare compound K. $^1$H NMR (CD$_3$OD, 300 MHz) δ 7.40 (s, 1H), 7.00 (s, 1H), 6.94 (m, 2H), 6.84~6.80 (m, 1H), 5.11 (dd, J=26, 12.8 Hz, 2H), 4.07 (s, 2H), 3.81~3.59 (m, 5H), 3.40 (t, 1H), 2.26 (s, 3H).

Example 22

Preparation of (1S,3'R,4'S,5'S,6'R)-5-chloro-6'-(hydroxymethyl)-6-(2-methoxy-4-methylbenzyl)-3',4',5',6'-tetrahydro-3H-spiro[isobenzofuran-1,2'-pyran]-3',4',5'-triol (Compound AC)

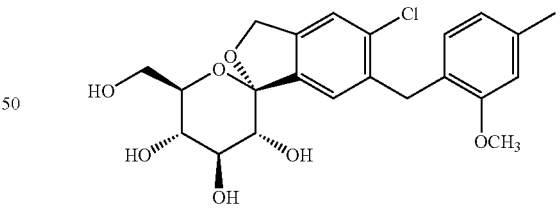

Compound AC was obtained starting from 1-bromo-4-chloro-5-(2-methoxy-4-methylbenzyl)-2-((methoxymethoxy)methyl)benzene (prepared as described for intermediate K7) by using methods analogous to those used to prepare compound K. $^1$H NMR (CD$_3$OD, 300 MHz) δ 7.38 (s, 1H), 7.06 (s, 1H), 6.89 (d, 1H), 6.77 (d, 1H), 6.68 (dd, 1H), 5.11 (dd, J=26.2, 13.2 Hz, 2H), 4.02 (t, 2H), 3.81~3.70 (m, 6H), 3.65~3.58 (m, 2H), 3.37 (t, 1H), 2.20 (s, 3H).

Example 23

Preparation of (1S,3'R,4'S,5'S,6'R)-5-chloro-6-(2-ethoxy-4-fluorobenzyl)-6'-(hydroxymethyl)-3',4',5',6'-tetrahydro-3H-spiro[isobenzofuran-1,2'-pyran]-3',4',5'-triol (Compound AD)

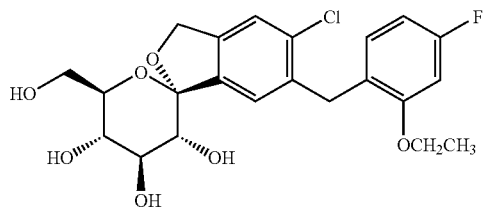

Compound AD was obtained starting from 1-bromo-4-chloro-5-(2-ethoxy-4-fluorobenzyl)-2-((methoxymethoxy)methyl)benzene (prepared as described for intermediate K7) by using methods analogous to those used to prepare compound K. $^1$H NMR (CD$_3$OD, 300 MHz) δ 7.34 (s, 1H), 7.21 (s, 1H), 7.01 (t, 1H), 6.70 (d, 1H), 6.55 (t, 1H), 5.10 (dd, J=24.4, 13.2 Hz, 2H), 4.11-4.00 (m, 4H), 3.81-3.59 (m, 5H), 3.40 (t, 1H), 1.40 (t, 3H).

Example 24

Preparation of (1S,3'R,4'S,5'S,6'R)-5-chloro-6-[1-(4-ethylphenyl)cyclopropyl]-6'-(hydroxymethyl)-3',4',5',6'-tetrahydro-3H-spiro[isobenzofuran-1,2'-pyran]-3',4',5'-triol (Compound AE)

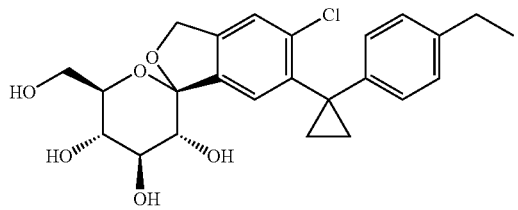

Compound AE was prepared starting from 1-(4-ethylphenyl)-1-[4-(methoxymethoxy)methyl-5-bromo-2-chloro]phenyl-cyclopropane using methods analogous to those described above to prepare compound K. $^1$H NMR (CD$_3$OD, 300 MHz) δ 7.34 (s, 1H), 7.21 (s, 1H), 7.02 (t, 1H), 6.70 (d, 1H), 6.55 (t, 1H), 5.10 (dd, J=24.4, 13.2 Hz, 2H), 4.11-4.00 (m, 4H), 3.81-3.59 (m, 5H), 3.40 (t, 1H,), 1.40 (t, 3H).

Example 25

Preparation of ((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl 4-methylbenzenesulfonate (Compound AF)

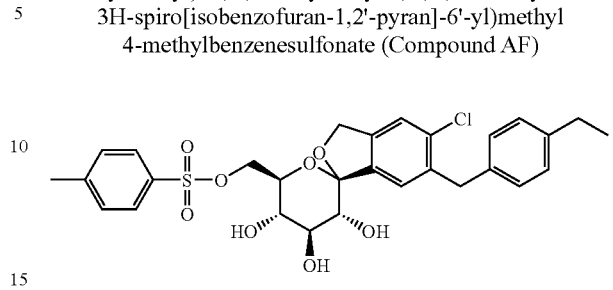

To a stirred solution of (1S,3'R,4'S,5'S,6'R)-5-chloro-6-(4-ethylbenzyl)-6'-(hydroxymethyl)-3',4',5',6'-tetrahydro-3H-spiro[isobenzofuran-1,2'-pyran]-3',4',5'-triol (0.15 g, 0.356 mmol) in 3.5 mL of 2,6-lutidine was added p-toluenesulfonyl chloride (0.34 g, 1.78 mmol). After stirring for 21 h at ambient temperature, the solvent was distilled off. The residue was taken up with 30 mL of ethyl acetate, washed with 1 M hydrochloric acid and brine prior to drying over Na$_2$SO$_4$. Concentration under reduced pressure provided the crude product, which was purified by preparative TLC to give 135 mg of title compound. $^1$H NMR (CD$_3$OD, 400 MHz) δ 7.61 (d, J=8.0 Hz, 2H), 7.35 (s, 1H), 7.21 (s, 1H), 7.16 (d, J=8.4 Hz, 2H), 7.11 (d, J=8.8 Hz, 4H), 5.02 (d, J=12.8 Hz, 1H), 4.97 (d, J=12.8 Hz, 1H), 4.22-4.08 (m, 4H), 3.90-3.86 (m, 1H), 3.71-3.65 (m, 2H), 3.39-3.34 (m, 1H), 2.59 (q, J=7.6 Hz, 2H), 2.33 (s, 3H), 1.18 (t, J=7.6 Hz, 3H); LC-MS (m/z) 575 [(M+1)+], 619 [(M+45)−].

Example 26

Preparation of (1S,3'R,4'S,5'S,6'R)-5-chloro-6-(4-ethylbenzyl)-6'-(methoxymethyl)-3',4',5',6'-tetrahydro-3H-spiro[isobenzofuran-1,2'-pyran]-3',4',5'-triol (Compound AG)

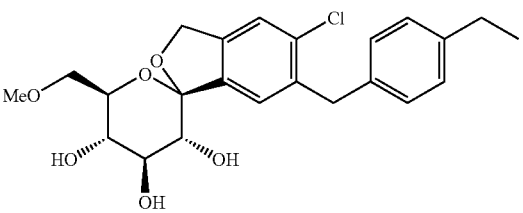

To ((1S,3'R,4'S,5'S,6'R)-5-chloro-6-(4-ethylbenzyl)-3',4', 5'-trihydroxy-3',4',5',6'-tetrahydro-3H-spiro[isobenzofuran-1,2'-pyran]-6'-yl)methyl 4-methylbenzenesulfonate (14 mg, 0.0243 mmol) was added 1 mL of freshly prepared sodium methoxide solution (3 M). After stirring overnight, the reaction was quenched with 2 mL of water. The organic solvent was distilled off and the water layer was extracted with ethyl acetate. The combined organic layers were washed with brine prior to drying over Na$_2$SO$_4$. Concentration under reduced pressure provided the crude product, which was purified by preparative TLC to give 7 mg of title compound. $^1$H NMR (CD$_3$OD, 400 MHz) δ 7.36 (s, 1H), 7.23 (s, 1H), 7.10 (s, 4H), 5.13 (d, J=13.0 Hz, 1H), 5.07 (d, J=13.0 Hz, 1H), 4.09 (s, 2H), 3.91-3.86 (m, 1H), 3.76-3.67 (m, 2H), 3.62-3.55 (m, 2H), 3.43 (dd, J=10.4, 8.4 Hz, 1H), 3.31 (m, 3H), 2.60 (q, J=7.6 Hz, 2H), 1.20 (t, J=7.6 Hz, 3H); MS ESI (m/z) 435 (M+1)$^+$, calc. 434.

Example 27

Preparation of ((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl acetate (Compound AH)

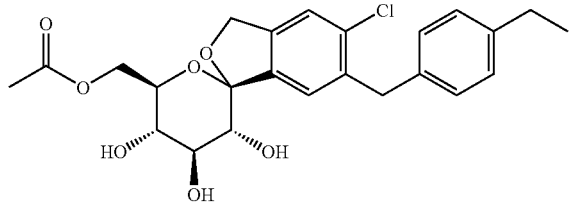

To a solution of ((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl 4-methylbenzenesulfonate (20 mg, 0.034 mmol) in 1 mL of DMF, was added sodium acetate (36 mg, 0.44 mmol). The solution was warmed to 80° C. and kept at the same temperature overnight. 5 mL of water was added and the solution was extracted with ethyl acetate. The combined organic layers were washed with brine prior to drying over sodium sulfate. Concentration under reduced pressure provided the crude product, which was purified by preparative TLC to give 6 mg of title compound. $^1$H NMR (CD$_3$OD, 400 MHz) δ 7.37 (s, 1H), 7.19 (s, 1H), 7.11 (s, 4H), 5.12 (d, J=13.0 Hz, 1H), 5.08 (d, J=13.0 Hz, 1H), 4.32 (dd, J=11.6, 2.0 Hz, 1H), 4.17-4.09 (m, 3H), 3.99-3.94 (m, 1H), 3.77-3.68 (m, 2H), 3.43 (dd, J=9.8, 8.6 Hz, 1H), 2.60 (q, J=7.6 Hz, 2H), 1.99 (s, 3H), 1.20 (t, J=7.6 Hz, 3H); MS ESI (m/z) 485 (M+Na)$^+$, calc. 462.

Example 28

Preparation of (1S,3'R,4'S,5'S,6'R)-5-chloro-6-(4-ethylbenzyl)-6'-((2,2,2-trifluoroethoxy)methyl)-3',4',5',6'-tetrahydro-3H-spiro[isobenzofuran-1,2'-pyran]-3',4',5'-triol (Compound AI)

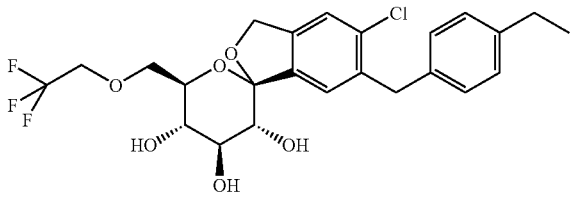

To ((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl 4-methylbenzenesulfonate (14 mg, 0.024 mmol) was added 1 mL of freshly prepared sodium trifluoroethoxide solution (1.5 M). After refluxing for 5 h at temperature, the reaction was quenched with 2 mL of water. The organic solvent was distilled off and the water layer was extracted with ethyl acetate. The combined organic layers were washed with brine prior to drying over Na$_2$SO$_4$. Concentration under reduced pressure provided the crude product, which was purified by preparative TLC to give 6 mg of title compound. $^1$H NMR (CD$_3$OD, 300 MHz) δ 7.36 (s, 1H), 7.19 (s, 1H), 7.09 (s, 4H), 5.12 (d, J=13.2 Hz, 1H), 5.07 (d, J=13.2 Hz, 1H), 4.11 (d, J=15.5 Hz, 1H), 4.05 (d, J=15.5 Hz, 1H), 3.89-3.66 (m, 7H), 3.48 (t, J=9.2 Hz, 1H), 2.59 (q, J=7.8 Hz, 2H), 1.19 (t, J=7.8 Hz, 3H); MS ESI (m/z) 503 (M+1)$^+$, calc. 502.

Example 29

Preparation of (1S,3'R,4'S,5'S,6'R)-6'-(azidomethyl)-5-chloro-6-(4-ethylbenzyl)-3',4',5',6'-tetrahydro-3H-spiro[isobenzofuran-1,2'-pyran]-3',4',5'-triol (Compound AJ)

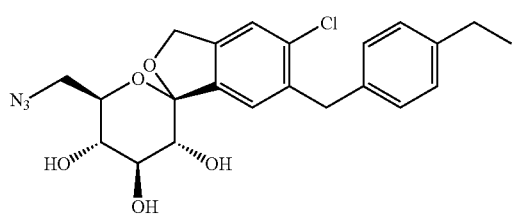

To a solution of ((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl 4-methylbenzenesulfonate (38 mg, 0.066 mmol) in 1 mL of DMF was added sodium azide (22 mg, 0.338 mmol) and a catalytic amount of TBAI. The solution was warmed to 60° C. and kept at the same temperature overnight. 5 mL of water was added and the solution was extracted with ethyl acetate. The combined organic layers were washed with brine prior to drying over sodium sulfate. Concentration under reduced pressure provided the crude product, which was purified by preparative TLC to give 23 mg of title compound. $^1$H NMR (CD$_3$OD, 400 MHz) δ 7.36 (s, 1H), 7.22 (s, 1H), 7.08 (s, 4H), 5.14 (d, J=12.4 Hz, 1H), 5.09 (d, J=12.4 Hz, 1H), 4.08 (s, 2H), 3.96-3.91 (m, 1H), 3.77-3.70 (m, 2H), 3.52-3.45 (m, 2H), 3.35-3.31 (m, 1H), 2.59 (q, J=7.6 Hz, 2H), 1.20 (t, J=7.6 Hz, 3H); MS ESI (m/z) 446 (M+1)$^+$, calc. 445.

Example 30

Preparation of (1S,3'R,4'S,5'S,6'R)-6'-(aminomethyl)-5-chloro-6-(4-ethylbenzyl)-3',4',5',6'-tetrahydro-3H-spiro[isobenzofuran-1,2'-pyran]-3',4',5'-triol (Compound AK)

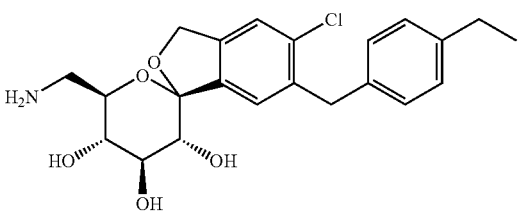

To a solution of (1S,3'R,4'S,5'S,6'R)-6'-(azidomethyl)-5-chloro-6-(4-ethylbenzyl)-3',4',5',6'-tetrahydro-3H-spiro[isobenzofuran-1,2'-pyran]-3',4',5'-triol (25 mg, 0.056 mmol) in 0.5 mL of THF/H$_2$O (4:1), was added PPh$_3$ (43 mg, 0.164 mmol). The solution was stirred at room temperature for 4.5 h. Then the volatiles were removed under reduced pressure using a rotary evaporator. The resulting residue was purified by preparative HPLC to give 14 mg of title compound. $^1$H NMR (CD$_3$OD, 300 MHz) δ 7.39 (s, 1H), 7.23 (s, 1H), 7.10 (s, 4H), 5.16 (d, J=12.8 Hz, 1H), 5.10 (d, J=12.8 Hz, 1H), 4.13 (d, J=15.6 Hz, 1H), 4.05 (d, J=15.6 Hz, 1H), 4.02-3.94 (m, 1H), 3.75 (dd, J=4.1, 1.1 Hz, 2H), 3.34-3.32 (m, 2H☐, 2.98-2.91 (m, 1H ☐, 2.60 (q, J=7.5 Hz, 2H), 1.20 (t, J=7.5 Hz, 3H); MS ESI (m/z) 420 (M+1)$^+$, calc. 419.

Example 31

Preparation of (1S,3'R,4'S,5'S,6'R)-6'-(aminomethyl)-5-chloro-6-(4-isopropylbenzyl)-3',4',5',6'-tetrahydro-3H-spiro[isobenzofuran-1,2'-pyran]-3',4',5'-triol (Compound AL)

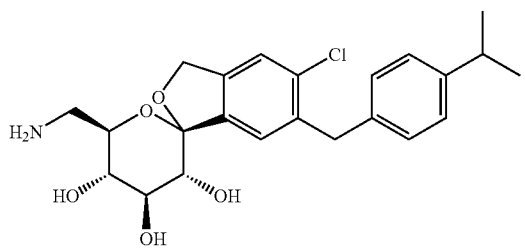

Compound AL was synthesized starting from (1S,3'R,4'S,5'S,6'R)-6'-(azidomethyl)-5-chloro-6-(4-iso-propylbenzyl)-3',4',5',6'-tetrahydro-3H-spiro[isobenzofuran-1,2'-pyran] using methods analogous to those described above to prepare compound AK. $^1$H NMR (CD$_3$OD, 300 MHz) δ 7.39 (s, 1H), 7.25 (s, 1H), 7.12 (s, 4H), 5.16 (d, J=13.2 Hz, 1H), 5.10 (d, J=13.2 Hz, 1H), 4.13 (d, J=15.6 Hz, 1H), 4.05 (d, J=15.6 Hz, 1H), 4.02-3.95 (m, 1H), 3.76-3.74 (m, 2H), 3.36-3.33 (m, 1H), 2.99-2.83 (m, 3H), 1.22 (d, J=6.9 Hz, 6H); MS ESI (m/z) 434 (M+1)$^+$, calc. 433.

Example 32

Preparation of N-(((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl)acetamide (Compound AM)

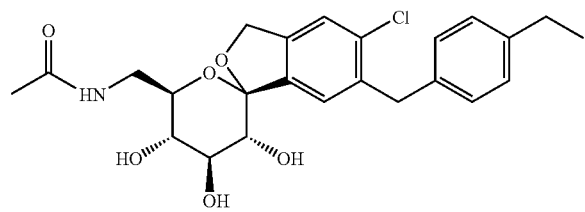

To a stirred solution of (1S,3'R,4'S,5'S,6'R)-6'-(aminomethyl)-5-chloro-6-(4-ethylbenzyl)-3',4',5',6'-tetrahydro-3H-spiro[isobenzofuran-1,2'-pyran]-3',4',5'-triol (20 mg, 0.047 mmol) and 0.04 mL of pyridine in 1 mL of dichloromethane, was added acetic anhydride (45 μL, 0.048 mmol) and 3 mg of 4-dimethylaminopyridine. After being stirred for 2 h at ambient temperature, the reaction mixture was diluted with 20 mL of dichloromethane, washed with 1 M hydrochloric acid and concentrated. The residue was dissolved in 1 mL of methanol and cooled in an ice bath. After addition of 0.3 mL of 4 M potassium hydroxide solution, the mixture was stirred for 2 h at ambient temperature. The reaction mixture was then neutralized with 1 M hydrochloric acid and concentrated. The residue was partitioned between aqueous sodium hydrogen carbonate solution and ethyl acetate, and the organic layer was separated and dried over sodium sulfate. Concentration under reduced pressure provided the crude product, which was purified by preparative TLC to give 5 mg of title compound. $^1$H NMR (CD$_3$OD, 400 MHz) δ 7.25 (s, 1H), 7.11 (s, 1H), 6.99 (s, 4H), 5.00 (d, J=12.6 Hz, 1H), 4.95 (d, J=12.6 Hz, 1H), 4.00 (d, J=15.4 Hz, 1H), 3.95 (d, J=15.4 Hz, 1H), 3.71-3.57 (m, 3H), 3.45 (dd, J=14.4, 2.8 Hz, 1H), 3.17-3.11 (m, 2H), 2.48 (q, J=7.6 Hz, 2H), 1.09 (t, J=7.6 Hz, 3H); MS ESI (m/z) 484 (M+Na)$^+$, calc. 461.

Example 33

Preparation of N-(((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl)pivalamide (Compound AN)

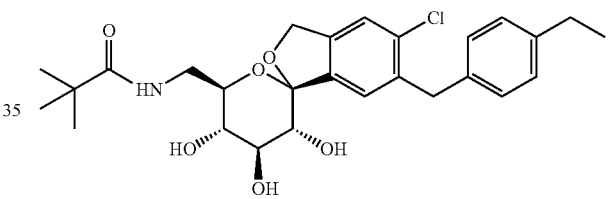

To a stirred solution of (1S,3'R,4'S,5'S,6'R)-6'-(aminomethyl)-5-chloro-6-(4-ethylbenzyl)-3',4',5',6'-tetrahydro-3H-spiro[isobenzofuran-1,2'-pyran]-3',4',5'-triol (20 mg, 0.047 mmol) and 0.04 mL of pyridine in 1 mL of dichloromethane was added of pivaloyl chloride (60 μL, 0.05 mmol) and 3 mg of 4-dimethylaminopyridine. After being stirred for 2 h at ambient temperature, the reaction mixture was diluted with 20 mL of dichloromethane, washed with 1 M hydrochloric acid and concentrated. The residue was dissolved in 1 mL of methanol and cooled in an ice bath. After addition of 0.3 mL of 4 M potassium hydroxide solution, the mixture was stirred for 2 h at ambient temperature. The reaction mixture was then neutralized with 1 M hydrochloric acid and concentrated. The residue was partitioned between aqueous sodium hydrogen carbonate solution and ethyl acetate, and the organic layer was separated and dried over sodium sulfate. Concentration under reduced pressure provided the crude product, which was purified by preparative TLC to give 6.8 mg of title compound. $^1$H NMR (CD$_3$OD, 300 MHz) δ 7.37 (s, 1H), 7.16 (s, 1H), 7.10 (s, 4H), 5.07 (s, 2H), 4.12 (d, J=15.8 Hz, 1H), 4.04 (d, J=15.8 Hz, 1H), 3.82-3.59 (m, 3H), 3.45-3.39 (m, 2H), 3.43 (dd, J=9.9, 8.4 Hz, 1H), 2.60 (q, J=7.6 Hz, 2H), 1.20 (t, J=7.6 Hz, 3H), 1.11 (s, 9H); MS ESI (m/z) 504 (M+1)$^+$, calc. 503.

Example 34

Preparation of (1S,3'R,4'S,5'S,6'R)-5-chloro-6-(4-ethylbenzyl)-6'-(morpholinomethyl)-3',4',5',6'-tetrahydro-3H-spiro[isobenzofuran-1,2'-pyran]-3',4',5'-triol (Compound AO)

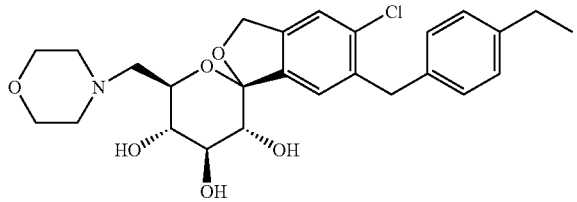

((1S,3'R,4'S,5'S,6'R)-5-chloro-6-(4-ethylbenzyl)-3',4',5'-trihydroxy-3',4',5',6'-tetrahydro-3H-spiro[isobenzofuran-1,2'-pyran]-6'-yl)methyl 4-methylbenzenesulfonate (20 mg, 0.034 mmol) was dissolved in 1 mL of morpholine. Then the solution was allowed to reflux overnight. Concentration under reduced pressure provided the crude product, which was purified by preparative TLC to give 15 mg of title compound. $^1$H NMR (CD$_3$OD, 400 MHz) δ 7.37 (s, 1H), 7.18 (s, 1H), 7.11 (d, J=8.0 Hz, 2H), 7.09 (d, J=8.8 Hz, 2H), 5.17 (d, J=13.2 Hz, 1H), 5.11 (d, J=13.2 Hz, 1H), 4.65-4.60 (m, 2H), 4.18-4.00 (m, 4H), 3.82-3.50 (m, 7H), 3.31-3.25 (m, 1H), 3.08-2.99 (m, 2H), 2.61 (q, J=7.6 Hz, 2H), 1.21 (t, J=7.6 Hz, 3H); MS ESI (m/z) 490 (M+1)$^+$, calc. 489.

Example 35

Preparation of (1S,3'R,4'S,5'S,6'R)-5-chloro-6'-((dimethylamino)methyl)-6-(4-isopropylbenzyl)-3',4',5',6'-tetrahydro-3H-spiro[isobenzofuran-1,2'-pyran]-3',4',5'-triol (Compound AP)

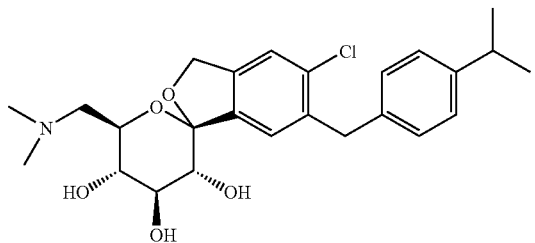

To a solution of ((1S,3'R,4'S,5'S,6'R)-5-chloro-6-(4-isopropylbenzyl)-3',4',5'-trihydroxy-3',4',5',6'-tetrahydro-3H-spiro[isobenzofuran-1,2'-pyran]-6'-yl)methyl 4-methylbenzenesulfonate (15 mg, 0.025 mmol) and dimethylamino hydrochloride (48 mg, 0.588 mmol) in DMF (1 mL), was added Et$_3$N (67 mg, 0.662 mmol). After being stirred for 24 h at 80° C., the reaction mixture was diluted with H$_2$O and extracted 3× with AcOEt. The combined organic layers were washed with brine prior to drying over Na$_2$SO$_4$. The volatiles were removed under reduced pressure. The resulting residue was purified by preparative HPLC to yield 6 mg of title compound. $^1$H NMR (CD$_3$OD, 300 MHz) δ 7.41 (s, 1H), 7.24 (s, 1H), 7.13 (s, 4H), 5.18 (d, J=13.5 Hz, 1H), 5.13 (d, J=13.5 Hz, 1H), 4.17-4.02 (m, 3H), 3.76-3.75 (m, 2H), 3.46-3.18 (m, 3H), 2.90-2.81 (m, 1H), 2.76 (s, 6H), 1.22 (d, J=6.9 Hz, 6H); MS ESI (m/z) 462 (M+1)$^+$, calc. 461.

Example 36

Preparation of ((1S,3'R,4'S,5'S,6'R)-5-chloro-3',4',5'-trihydroxy-6'-(hydroxymethyl)-3',4',5',6'-tetrahydro-3H-spiro[isobenzofuran-1,2'-pyran]-6-yl)(4-ethylphenyl)methanone (Compound AQ)

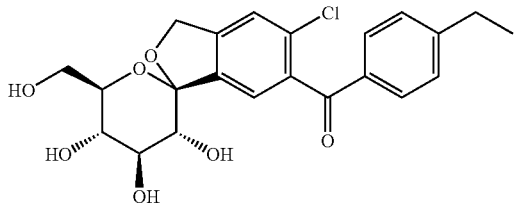

To a stirred −78° C. solution of 5-bromo-2-chloro-4-((methoxymethoxy)methyl)phenyl-4'-ethylphenyl-1,3-dioxolane (46 mg, 0.104 mmol, prepared from intermediate K5 by protection of the ketone with ethylene glycol, reduction of the ester and protection of the resulting alcohol with methoxymethyl chloride) in 1 mL of 1:2 anhydrous THF/toluene under Ar, was added 0.05 mL of 2.5 M n-BuLi in hexane dropwise to insure the temperature remained below −65° C., and the mixture was stirred for 40 min at the same temperature. To the reaction mixture was added dropwise a solution of 2,3,4,6-tetra-O-trimethylsilyl-β-D-glucolactone (59 mg, 0.126 mmol) in 1 mL of toluene at −78° C. The solution was stirred for 2 h at the same temperature prior to quenching by addition of H$_2$O (1 mL). Then the reaction temperature was slowly raised to room temperature over 1.5 h. The reaction solution was extracted 3× with AcOEt, and washed 2× with brine prior to drying over Na$_2$SO$_4$. The volatiles were removed under vacuum using a rotary evaporator, and 110 mg of the crude product was dissolved in MeOH (1.5 mL) and cooled to −78° C. MeSO$_3$H (23 mg, 0.239 mmol) in MeOH (0.5 mL) was added via syringe. Then the reaction solution was slowly warmed to room temperature and stirred overnight. The reaction solution was cooled to 0° C. prior to quenching by adding aqueous NaHCO$_3$ solution. The volatiles were removed under vacuum using a rotary evaporator. The resulting aqueous layer was extracted 3× with AcOEt. The combined organic layers were washed 2× with brine prior to drying over Na$_2$SO$_4$. Concentration under reduced pressure provided the crude product, which was purified by preparative TLC to yield 31 mg of title compound. $^1$H NMR (CD$_3$OD, 300 MHz) δ 7.72 (d, J=8.1 Hz, 2H), 7.50 (s, 1H), 7.42 (s, 1H), 7.35 (d, J=8.7 Hz, 2H), 5.24 (d, J=13.5 Hz, 1H), 5.17 (d, J=13.5 Hz, 1H), 3.85-3.65 (m, 5H), 3.49-3.42 (m, 1H), 2.73 (q, J=7.6 Hz, 2H), 1.26 (t, J=7.6 Hz, 3H); MS ESI (m/z) 435 (M+1)$^+$, calc. 434.

Example 37

Summary Procedure for the Synthesis of Compound AV

Figure 16:
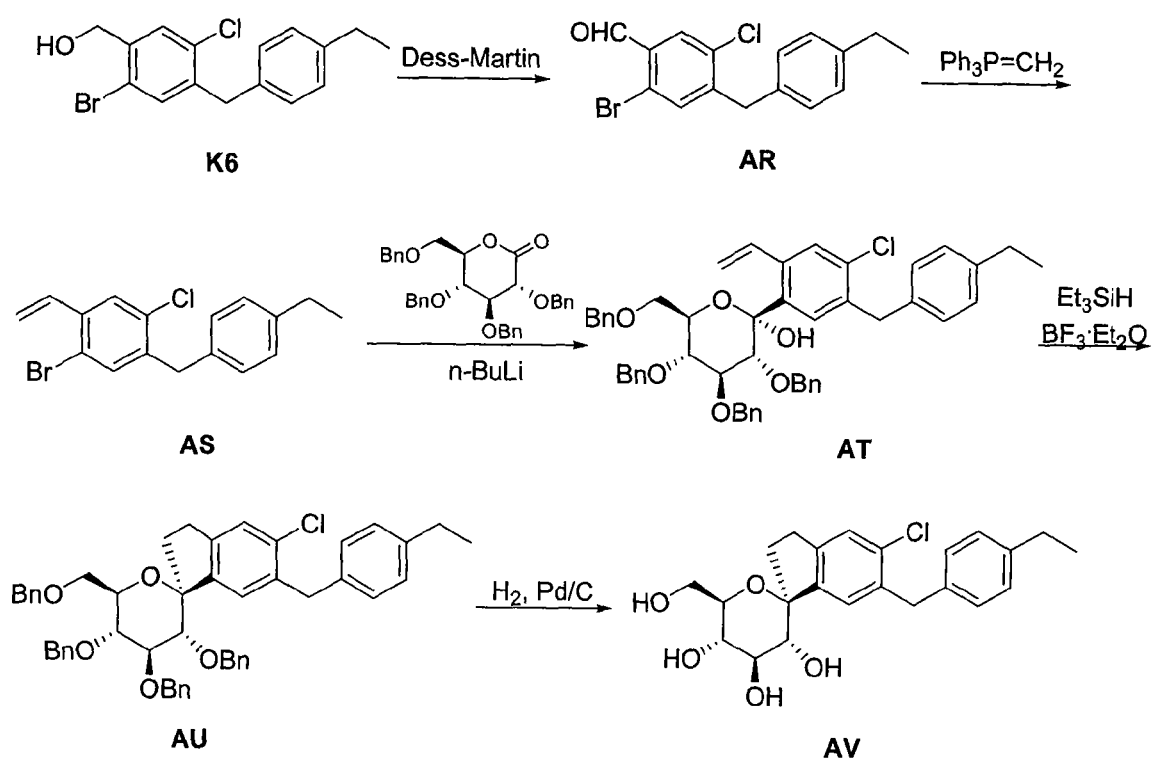
FIG. 16 is the summary procedure for the synthesis of compound AV of the invention.

The synthesis of compound AV within the invention is outlined in FIG. 16, with the details of the individual steps given below.

Preparation of 2-bromo-5-chloro-4-(4-ethylbenzyl)benzaldehyde (Intermediate AR)

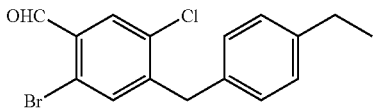

To a cooled solution (−5° C.) of (2-bromo-5-chloro-4-(4-ethylbenzyl)phenyl)methanol (9.7 g, 29.4 mmol) in dry dichloromethane (100 mL), was added dropwise a solution of Dess-Martin reagent (18.7 g, 44 mmol) in 100 mL of dry dichloromethane. After it was stirred at room temperature for 2 h, TLC showed the reaction was complete. The reaction was quenched by addition of 10 mL of 1 M NaOH. The organic layer was washed 1× with NaHSO₃, 2× with NaHCO₃, 3× with brine, dried over anhydrous Na₂SO₄. Concentration under reduced pressure provided the pure product as a white solid. Yield: 9.3 g (96%). $^1$H NMR (CDCl₃, 300 MHz) δ 10.24 (s, 1H), 7.91 (s, 1H), 7.40 (s, 1H), 7.18 (s, 1H), 7.15 (s, 1H), 7.11 (s, 1H), 7.09 (s, 1H), 4.08 (s, 2H), 4.02 (s, 2H), 2.63 (q, J=7.8 Hz, 2H), 1.23 (t, J=7.8 Hz, 3H).

Preparation of 1-bromo-4-chloro-5-(4-ethylbenzyl)-2-vinylbenzene (Intermediate AS)

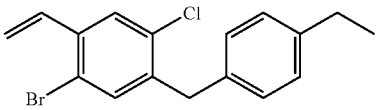

To a suspension of Ph₃PCH₃I (3.151 g, 7.8 mmol) in 22 mL of dry toluene, was added dropwise with KN(TMS)₂ (15.64 mL, 7.8 mmol, 0.5 M in toluene) under argon. After it was stirred for 1 h, a solution of 2-bromo-5-chloro-4-(4-ethylbenzyl)benzaldehyde (1.76 g, 5.2 mmol) in 17 mL of toluene was added. This reaction mixture was stirred at room temperature and monitored by TLC (PE, R$_f$=0.8). After being stirred for 4 h, the reaction mixture was quenched by addition of 5 mL of saturated NaHCO₃. The organic layer was washed 2× with H₂O, 2× with brine, dried over anhydrous Na₂SO₄. Concentration under reduced pressure provided the crude product, which was purified by column chromatography on silica gel (PE), to give the title compound as a colorless oil. Yield: 3.0 g (96%). $^1$H NMR (CDCl₃, 300 MHz) δ 7.54 (s, 1H), 7.33 (s, 1H), 7.14 (d, J=2.1 Hz, 1H), 7.12 (d, J=2.4 Hz, 1H), 7.10 (d, J=2.1 Hz, 1H), 7.09 (d, J=2.4 Hz, 1H), 6.92 (dd, J=11.0, 17.6 Hz, 1H), 5.68 (dd, J=17.6, 0.9 Hz, 1H), 5.37 (dd, J=11.0, 0.9 Hz, 1H), 4.02 (s, 2H), 2.63 (q, J=7.6 Hz, 2H), 1.23 (t, J=7.6 Hz, 3H).

Preparation of (2S,3R,4S,5R,6R)-3,4,5-tris(benzyloxy)-6-(benzyloxymethyl)-2-(4-chloro-5-(4-ethylbenzyl)-2-vinylphenyl)tetrahydro-2H-pyran-2-ol (Intermediate AT)

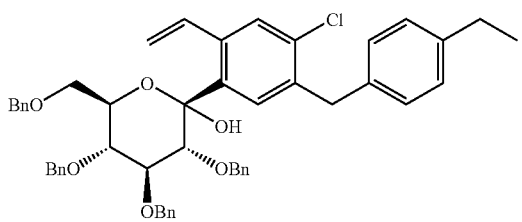

To a stirred −78° C. solution of 1-bromo-4-chloro-5-(4-ethylbenzyl)-2-vinylbenzene (0.075 g, 0.246 mmol) in 1.5 mL of 1:2 dry THF:toluene under Ar, was added 0.1 mL of 2.5M n-BuLi in hexane (pre-cooled to −78° C.) dropwise to insure the temperature remained below −70° C. After being stirred for 40 min at −78° C., following the addition, the mixture was transferred by cannula to a stirred −78° C. solution of 2,3,4,6-tetra-O-benzyl-β-D-glucolactone (0.145 g, 0.268 mmol) in 1.2 mL of toluene at a rate that maintained the reaction below −70° C. The reaction mixture was stirred for 3.5 h at −78° C. prior to quenching by addition of 1 mL of saturated NH₄Cl solution below −75° C. After complete addition, the reaction solution was gradually raised to room temperature and stirred overnight. The organic layer was separated and the aqueous layer was extracted 2× with EtOAc. The combined organic layers were washed with brine and dried over Na₂SO₄. Concentration under reduced pressure provided the crude product, which was purified by gel column chromotagraphy (EA:PE=1:5 as the eluant) to give 0.114 g of the title compound. $^1$H NMR (CDCl₃, 300 MHz): δ 7.56 (dd, J=17.2, 10.8 Hz, 1H), 7.54 (s, 1H), 7.43 (s, 1H), 7.34-7.29 (m, 14H), 7.26-7.19 (m, 2H), 7.15-7.12 (m, 2H), 7.07 (dd, 4H), 6.85 (d, 2H), 5.43 (d, J=17.2 Hz, 1H), 5.15 (d☐J=10.8 Hz, 1H), 4.90 (d, J=10.8 Hz, 1H), 4.85 (s, 2H), 4.65 (d, J=10.8 Hz, 1H), 4.58 (d, J=12 Hz, 1H), 4.46 (d, J=12 Hz, 1H), 4.35 (d, J=10.8 Hz, 1H), 4.12-3.98 (m, 5H), 3.89-3.86 (m, 3H), 3.70 (dd, J=10.2, 0.8 Hz, 1H), 2.60 (q, 2H), 1.19 (t, 3H).

Preparation of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran](Intermediate AU)

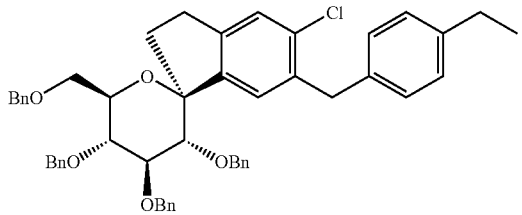

To a solution of (2S,3R,4S,5R,6R)-3,4,5-tris(benzyloxy)-6-(benzyloxymethyl)-2-(4-chloro-5-(4-ethylbenzyl)-2-vinylphenyl)tetrahydro-2H-pyran-2-ol (400 mg, 0.5 mmol) in CH₂Cl₂ (20 mL) was added Et₃SiH (1 mL) and BF₃.Et₂O (50 μL, 0.4 mmol) at −50° C. The mixture was stirred for 3 h at −50° C., then rised to −10° C. and stirred for another 3 h. The reaction was quenched by aqueous saturated NaHCO₃ (20 mL). The organic layer was separated, dried with Na₂SO₄ and concentrated in vacuo. The resulting residue was purified by preparative HPLC to give 160 mg (40%) of product as a colorless liquid. ¹H NMR (300 MHz, CDCl₃) δ 7.32-7.15 (m, 20H), 7.03 (m, 4H), 6.82 (m, 2H), 4.89 (m, 3H), 4.65 (d, J=10.8 Hz, 1H), 4.63 (d, J=12.3 Hz, 1H), 4.51 (d, J=12.3 Hz, 1H), 4.36 (d, J=10.5 Hz, 1H), 4.11 (d, J=15.6 Hz, 1H), 4.03 (d, J=15.3 Hz, 1H), 3.83-3.64 (m, 7H), 2.95 (dd, J=8.4, 5.7 Hz, 2H), 2.58 (dt, J=13.2, 8.7 Hz, 1H), 2.55 (q, J=7.5 Hz, 2H), 2.06 (dt, J=13.2, 8.7 Hz, 1H), 1.17 (t, J=7.5 Hz 3H); MS ESI (m/z) 779 (M+1)⁺, calc. 778.

Preparation of (1S,3'R,4'S,5'R,6'R)-5-chloro-6-(4-ethylbenzyl)-6'-(hydroxymethyl)-2,3,3',4',5',6'-hexahydrospiro[indene-1,2'-pyran]-3',4',5'-triol (Compound AV)

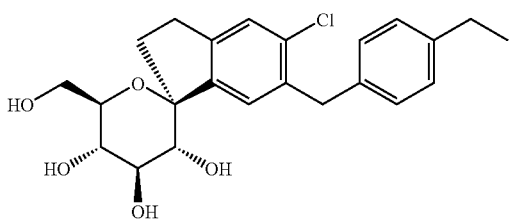

To a solution of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran] (120 mg, 0.15 mmol) in methanol (10 mL) was added Pd/C (40 mg, 30% wt). The mixture was stirred under hydrogen (1 atm) for 12 h at room temperature. It was filtered, and the filtrate was concentrated to give a residue, which was purified by preparative HPLC to provide 52 mg (81%) of product as a white solid. ¹H NMR (CD₃OD, 300 MHz): δ 7.25 (s, 1H), 7.23 (s, 1H), 7.09 (m, 4H), 4.05 (s, 2H), 3.80 (m, 1H), 3.64-3.34 (m, 5H), 2.93 (dd, J=7.8, 6.6 Hz, 2H), 2.58 (q, J=7.8 Hz, 2H), 2.53 (dt, J=13.2, 7.5 Hz, 1H), 2.11 (dt, J=13.2, 7.5 Hz, 1H), 1.19 (t, J=7.8 Hz, 3H); MS ESI (m/z) 419 (M+1)⁺, calc. 418.

Example 38

Preparation of (1S,3'R,4'S,5'S,6'S)-5-chloro-6-(4-ethylbenzyl)-6'-(fluoromethyl)-2,3,3',4',5',6'-hexahydrospiro[indene-1,2'-pyran]-3',4',5'-triol (Compound AW)

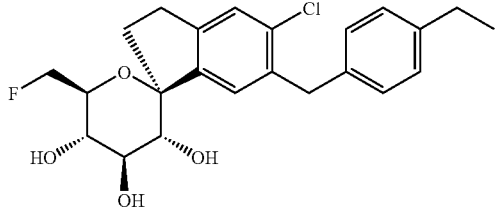

To a solution of (1S,3'R,4'S,5'S,6'R)-5-chloro-6-(4-ethylbenzyl)-6'-(hydroxymethyl)-2,3,3',4',5',6'-hexahydrospiro[indene-1,2'-pyran]-3',4',5'-triol (10 mg, 0.024 mmol) in CH₂Cl₂ (1 mL), was added DAST (9 μL, 0.072 mmol) at −78° C. The mixture was stirred for 30 min at −78° C., then allowed to warm to room temperature and stirred for another 3 h. The reaction was quenched by aqueous saturated NaHCO₃. The organic layer was separated, dried with Na₂SO₄ and concentrated in vacuo. The resulting residue was purified by preparative HPLC to give 4 mg (40%) of title compound as a colorless solid. ¹H NMR (CD₃OD, 300 MHz): δ 7.24 (s, 1H), 7.19 (s, 1H), 7.08 (m, 4H), 4.63 (d, J=3.3 Hz, 1H), 4.47 (d, J=3 Hz, 1H), 4.04 (m, 2H), 3.59-3.38 (m, 4H), 2.93 (t, J=7.2 Hz, 2H), 2.58 (q, J=7.8 Hz, 2H), 2.54 (dt, J=13.5, 7.8 Hz, 1H), 2.08 (dt, J=13.5, 7.8 Hz, 1H), 1.19 (t, J=7.8 Hz, 3H).

Example 39

Preparation of (1S,3'R,4'S,5'S,6'R)-5-chloro-6-(4-ethoxybenzyl)-6'-(hydroxymethyl)-2,3,3',4',5',6'-hexahydrospiro[indene-1,2'-pyran]-3',4',5'-triol (Compound AX)

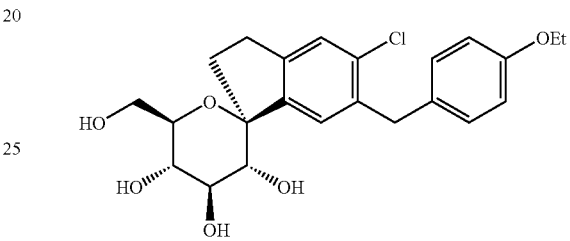

Compound AX was obtained starting from (1S,3'R,4'S,5'R,6'R)-3',4',5'-tris(benzyloxy)-6'-(benzyloxymethyl)-5-chloro-6-(4-ethoxybenzyl)-2,3,3',4',5',6'-hexahydrospiro[indene-1,2'-pyran] using methods analogous to those used to prepare compound AV. ¹H NMR (CD₃OD, 300 MHz): δ 7.23 (s, 2H), 7.09 (d, J=8.7 Hz, 2H), 6.83 (d, J=8.7 Hz, 2H), 4.03 (s, 2H), 3.98 (q, J=6.9 Hz, 2H), 3.80 (dd, J=11.7, 2.4 Hz, 1H), 3.64-3.32 (m, 5H), 2.93 (t, J=7.8 Hz, 2H), 2.54 (dt, J=12.9, 7.8 Hz, 1H), 2.11 (dt, J=12.9, 7.8 Hz, 1H), 1.35 (t, J=6.9 Hz, 3H); MS ESI (m/z) 452 (M+NH₄)⁺, calc. 434.

Example 40

Preparation of (1S,3'R,4'S,5'R,6'R)-3-allyl-3',4',5'-tris(benzyloxy)-6'-(benzyloxymethyl)-5-chloro-6-(4-ethylbenzyl)-2,3,3',4',5',6'-hexahydrospiro[indene-1,2'-pyran] (Intermediate AY)

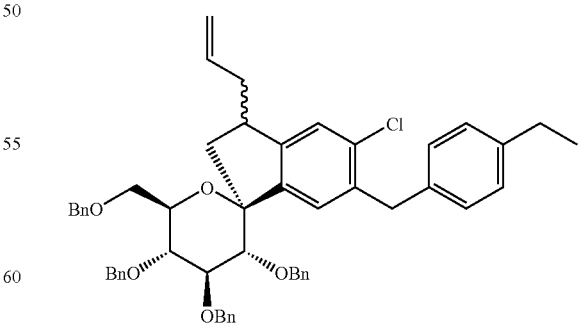

To a solution of (2S,3R,4S,5R,6R)-3,4,5-tris(benzyloxy)-6-(benzyloxymethyl)-2-(4-chloro-5-(4-ethylbenzyl)-2-vinylphenyl)tetrahydro-2H-pyran-2-ol (400 mg, 0.5 mmol) in CH₂Cl₂ (20 mL), were added allyl-TMS (1 mL) and BF$_3$.Et$_2$O (50 μL, 0.4 mmol) at −50° C. The mixture was stirred for 3 h at −50° C., then warmed to −10° C. and stirred for another 3 h. The reaction was quenched by aqueous saturated NaHCO$_3$ (20 mL). The organic layer was separated, dried with Na$_2$SO$_4$ and concentrated in vacuo. The resulting residue was purified by preparative HPLC to give 300 mg (72%) of the desired compound (the ratio of two diastereoisomers=2:1) as a colorless liquid. $^1$H NMR (CDCl$_3$, 300 MHz) δ 7.35-7.14 (m, 20H), 7.07-7.00 (m, 4H), 6.83-6.78 (m, 2H), 5.82 (m, 1H), 5.12-5.03 (m, 2H), 4.88 (m, 3H), 4.63 (d, J=10.8 Hz, 1H), 4.61 (d, J=12.3 Hz, 1H), 4.50 (d, J=12.3 Hz, 1H), 4.32 (d, J=10.8 Hz, 1H), 4.10 (d, J=15.3 Hz, 1H), 4.01 (d, J=15.3 Hz, 1H), 3.85-3.61 (m, 7H), 3.28 (m, 1H), 2.73 (dd, J=12.9, 7.8 Hz, 1H), 2.62 (m, 1H), 2.55 (q, J=7.8 Hz, 2H), 2.23 (m, 1H), 1.72 (dd, J=12.9, 7.8 Hz, 1H), 1.17 (t, J=7.8 Hz, 3H); MS ESI (m/z) 819 (M+1)$^+$, calc. 818.

Preparation of (1S,3'R,4'S,5'S,6'R)-5-chloro-6-(4-ethylbenzyl)-6'-(hydroxymethyl)-3-propyl-2,3,3',4',5',6'-hexahydrospiro[indene-1,2'-pyran]-3',4',5'-triol (Compound AZ)

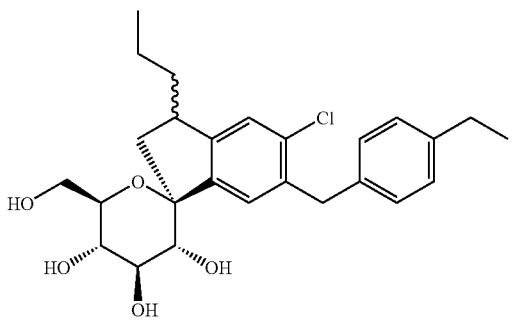

Compound AZ was synthesized using the standard hydrogenation procedure starting from intermediate AY. $^1$H NMR (CD$_3$OD, 300 MHz) δ 7.25 (s, 1H), 7.21 (s, 1H), 7.09 (m, 4H), 4.05 (s, 2H), 3.80 (m, 1H), 3.65-3.17 (m, 6H), 2.75 (dd, J=12.9, 7.8 Hz, 1H), 2.58 (q, J=7.8 Hz, 2H), 1.90 (m, 1H), 1.73 (dd, J=12.9, 7.8 Hz, 1H), 1.52-1.37 (m, 3H), 1.19 (t, J=7.8 Hz, 3H), 1.00 (m, 3H). MS ESI (m/z) 461 (M+1)$^+$, calc. 460.

Example 41

Preparation of (1S,3'R,4'S,5'S,6'R)-5-chloro-6-(4-ethylbenzyl)-3-(2-hydroxyethyl)-6'-(hydroxymethyl)-2,3,3',4',5',6'-hexahydrospiro[indene-1,2'-pyran]-3',4',5'-triol (Compound BA)

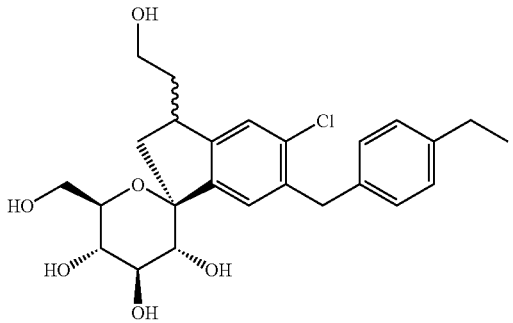

O$_3$ was bubbled into a cooled solution (−78° C.) of (1S,3'R,4'S,5'R,6'R)-3-allyl-3',4',5'-tris(benzyloxy)-6'-(benzyloxymethyl)-5-chloro-6-(4-ethylbenzyl)-2,3,3',4',5',6'-hexahydrospiro[indene-1,2'-pyran] (100 mg, 0.12 mmol) in CH$_2$Cl$_2$ (20 mL). After 5 min, N$_2$ was bubbled into this solution for 20 min while the reaction temperature was gradually raised to room temperature. PPh$_3$ (50 mg, 0.24 mmol) was added and the resulting mixture was stirred for 1 h at room temperature and concentrated. The resulting crude aldehyde was dissolved in THF (20 mL), and NaBH$_4$ (9 mg, 0.24 mmol) was added. After being stirred at room temperature for 2 h, the reaction mixture was quenched by saturated aqueous NH$_4$Cl solution and concentrated. The residue was partitioned between water and AcOEt, the organic layer was separated, washed with brine and dried over Na$_2$SO$_4$. Concentration and purification by preparative HPLC gave 85 mg (95%) of tetrabenzyl-protected alcohol, which was deprotected using the standard hydrogenation procedure to provide the title compound (30 mg). $^1$H NMR (CD$_3$OD, 300 MHz) δ 7.26 (s, 1H), 7.24 (s, 1H), 7.09 (m, 4H), 4.05 (s, 2H), 3.82-3.21 (m, 9H), 2.77 (dd, J=12.9, 7.8 Hz, 1H), 2.58 (q, J=7.8 Hz, 2H), 2.13 (m, 1H), 1.77 (dd, J=12.9, 7.8 Hz, 1H), 1.68 (m, 1H), 1.19 (t, J=7.8 Hz, 3H); MS ESI (m/z) 463 (M+1)$^+$, calc. 460.

Example 42

Preparation of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran]-3-ol (Intermediate BB1)

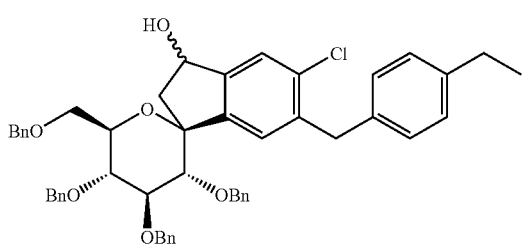

To (2S,3R,4S,5R,6R)-3,4,5-tris(benzyloxy)-6-(benzyloxymethyl)-2-(4-chloro-5-(4-ethylbenzyl)-2-vinylphenyl)tetrahydro-2H-pyran-2-ol (120 mg, 0.15 mmol) was added TFA (1.5 mL) at −10° C. After the reaction mixture was stirred for 6 h, the solvent was removed under vacuum and aqueous saturated NaHCO$_3$ (10 mL) was added to the residue. The aqueous layer was extracted with EtOAc (10 mL×3). The combined organic layers were washed with brine and dried over Na$_2$SO$_4$. Removal of the solvent afforded the crude product, which was dissolved in 1.9 mL of a mixture of THF:CH$_3$OH:H$_2$O (2:3:1) followed by addition of 6 mg of LiOH.H$_2$O at room temperature. After stirring for 2 h, the volatiles were removed using a rotary evaporator. The residue, after being dissolved in ethyl acetate, was washed with brine (10 mL×2), 5% aqueous KHSO$_4$ (10 mL) and finally with brine (10 mL) prior to drying over Na$_2$SO$_4$. The volatiles were removed and the resulting oil was purified by preparative TLC to obtain 44 mg of the title product.

61

Preparation of (1S,3'R,4'S,5'S,6'R)-5-chloro-6-(4-ethylbenzyl)-6'-(hydroxymethyl)-2,3,3',4',5',6'-hexahydrospiro[indene-1,2'-pyran]-3,3',4',5'-tetraol (Compound BB)

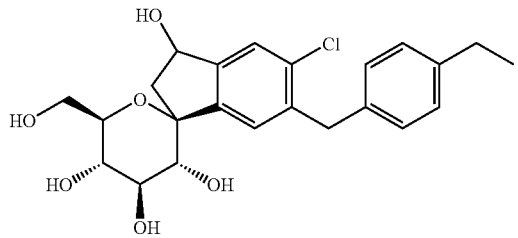

Compound BB was synthesized using the standard hydrogenation procedure starting from intermediate (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran]-3-ol. $^1$H NMR (CD$_3$OD, 300 MHz) δ 7.38 (s, 1H), 7.32 (s, 1H), 7.12-7.05 (m, 4H), 5.12 (t, J=6.9 Hz, 1H), 4.09 (dd, J=12.6 Hz, 2H), 3.85-3.80 (m, 1H), 3.66~3.60 (m, 1H), 3.57-3.34 (m, 4H), 3.00 (dd, J=12.9, 7.5 Hz, 1H), 2.58 (q, 2H), 1.87 (dd, J=13.2, 6.6 Hz, 1H), 1.18 (t, 3H).

Example 43

Preparation of (1S,3'R,4'S,5'S,6'R)-3',4',5'-tris(benzyloxy)-6'-(benzyloxymethyl)-5-chloro-6-(4-ethylbenzyl)-3',4',5',6'-tetrahydrospiro[indene-1,2'-pyran]-3(2H)-one (Intermediate BC1)

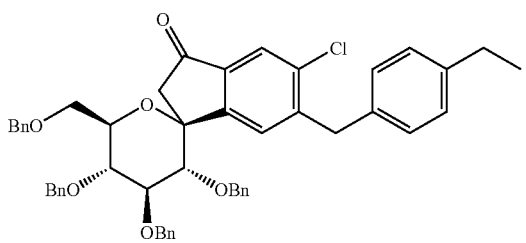

To a 0° C. solution of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran]-3-ol (40 mg, 0.05 mmol) in dry dichloromethane (1.0 mL) was added dropwise a solution of Dess-Martin reagent (43 mg, 0.1 mmol) in 0.5 mL of dry dichloromethane. The reaction mixture was stirred for 3.5 h at room temperature and quenched by addition of 2 mL of 1 M aqueous NaOH solution when TLC showed the reaction was complete. The organic layer was separated and the aqueous layer was extracted 2× with CH$_2$Cl$_2$ (10 mL). The combined organic layers were washed 1× with NaHSO$_3$ (10 mL), 2× with NaHCO$_3$ (10 mL), 3× with brine (10 mL) prior to drying over anhydrous Na$_2$SO$_4$. Concentration under reduced pressure and purification of the crude product by preparative TLC provided 36 mg of the pure product.

62

Preparation of (1S,3'R,4'S,5'S,6'R)-5-chloro-6-(4-ethylbenzyl)-3',4',5'-trihydroxy-6'-(hydroxymethyl)-3',4',5',6'-tetrahydrospiro[indene-1,2'-pyran]-3(2H)-one (Compound BC)

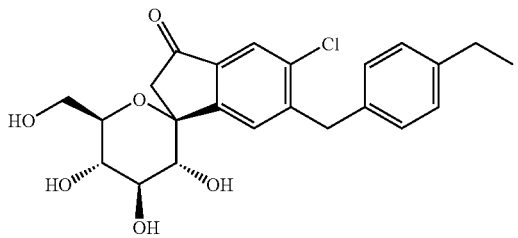

Compound BC was synthesized using the standard hydrogenation procedure starting from intermediate (1S,3'R,4'S,5'R,6'R)-3',4',5'-tris(benzyloxy)-6'-(benzyloxymethyl)-5-chloro-6-(4-ethylbenzyl)-3',4',5',6'-tetrahydrospiro[indene-1,2'-pyran]-3(2H)-one. $^1$H NMR (CD$_3$OD, 300 MHz) δ 7.63 (s, 1H), 7.60 (s, 1H)), 7.08-7.03 (m, 4H), 4.12 (s, 2H), 3.80-3.77 (m, 1H), 3.63-3.53 (m, 2H), 3.41-3.34 (m, 3H), 3.98 (d, J=13.2 Hz, 1H), 2.63 (d, J=13.2 Hz, 1H), 2.56 (q, 2H), 1.13 (t, 3H).

Example 44

Preparation of (1S,3'R,4'S,5'R,6'R)-3',4',5'-tris(benzyloxy)-6'-(benzyloxymethyl)-5-chloro-6-(4-ethylbenzyl)-3-methoxy-2,3,3',4',5',6'-hexahydrospiro[indene-1,2'-pyran] (Intermediate BD1)

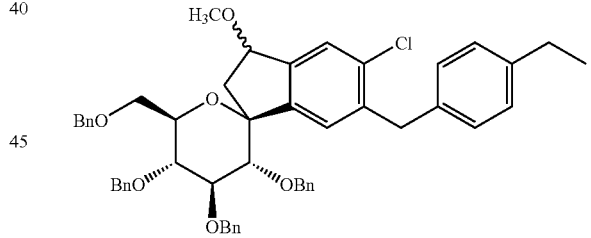

To a solution of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran]-3-ol (26 mg, 0.032 mmol) in dry THF (0.8 mL) was added NaH (1.5 mg, 0.036 mmol, 60%) and CH$_3$I (3.1 µL, 0.049 mmol) at room temperature. The reaction mixture was stirred for 3 h and quenched by addition of 5 mL of water when TLC showed the reaction was complete. Ethyl acetate (10 mL) was added to the mixture and the organic layer was separated. The aqueous layer was extracted 2× with ethyl acetate (10 mL). The combined organic layers were washed 1× with 10% HCl (10 mL), 2× with water (10 mL), 2× with brine (10 mL) prior to drying over anhydrous Na$_2$SO$_4$. Concentration under reduced pressure and purification of the crude product by prepared TLC provided 22 mg of the pure product.

Preparation of (1S,3'R,4'S,5'S,6'R)-5-chloro-6-(4-ethylbenzyl)-6'-(hydroxymethyl)-3-methoxy-2,3,3',4',5',6'-hexahydrospiro[indene-1,2'-pyran]-3',4',5'-triol (Compound BD)

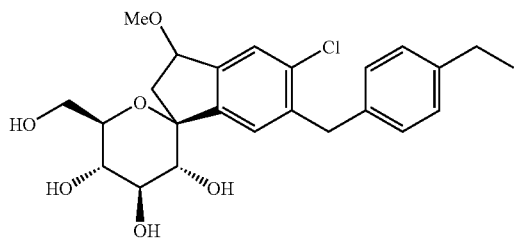

Compound BD was synthesized using the standard hydrogenation procedure starting from intermediate (1S,3'R,4'S,5'R,6'R)-3',4',5'-tris(benzyloxy)-6'-(benzyloxymethyl)-5-chloro-6-(4-ethylbenzyl)-3-methoxy-2,3,3',4',5',6'-hexahydrospiro[indene-1,2'-pyran]. $^1$H NMR (CD$_3$OD, 300 MHz) δ 7.36 (s, 1H), 7.33 (s, 1H), 7.11-7.05 (m, 4H), 4.87 (t, J=6.6 Hz, 1H), 4.08 (dd, J=18.2 Hz, 2H), 3.84-3.79 (m, 1H), 3.66-3.50 (m, 2H), 3.56-3.36 (m, 6H), 3.03 (dd, J=12.6, 7.2 Hz, 1H), 2.58 (q, 2H), 1.90 (dd, J=12.6, 6.3 Hz, 1H), 1.19 (t, 3H).

Example 45

Preparation of (1S,3'R,4'S,5'R,6'R)-3',4',5'-tris(benzyloxy)-6'-(benzyloxymethyl)-5-chloro-6-(4-ethylbenzyl)-3-fluoro-2,3,3',4',5',6'-hexahydrospiro[indene-1,2'-pyran] (Intermediate BE1)

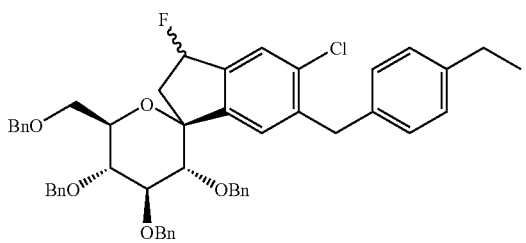

To a −78° C. solution of (1S,3'R,4'S,5'R,6'R)-3',4',5'-tris(benzyloxy)-6'-(benzyloxymethyl)-5-chloro-6-(4-ethylbenzyl)-2,3,3',4',5',6'-hexahydrospiro[indene-1,2'-pyran]-3-ol (40 mg, 0.05 mmol) in dry dichloromethane (2.0 mL) was added dropwise a solution of DAST reagent (0.014 mL, 0.1 mmol, 95%) in 0.5 mL of dry dichloromethane. The reaction mixture was stirred for 2 h at −78° C. and quenched by addition of 1 mL of saturated aqueous NaHCO$_3$ solution when TLC showed the reaction was complete. The organic layer was separated and the aqueous layer was extracted 2× with CH$_2$Cl$_2$ (10 mL). The combined organic layers were washed 2× with NaHCO$_3$ (10 mL), 3× with brine (10 mL) prior to drying over anhydrous Na$_2$SO$_4$. Concentrated under reduced pressure and purification of the crude product by prepared TLC provided 35 mg of the pure product.

Preparation of (1S,3'R,4'S,5'S,6'R)-5-chloro-6-(4-ethylbenzyl)-3-fluoro-6'-(hydroxymethyl)-2,3,3',4',5',6'-hexahydrospiro[indene-1,2'-pyran]-3',4',5'-triol

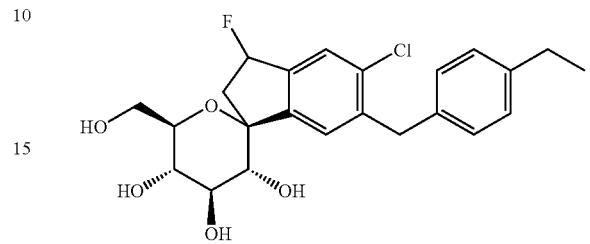

Compound BE was synthesized using the standard hydrogenation procedure starting from intermediate (1S,3'R,4'S,5'R,6'R)-3',4',5'-tris(benzyloxy)-6'-(benzyloxymethyl)-5-chloro-6-(4-ethylbenzyl)-3-fluoro-2,3,3',4',5',6'-hexahydrospiro[indene-1,2'-pyran]. $^1$H NMR (CD$_3$OD, 300 MHz) δ 7.43 (s, 1H), 7.38 (s, 1H), 7.16-7.09 (m, 4H), 6.90 (dt, 1H), 4.10 (dd, J=19.2 Hz, 2H), 3.85-3.80 (m, 1H), 3.68~3.62 (m, 1H), 3.54-3.30 (m, 4H), 3.08 (ddd, J=14.1, 7.2, 5.4 Hz, 1H), 2.59 (q, 2H), 2.12 (ddd, J=27.9, 13.2, 5.7 Hz, 1H), 1.19 (t, 3H).

Example 46

Preparation of (1S,3'R,4'S,5'S,6'R)-5-chloro-6-(4-ethoxybenzyl)-3-fluoro-6'-(hydroxymethyl)-2,3,3',4',5',6'-hexahydrospiro[indene-1,2'-pyran]-3',4',5'-triol (Compound BF)

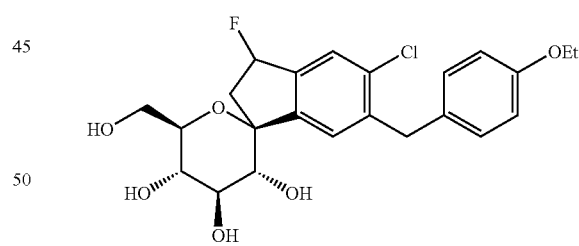

Compound BF was synthesized using the standard hydrogenation procedure starting from intermediate (1S,3'R,4'S,5'R,6'R)-3-fluoro-3',4',5'-tris(benzyloxy)-6'-(benzyloxymethyl)-5-chloro-6-(4-ethoxybenzyl)-2,3,3',4',5',6'-hexahydrospiro[indene-1,2'-pyran]. $^1$H NMR (CD$_3$OD, 300 MHz) δ 7.43 (s, 1H), 7.37 (s, 1H), 7.12-7.10 (m, 2H), 6.82-6.77 (m, 2H), 6.00 (dt, 1H), 4.06 (d, J=20.1 Hz, 2H), 4.02-3.95 (m, 2H), 3.85-3.81 (m, 1H), 3.69-3.63 (m, 1H), 3.55-3.00 (m, 4H), 3.09 (ddd, J=13.2, 7.2, 6.0 Hz, 1H), 2.12 (ddd, J=28.2, 13.5, 5.7 Hz, 1H), 1.35 (t, 3H).

Example 47

Preparation of (1S,3'R,4'S,5'S,6'R)-5-chloro-6'-(hydroxymethyl)-6-(4-((S)-tetrahydrofuran-3-yloxy)benzyl)-2,3,3',4',5',6'-hexahydrospiro[indene-1,2'-pyran]-3',4',5'-triol (Compound BG)

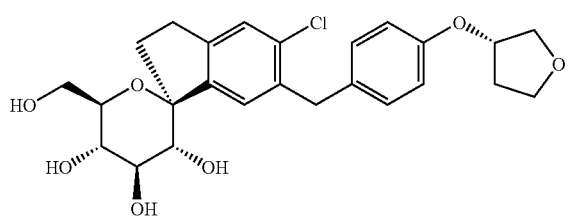

Compound BG was obtained starting from (2S,3R,4S,5R,6R)-2-(5-((S)-4-((S)-tetrahydrofuran-3-yloxy)benzyl)-4-chloro-2-vinylphenyl)-3,4,5-tris(benzyloxy)-6-(benzyloxymethyl)-tetrahydro-2H-pyran-2-ol using methods analogous to those used to prepare compound AV, followed by hydrogenation. $^1$H NMR (CD$_3$OD, 300 MHz) δ 7.25 (s, 1H), 7.23 (s, 1H), 7.11 (d, 2H), 6.79 (d, 2H), 4.99-4.94 (m, 1H), 4.02 (s, 2H), 3.96-3.78 (m, 5H), 3.65-3.50 (m, 4H), 3.47-3.41 (m, 1H), 3.37-3.33 (m, 1H), 2.94 (t, 2H), 2.59-2.50 (m, 1H), 2.27-2.03 (m, 3H); MS ESI (m/z) 521 (M+45)$^-$, calc. 476.

Example 48

Preparation of ((1S,3'R,4'S,5'S,6'R)-5-chloro-6-(4-ethylbenzyl)-3',4',5'-trihydroxy-2,3,3',4',5',6'-hexahydrospiro[indene-1,2'-pyran]-6'-yl)methyl methyl carbonate (Compound BH)

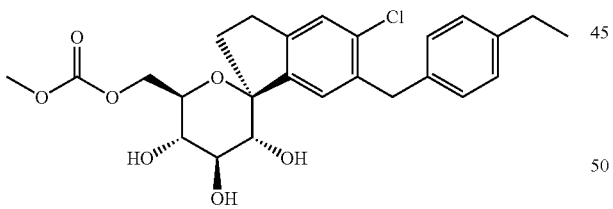

A solution of methyl chloroformate (114 mg, 1.20 mmol) in CH$_2$Cl$_2$ (0.5 mL) was added dropwise to a solution of (1S,3'R,4'S,5'S,6'R)-5-chloro-6-(4-ethylbenzyl)-6'-(hydroxymethyl)-2,3,3',4',5',6'-hexahydrospiro[indene-1,2'-pyran]-3',4',5'-triol (compound AV) (418 mg, 1.00 mmol) in 2,4,6-collidine (5 mL) at −40° C. The whole was stirred at −40° C. for 1 h and at room temperature for 1.5 h. The reaction mixture was poured into ice-cooled 10% HCl and extracted with AcOEt. The organic layer was washed with saturated NaHCO$_3$ and brine, dried over MgSO$_4$, and evaporated. The residue was chromatographed on silica gel to give the acylated product BH (420 mg, 87%). $^1$H NMR (CD$_3$OD, 300 MHz) δ 7.25 (s, 1H), 7.23 (s, 1H), 7.09 (m, 4H), 4.05 (s, 2H), 3.80 (m, 1H), 3.65 (s, 3H), 3.62-3.34 (m, 5H), 2.91 (dd, J=6.6, 7.8 Hz, 2H), 2.60 (q, J=7.8 Hz, 2H), 2.55 (dt, J=7.5, 13.2 Hz, 1H), 2.10 (dt, J=7.5, 13.2 Hz, 1H), 1.20 (t, J=7.8 Hz, 3H); MS ESI m/e 477 (M+1).

Example 49

Preparation of ((1S,3'R,4'S,5'S,6'R)-5-chloro-6-(4-ethylbenzyl)-3',4',5'-trihydroxy-2,3,3',4',5',6'-hexahydrospiro[indene-1,2'-pyran]-6'-yl)methyl ethyl carbonate (Compound BI)

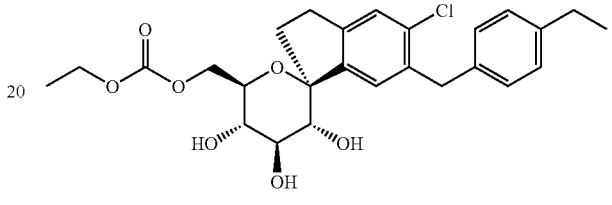

Compound BI was prepared from compound AV and ethyl chloroformate using methods analogous to those described above for compound BH in Example 48; yield: 43%. $^1$H NMR (CD$_3$OD, 300 MHz) δ 7.25 (s, 1H), 7.23 (s, 1H), 7.09 (m, 4H), 4.02 (q, J=7.2 Hz, 2H), 4.05 (s, 2H), 3.80 (m, 1H), 3.62-3.34 (m, 5H), 2.91 (dd, J=6.6, 7.8 Hz, 2H), 2.60 (q, J=7.8 Hz, 2H), 2.55 (dt, J=7.5, 13.2 Hz, 1H), 2.10 (dt, J=7.5, 13.2 Hz, 1H), 1.20 (t, J=7.8 Hz, 3H), 1.15 (t, 3H, J=7.2 Hz); MS ESI m/e 491 (M+1).

Example 50

Preparation of ((1S,3'R,4'S,5'S,6'R)-5-chloro-6-(4-ethoxybenzyl)-3',4',5'-trihydroxy-2,3,3',4',5',6'-hexahydrospiro[indene-1,2'-pyran]-6'-yl)methyl isopropyl carbonate (Compound BJ)

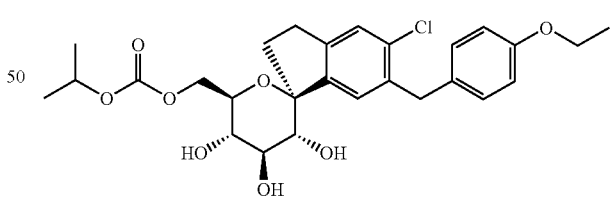

Compound BJ was prepared from compound AX and isopropyl chloroformate using methods analogous to those described above for compound BH in Example 48. $^1$H NMR (CD$_3$OD, 300 MHz) δ 7.24 (s, 2H), 7.09 (d, J=8.7 Hz, 2H), 6.83 (d, J=8.7 Hz, 2H), 4.73 (m, 1H), 4.02 (s, 2H), 3.98 (q, J=6.9 Hz, 2H), 3.80 (dd, J=11.7, 2.4 Hz, 1H), 3.64-3.32 (m, 5H), 2.93 (t, J=7.8 Hz, 2H), 2.54 (dt, J=12.9, 7.8 Hz, 1H), 2.11 (dt, J=12.9, 7.8 Hz, 1H), 1.35 (t, J=6.9 Hz, 3H), 1.18 (d, J=6.5 Hz, 3H), 1.15 (d, J=6.5 Hz, 3H); MS ESI (m/z) 521 (M+H)$^+$.

Example 51

Preparation of (((1S,3'R,4'S,5'S,6'R)-5-chloro-6-(4-ethoxybenzyl)-3',4',5'-trihydroxy-2,3,3',4',5',6'-hexahydrospiro[indene-1,2'-pyran]-6'-yl)methyl 3,3-dimethylbutanoate (Compound BK)

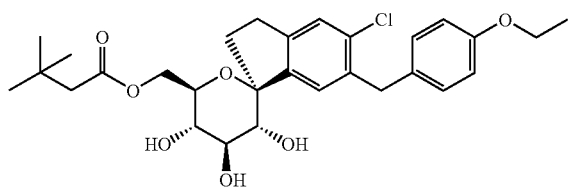

Compound BK was prepared from compound AX and 3,3-dimethylbutanoyl chloride using methods analogous to those described above for compound BH in Example 48. $^1$H NMR (CD$_3$OD, 300 MHz) δ 7.23 (s, 2H), 7.09 (d, J=8.7 Hz, 2H), 6.83 (d, J=8.7 Hz, 2H), 4.03 (s, 2H), 3.98 (q, J=6.9 Hz, 2H), 3.80 (dd, J=11.7, 2.4 Hz, 1H), 3.64-3.32 (m, 5H), 2.93 (t, J=7.8 Hz, 2H), 2.54 (dt, J=12.9, 7.8 Hz, 1H), 2.20 (s, 2H), 2.11 (dt, J=12.9, 7.8 Hz, 1H), 1.35 (t, J=6.9 Hz, 3H); 1.10 (s, 9H); MS ESI (m/z) 533 (M+H)$^+$.

Example 52

The SGLT inhibitory effects of the compounds of the present invention were demonstrated by the following procedures.

Preparation of Human SGLT2 Expression Vector

A full-length cDNA clone expressing human SGLT2 (GenScript Corporation) was subcloned into Hind III and Not I sites of pEAK15 expression vector. Clones harboring the cDNA inserts were identified by restriction analysis.

Preparation of a Cell Line Stably Expressing Human SGLT2

Plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% CO$_2$ for 24 h. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D-[U-$^{14}$C]glucopyranoside uptake assay described below. The clone that exhibited the highest signal-to-background ratio was used for the methyl-α-D-[U-$^{14}$C]glucopyranoside uptake assay.

Preparation of Human SGLT1 Expressing Cells

Full-length human SGLT1 cDNA on pDream2.1 expression vector was obtained from GenScript Corporation and propagated in *Escherichia coli* strain DH5α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U-$^{14}$C]glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 100 μl medium) incubated at 37° C. under 5% CO$_2$ for 48 h prior to the assay. Cells were washed twice with 150 μl of either sodium buffer (137 mM NaCl, 5.4 mM KCl, 2.8 mM CaCl$_2$, 1.2 mM MgCl$_2$, 10 mM tris(hydroxymethyl)aminomethane/N-2-hydroxyethylpiperazine-N'-ethanesulfonic acid [Tris/Hepes], pH 7.2) or sodium-free buffer (137 mM N-methyl-glucamine, 5.4 mM KCl, 2.8 mM CaCl$_2$, 1.2 mM MgCl$_2$, 10 mM Tris/Hepes, pH 7.2). Test compound in 50 μl each of sodium or sodium-free buffer containing 40 μCi/ml methyl-α-D-[U-$^{14}$C]glucopyranoside (Amersham Biosciences/GE Healthcare) was added per well of a 96-well plate and incubated at 37° C. with shaking for either 2 h (SGLT1 assay) or 1.5 h (SGLT2 assay). Cells were washed twice with 150 μl of wash buffer (137 mM N-methylglucamine, 10 mM Tris/Hepes, pH 7.2) and methyl-α-D-[U-$^{14}$C]glucopyranoside uptake was quantitated using a TopCount scintillation counter (PerkinElmer, Inc.). Sodium-dependent glucopyranoside uptake was measured by subtracting the values obtained with sodium-free buffer from those obtained using sodium buffer (average of triplicate determinations).

TABLE 1

| | IC$_{50}$* | |
| Compound | SGLT2 | SGLT1 |
| --- | --- | --- |
| G | + | +++ |
| H | + | ++ |
| K | + | + |
| AG | + | ++ |
| AH | + | ++ |
| AI | + | +++ |
| AM | + | ++ |
| AQ | + | +++ |
| AV | + | ++ |
| BA | + | +++ |
| BB | + | +++ |
| BD | + | +++ |
| BE | + | +++ |
| BG | + | +++ |

*Key:
+ <1 μM
++ 1 μM to 10 μM
+++ >10 μM

TABLE 2

| Compound | SGLT2 IC$_{50}$ (nM) |
| --- | --- |
| G | 71 |
| H | 5.1 |

What is claimed is:

1. A compound of Formula I:

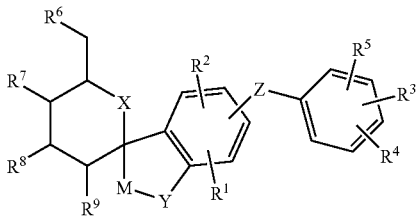

wherein

M is a member selected from the group consisting of methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy; and $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; or optionally, M represents a single bond;

X is a member selected from the group consisting of oxygen; sulfur; SO; $SO_2$; methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy; $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; and NH optionally substituted with a substituent independently selected from $C_1$-$C_6$ alkyl, $C_3$-$C_6$ cycloalkyl and ($C_1$-$C_4$ alkyl)carbonyl;

Y is a member selected from the group consisting of $(CH_2)_n$; $(CH_2)_m CH=CH$; $CH=CH(CH_2)_m$; $CH_2CH=CHCH_2$; $(CH_2)_m C(O)$; $C(O)(CH_2)_m$; and $(O)C(CH_2)_m C(O)$; wherein n is an integer from 1 to 3, m is an integer from 0 to 2, and each hydrogen independently is optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy;

Z is a member selected from the group consisting of oxygen; sulfur; SO; $SO_2$; 1,1-cyclopropylene; carbonyl; and methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$) alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, aryl, heteroaryl, ($C_1$-$C_4$ alkyl)carbonyl, arylcarbonyl, heteroarylcarbonyl, hydroxycarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups or portions are optionally partly or completely fluorinated and optionally mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group is optionally replaced by CO or $SO_2$;

$R^2$ is a member selected from the group consisting of hydrogen, halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano and nitro, wherein alkyl groups or portions are optionally mono- or polysubstituted by fluorine, or in the event that $R^1$ and $R^2$ are bound to two adjacent C atoms of the phenyl ring, $R^1$ and $R^2$ are optionally joined together such that $R^1$ and $R^2$ together form a $C_3$-$C_5$ alkylene, $C_3$-$C_5$ alkenylene or butadienylene bridge, which is optionally partly or completely fluorinated and optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups are optionally replaced by an N atom;

$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$) alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_3$-$C_{10}$ cycloalkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_3$-$C_{10}$ cycloalkyl)$C_2$-$C_4$ alkenyl, $C_3$-$C_6$ cycloalkylidenmethyl, aryl, heteroaryl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl) piperazin-1-ylcarbonyl, hydroxycarbonyl, ($C_1$-$C_4$ alkyloxy)carbonyl, alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl) carbonylamino, arylcarbonylamino, heteroaryl-carbonylamino, $C_1$-$C_4$ alkylsulfonylamino, arylsulfonylamino, $C_1$-$C_6$ alkyloxy, $C_3$-$C_{10}$ cycloalkyloxy, $C_5$-$C_7$ cycloalkenyloxy, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, amino, hydroxy, cyano or nitro, wherein alkyl, alkenyl, alkynyl, cycloalkyl and cycloalkenyl groups or portions are optionally partly or completely fluorinated and optionally mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group is optionally replaced by CO or $SO_2$;

$R^4$ is a member selected from the group consisting of hydrogen, halo, hydroxy, cyano, nitro, $C_1$-$C_3$ alkyl, $C_3$-$C_{10}$ cycloalkyl, $C_3$-$C_{10}$ cycloalkyloxy and $C_1$-$C_3$ alkyloxy, wherein alkyl groups or portions may be mono- or polysubstituted by fluorine, or if $R^3$ and $R^4$ are bound to two adjacent C atoms of the phenyl ring, $R^3$ and $R^4$ are optionally joined together such that $R^3$ and $R^4$ together form a $C_3$-$C_5$ alkylene, $C_3$-$C_5$ alkenylene or butadienylene bridge, which is optionally partly or completely fluorinated and optionally mono- or disubstituted by identical or different substituents selected from chlorine, hydroxy, $C_1$-$C_3$ alkoxy and $C_1$-$C_3$ alkyl, and wherein one or two methylene groups can be replaced independently of one another by O, S, CO, SO, $SO_2$ or $NR^a$, and wherein in the case of a butadienylene bridge one or two methyne groups are optionally replaced by an N atom;

$R^5$ is a member selected from the group consisting of hydrogen, halo, hydroxy, cyano, nitro, $C_1$-$C_3$ alkyl, $C_3$-$C_{10}$ cycloalkyl and $C_1$-$C_3$ alkyloxy, wherein alkyl groups or portions may be mono- or polysubstituted by fluorine; and $R^6$, $R^7$, $R^8$ and $R^9$ are each members independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$) alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$)cycloalkenyloxy-($C_1$-$C_3$) alkyl, aryloxy-($C_1$-$C_3$)alkyl, heteroaryloxy-($C_1$-$C_3$) alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy, and cyano, wherein alkyl, alkenyl, alkynyl, cycloalkyl and cycloalkenyl groups or portions are optionally partly or completely fluorinated and optionally mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^a$, O, S, CO, SO or $SO_2$;

$R^a$ is a member selected from the group consisting of H, $C_1$-$C_4$ alkyl and $C_1$-$C_4$ alkylcarbonyl; and pharmaceutically acceptable salts thereof.

2. A compound of claim 1, wherein X is O.

3. A compound of claim 1, wherein M is $CH_2$.

4. A compound of claim 1, wherein Y is $CH_2$ or C(O).

5. A compound of claim 1, wherein Z is selected from the group consisting of methylene, 1,1-cyclopropylene, methylmethylene, fluoromethylene, dimethylmethylene, difluoromethylene and fluoromethylmethylene.

6. A compound of claim 1, wherein at least one of $R^6$, $R^7$, $R^8$ and $R^9$ is hydroxy.

7. A compound of claim 1, wherein at least two of $R^6$, $R^7$, $R^8$ and $R^9$ are hydroxy.

8. A compound of claim 1, wherein M is $CH_1$; X is O; Y is $CH_2$ or C(O); Z is selected from the group consisting of methylene, 1,1-cyclopropylene, methylmethylene, fluoromethylene, dimethylmethylene, difluoromethylene and fluoromethylmethylene; and at least two of $R^6$, $R^7$, $R^8$ and $R^9$ are hydroxy.

9. A compound of claim 1, wherein M is $CH_2$; X is O; Y is selected from the group consisting of $CH_2$ optionally substituted with $C_1$-$C_6$ alkyl or $C_1$-$C_6$ alkoxy, and C(O); Z is selected from the group consisting of methylene, 1,1-cyclopropylene, methylmethylene, fluoromethylene, dimethylmethylene, difluoromethylene and fluoromethylmethylene; and at least two of $R^6$, $R^7$, $R^8$ and $R^9$ are hydroxy.

10. A compound having the formula:

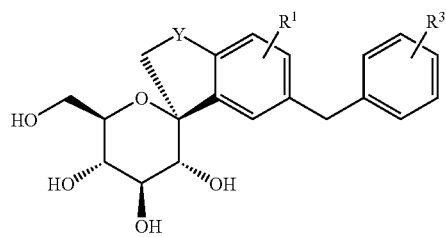

IA wherein

Y is selected from the group consisting of $(CH_2)_n$, $(CH_2)_m$CH=CH, CH=CH$(CH_2)_m$ and $CH_2$CH=CHCH$_2$, wherein n is an integer from 1 to 3, m is an integer from 0 to 2, and each hydrogen independently may be optionally replaced with a substituent independently selected from halo, $C_1$-$C_6$ alkyl, $C_1$-$C_6$ alkoxy, $C_3$-$C_6$ cycloalkyl and $C_3$-$C_6$ cycloalkyloxy;

$R^1$ is selected from the group consisting of hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano and nitro; and $R^3$ is selected from the group consisting of hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano and nitro, wherein in cycloalkyl groups or portions, one or two methylene groups are optionally replaced independently of one another by O, S, CO, SO or $SO_2$.

11. A pharmaceutical composition comprising a compound of claim 1 in a pharmaceutically acceptable carrier.

12. A pharmaceutical composition comprising a compound of claim 1 and at least one therapeutic agent selected from the group consisting of an antidiabetic agent, a lipid-lowering/lipid-modulating agent, an agent for treating diabetic complications, an anti-obesity agent, an antihypertensive agent, an antihyperuricemic agent, and an agent for treating chronic heart failure or atherosclerosis.

13. The pharmaceutical combination of claim 12, wherein the therapeutic agent is at least one antidiabetic agent.

14. The pharmaceutical combination of claim 13, wherein the antidiabetic agent is at least one agent selected from the group consisting of insulin, a sulfonylurea, an insulin secretion enhancer, a biguanide, a sulfonylurea/biguanide combination, a meglitinide, a thiazolidinedione, a thiazolidinedione/biguanide combination, an oxadiazolidinedione, a PPAR-gamma agonist, a PPAR-alpha/gamma dual agonist, a PPAR-alpha/gamma/delta pan agonist, a retinoid X receptor agonist, an alpha-glucosidase inhibitor, a stimulant of insulin receptor tyrosine kinase, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose 1,6-bisphosphatase inhibitor, a pyruvate dehydrogenase inhibitor, an imidazoline derivative, a hepatic gluconeogenesis inhibitor, D-chiroinositol, a glycogen synthase kinase-3 inhibitor, an incretin mimetic, a glucagon receptor antagonist, GLP-1, a GLP-1 analog, a GLP-1 receptor agonist, amylin, an amylin analog or agonist, an aP2 inhibitor, a beta-3 adrenergic receptor agonist and an insulin sensitivity enhancer.

15. The pharmaceutical combination of claim 14, wherein the antidiabetic agent is at least one agent selected from the group consisting of insulin, metformin, glyburide, glimepiride, glipyride, glipizide, chlorpropamide, gliclazide, acarbose, miglitol, pioglitazone, rosiglitazone, isaglitazone, netoglitazone, rivoglitazone, repaglinide, nateglinide, exenatide, muraglitazar, naveglitazar, tesaglitazar, peliglitazar, farglitazar, metaglidasen, sitagliptin, vildagliptin, denagliptin, saxagliptin, solabegron and pramlintide.

16. The pharmaceutical combination of claim 12, wherein the therapeutic agent is at least one anti-obesity agent selected from the group consisting of a serotonin-norepinephrine reuptake inhibitor, a norepinephrine-dopamine reuptake inhibitor, a selective serotonin reuptake inhibitor, a selective norepinephrine reuptake inhibitor, a norepinephrine releasing stimulant, an anorexiant, a dopamine agonist, an H3-histamine antagonist, a 5-HT2c receptor agonist, a beta-3 adrenergic receptor agonist, a cholecystokinin agonist, a lipase inhibitor, an antidepressant/acetylcholinesterase inhibitor combination, a gamma-aminobutyric acid receptor antagonist, leptin, a leptin analog or leptin receptor agonist, an NPY receptor antagonist or modulator, ciliary neurotrophic factor, a thyroid hormone receptor-beta agonist, a cannabinoid CB1 receptor antagonist, and a melanin-concentrating hormone receptor antagonist.

17. The pharmaceutical combination of claim 16, wherein the anti-obesity agent is at least one agent selected from the group consisting of rimonabant, orlistat, sibutramine, topiramate, zonisamide, dextroamphetamine, phentermine, phenylpropanolamine, diethylpropion, mazindol, doprexin and Axokine.

18. The pharmaceutical combination of claim 12, wherein the therapeutic agent is at least one lipid-lowering/lipid-modulating agent selected from the group consisting of a hydroxymethylglutaryl coenzyme A reductase inhibitor, a fibric acid derivative, a PPAR-alpha agonist, a PPAR-delta agonist, an acyl-coenzyme A:cholesterol acyltransferase inhibitor, probucol, a thyroid hormone receptor agonist, a cholesterol absorption inhibitor, a lipase inhibitor, a lipoprotein-associated phospholipase A2 inhibitor, a microsomal triglyceride transfer protein inhibitor, a low density lipoprotein receptor activator, a lipoxygenase inhibitor, a carnitine palmitoyl-transferase inhibitor, a squalene synthase inhibitor, a nicotinic acid derivative, a bile acid sequestrant, a sodium/bile acid cotransporter inhibitor, and a cholesterol ester transfer protein inhibitor.

19. The pharmaceutical combination of claim 18, wherein the lipid-lowering/lipid-modulating agent is at least one agent selected from the group consisting of pravastatin, lovastatin, simvastatin, atorvastatin, cerivastatin, fluvastatin, nisvastatin, visastatin, atavastatin, rosuvastatin, colestipol, cholestyramine, colestilan, colesevelam, fenofibrate, gemfibrozil, clofibrate, avasimibe, eflucimibe, eldacimibe, lecimibide, liothyronine, levothyroxine, rilapladib, darapladib, etomoxir, acipimox and torcetrapib.

20. A method for treating a condition selected from the group consisting of: type 1 or type II diabetes mellitus, hyperglycemia, diabetic complications, insulin resistance, metabolic syndrome, hyperinsulinemia, hypertension, hyperuricemia, obesity, edema, dyslipidemia, chronic heart failure, or atherosclerosis, which comprises administering an effective amount of a compound of claim 1 to a subject having said condition.

21. The method of claim 20, further comprising administering, concurrently or sequentially, a therapeutically effective amount of at least one additional therapeutic agent selected from the group consisting of an antidiabetic agent, a lipid-lowering/lipid-modulating agent, an agent for treating diabetic complications, an anti-obesity agent, an antihypertensive agent, an antihyperuricemic agent, and an agent for treating chronic heart failure or atherosclerosis.

22. A method of treating type I or type II diabetes comprising administering to a patient having type I or type II diabetes a therapeutically effective amount of a compound of claim 1 alone or in combination with at least one other therapeutic agent selected from the group consisting of an antidiabetic agent, a lipid-lowering/lipid-modulation agent, an agent for treating diabetic complications, an anti-obesity agent, an antihypertensive agent, an antihyperuricemic agent, and an agent for treating chronic heart failure or atherosclerosis.

23. A compound of the formula:

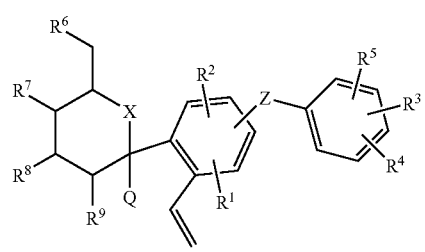

IIb wherein
Q is selected from the group consisting of hydroxy, a protected hydroxy group, and $C_2$-$C_5$ alkenyl;
X is selected from the group consisting of oxygen; sulfur; SO; $SO_2$; methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy; $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; and NH optionally substituted with a substituent independently selected from $C_1$-$C_6$ alkyl, $C_3$-$C_6$ cycloalkyl and ($C_1$-$C_4$ alkyl)carbonyl;

Z is a member selected from the group consisting of oxygen; sulfur; SO; $SO_2$; 1,1-cyclopropylene; carbonyl; and methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$) alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, aryl, heteroaryl, ($C_1$-$C_4$ alkyl)carbonyl, arylcarbonyl, heteroarylcarbonyl, hydroxycarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups or portions are optionally partly or completely fluorinated and optionally mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group is optionally replaced by CO or $SO_2$;

$R^2$ is a member selected from the group consisting of hydrogen, halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano and nitro, wherein alkyl groups or portions are optionally mono- or polysubstituted by fluorine, or in the event that $R^1$ and $R^2$ are bound to two adjacent C atoms of the phenyl ring, $R^1$ and $R^2$ are optionally joined together such that $R^1$ and $R^2$ together form a $C_3$-$C_5$ alkylene, $C_3$-$C_5$ alkenylene or butadienylene bridge, which is optionally partly or completely fluorinated or mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups are optionally replaced by an N atom;

$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$) alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_3$-$C_{10}$ cycloalkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_3$-$C_{10}$ cycloalkyl)$C_2$-$C_4$ alkenyl, $C_3$-$C_6$ cycloalkylidenmethyl, aryl, heteroaryl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, hydroxycarbonyl, ($C_1$-$C_4$ alkyloxy)carbonyl, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_6$ alkyloxy, $C_3$-$C_{10}$ cycloalkyloxy, $C_5$-$C_7$ cycloalkenyloxy, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, cycloalkenylsulfonyl, arylsulfanyl, arylsulfinyl, arylsulfonyl, amino, hydroxy, cyano or nitro, wherein alkyl, alkenyl, alkynyl, cycloalkyl- and cycloalkenyl groups or portions are optionally partly or completely fluorinated and optionally mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by O, S, CO, SO or $SO_2$, and in N-heterocycloalkyl groups a methylene group is optionally replaced by CO or $SO_2$;

$R^4$ is a member selected from the group consisting of hydrogen, halo, hydroxy, cyano, nitro, $C_1$-$C_3$ alkyl, $C_3$-$C_{10}$ cycloalkyl, $C_3$-$C_{10}$ cycloalkyloxy and $C_1$-$C_3$ alkyloxy, wherein alkyl groups or portions may be mono- or polysubstituted by fluorine, or if $R^3$ and $R^4$ are bound to two adjacent C atoms of the phenyl ring, $R^3$ and $R^4$ are optionally joined together such that $R^3$ and $R^4$ together form a $C_3$-$C_5$ alkylene, $C_3$-$C_5$ alkenylene or butadienylene bridge, which is optionally partly or completely fluorinated and optionally mono- or disubstituted by identical or different substituents selected from chlorine, hydroxy, $C_1$-$C_3$ alkoxy and $C_1$-$C_3$ alkyl, and wherein one or two methylene groups can be replaced independently of one another by O, S, CO, SO, $SO_2$ or $NR^a$, and wherein in the case of a butadienylene bridge one or two methyne groups are optionally replaced by an N atom;

$R^5$ is a member selected from the group consisting of hydrogen, halo, hydroxy, cyano, nitro, $C_1$-$C_3$ alkyl, $C_3$-$C_{10}$ cycloalkyl and $C_1$-$C_3$ alkyloxy, wherein alkyl groups or portions may be mono- or polysubstituted by fluorine; and $R^6$, $R^7$, $R^8$ and $R^9$ are each members independently selected from the group consisting of hydroxy, ($C_1$-$C_{18}$ alkyl)carbonyloxy, $(C_1-C_{18}$ alkyl)oxycarbonyloxy, arylcarbonyloxy, aryl-$(C_1-C_3$ alkyl)carbonyloxy, hydrogen, halo, $C_1-C_6$ alkyl, $C_2-C_6$ alkenyl, $C_2-C_6$ alkynyl, $(C_3-C_{10})$cycloalkyl-$(C_1-C_3)$alkyl, $(C_5-C_7)$cycloalkenyl-$(C_1-C_3)$alkyl, aryl-$(C_1-C_3)$alkyl, heteroaryl-$(C_1-C_3)$alkyl, $C_1-C_6$ alkyloxy, $C_2-C_6$ alkenyloxy, $C_2-C_6$ alkynyloxy, $(C_3-C_7)$cycloalkyloxy, $C_5-C_7$ cycloalkenyloxy, aryloxy, heteroaryloxy, $(C_3-C_7)$cycloalkyl-$(C_1-C_3)$alkyloxy, $(C_5-C_7)$cycloalkenyl-$(C_1-C_3)$alkyloxy, aryl-$(C_1-C_3)$alkyloxy, heteroaryl-$(C_1-C_3)$alkyloxy, aminocarbonyl, hydroxycarbonyl, $(C_1-C_4$ alkyl)aminocarbonyl, di-$(C_1-C_3$ alkyl)aminocarbonyl, $(C_1-C_4$ alkyloxy)carbonyl, aminocarbonyl-$(C_1-C_3)$alkyl, $(C_1-C_4$ alkyl)aminocarbonyl-$(C_1-C_3)$alkyl, di-$(C_1-C_3$ alkyl)aminocarbonyl-$(C_1-C_3)$alkyl, hydroxycarbonyl-$(C_1-C_3)$alkyl, $(C_1-C_4$ alkyloxy)carbonyl-$(C_1-C_3)$alkyl, $(C_3-C_7)$cycloalkyloxy-$(C_1-C_3)$alkyl, $(C_5-C_7)$cycloalkenyloxy-$(C_1-C_3)$alkyl, aryloxy-$(C_1-C_3)$alkyl, heteroaryloxy-$(C_1-C_3)$alkyl, $C_1-C_4$ alkylsulfonyloxy, arylsulfonyloxy, aryl-$(C_1-C_3)$alkyl-sulfonyloxy, trimethylsilyloxy, t-butyldimethylsilyloxy, and cyano, wherein alkyl, alkenyl, alkynyl, cycloalkyl and cycloalkenyl groups or portions are optionally partly or completely fluorinated and optionally mono- or disubstituted by identical or different substituents selected from chlorine, hydroxy, $C_1-C_3$ alkoxy and $C_1-C_3$ alkyl, and in cycloalkyl and cycloalkenyl groups one or two methylene groups are optionally replaced independently of one another by $NR^a$, O, S, CO, SO or $SO_2$; and $R^a$ is a member selected from the group consisting of H, $C_1-C_4$ alkyl and $C_1-C_4$ alkylcarbonyl.

24. The compound 5-chloro-6-(4-ethylbenzyl)-6'-(hydroxymethyl)-2,3,3',4',5',6'-hexahydrospiro[indene-1,2'-pyran]-3',4',5'-triol, or a pharmaceutically acceptable salt thereof.

25. A compound of claim 1, selected from the group consisting of 5-chloro-6-(4-ethylbenzyl)-3-(2-hydroxyethyl)-6'-(hydroxymethyl)-2,3,3',4',5',6'-hexahydrospiro[indene-1,2'-pyran]-3',4',5'-triol; 5-chloro-6-(4-ethylbenzyl)-6'-(hydroxymethyl)-2,3,3',4',5',6'-hexahydrospiro[indene-1,2'-pyran]-3,3',4',5'-tetraol; 5-chloro-6-(4-ethylbenzyl)-6'-(hydroxymethyl)-3-methoxy-2,3,3',4',5',6'-hexahydrospiro[indene-1,2'-pyran]-3',4',5'-triol; 5-chloro-6-(4-ethylbenzyl)-3-fluoro-6'-(hydroxymethyl)-2,3,3',4',5',6'-hexahydrospiro[indene-1,2'-pyran]-3',4',5'-triol; 5-chloro-6'-(hydroxymethyl)-6-(4-(tetrahydrofuran-3-yloxy)benzyl)-2,3,3',4',5',6'-hexahydrospiro[indene-1,2'-pyran]-3',4',5'-triol; 5-chloro-6-(4-ethylbenzyl)-3',4',5'-trihydroxy-2,3,3',4',5',6'-hexahydrospiro[indene-1,2'-pyran]-6'-yl)methyl methyl carbonate; 5-chloro-6-(4-ethylbenzyl)-3',4',5'-trihydroxy-2,3,3',4',5',6'-hexahydrospiro[indene-1,2'-pyran]-6'-yl)methyl ethyl carbonate; 5-chloro-6-(4-ethoxybenzyl)-3',4',5'-trihydroxy-2,3,3',4',5',6'-hexahydrospiro[indene-1,2'-pyran]-6'-yl)methyl isopropyl carbonate; and 5-chloro-6-(4-ethoxybenzyl)-3',4',5'-trihydroxy-2,3,3',4',5',6'-hexahydrospiro[indene-1,2'-pyran]-6'-yl)methyl 3,3-dimethylbutanoate or a pharmaceutically acceptable salt or prodrug thereof.

26. A pharmaceutical composition comprising a compound of claim 24 in a pharmaceutically acceptable carrier.

27. A pharmaceutical composition comprising a compound of claim 25, in a pharmaceutically acceptable carrier.

28. A method for treating a condition selected from the group consisting of: type 1 or type II diabetes mellitus, hyperglycemia, diabetic complications, insulin resistance, metabolic syndrome, hyperinsulinemia, hypertension, hyperuricemia, obesity, edema, dyslipidemia, chronic heart failure, or atherosclerosis, which comprises administering an effective amount of a compound of claim 24 or 25 to a subject having said condition.

29. A compound of claim 24 or 25 which is the 1S,3'R,4'S,5'R,6'R isomer.

* * * * *

UNITED STATES PATENT AND TRADEMARK OFFICE
CERTIFICATE OF CORRECTION

PATENT NO. : 7,803,778 B2  
APPLICATION NO. : 11/752226  
DATED : September 28, 2010  
INVENTOR(S) : Chen et al.

Page 1 of 1

It is certified that error appears in the above-identified patent and that said Letters Patent is hereby corrected as shown below:

On the Title Page:

Item [56] References Cited:

Please delete: "6,089,238 A    7/2000    Schneider et al."
and replace it with: -- 6,069,238 A    5/2000    Hitchcock et al. --

Column 70, Claim 1, Line 64: please insert -- $C_1$-$C_4$ -- after "alkylsulfinyl," but before "alkylsul-"

Column 72, Claim 8, Line 18: please delete "$CH_1$" and replace it with -- $CH_2$ --

Signed and Sealed this

Fifteenth Day of February, 2011

David J. Kappos
*Director of the United States Patent and Trademark Office*